US005854071A

United States Patent [19]

Oppermann et al.

[11] Patent Number: 5,854,071
[45] Date of Patent: Dec. 29, 1998

[54] OP-3- INDUCED MORPHONGENESIS

[75] Inventors: Hermann Oppermann, Medway; Engin Ozkaynak, Milford; Thangavel Kuberasampath, Medway; David C. Rueger, Hopkinton, all of Mass.; Roy H. L. Pang, Etna, N.H.; Charles M. Cohen, Medway, Mass.

[73] Assignee: Creative BioMolecules, Inc., Boston, Mass.

[21] Appl. No.: 901,200

[22] Filed: Jul. 28, 1997

Related U.S. Application Data

[62] Division of Ser. No. 479,666, Jun. 7, 1995, Pat. No. 5,652,337, which is a division of Ser. No. 971,091, Nov. 3, 1992, abandoned, which is a continuation-in-part of Ser. No. 922,813, Jul. 31, 1992, abandoned, which is a continuation-in-part of Ser. No. 752,964, Aug. 29, 1991, abandoned, which is a continuation-in-part of Ser. No. 667,274, Mar. 11, 1991, abandoned, and a continuation-in-part of Ser. No. 923,780, Jul. 31, 1992, abandoned, which is a continuation-in-part of Ser. No. 752,764, Aug. 30, 1991, abandoned, and a continuation-in-part of Ser. No. 752,857, Aug. 30, 1991, abandoned, which is a continuation-in-part of Ser. No. 946,238, Sep. 16, 1992, abandoned, and a continuation-in-part of Ser. No. 667,274, Mar. 11, 1991, abandoned, and a continuation-in-part of Ser. No. 938,336, Aug. 28, 1992, abandoned, and a continuation-in-part of Ser. No. 938,337, Aug. 28, 1992, abandoned, and a continuation-in-part of Ser. No. 753,059, Aug. 30, 1991, abandoned, which is a continuation-in-part of Ser. No. 667,274, Mar. 11, 1991, abandoned, and a continuation of Ser. No. 938,021, Aug. 28, 1992, abandoned, which is a continuation-in-part of Ser. No. 752,861, Aug. 30, 1991, abandoned, which is a continuation-in-part of Ser. No. 667,274, Mar. 11, 1991, abandoned, which is a continuation-in-part of Ser. No. 945,285, Sep. 15, 1992, abandoned, which is a continuation-in-part of Ser. No. 945,286, Sep. 15, 1992, abandoned, which is a continuation-in-part of Ser. No. 752,764, Aug. 30, 1991, abandoned, which is a continuation-in-part of Ser. No. 946,235, Sep. 16, 1992, abandoned.

[51] Int. Cl.$^6$ .............................. C12N 5/06; C12N 5/08; C07K 14/00; C07K 14/51

[52] U.S. Cl. ......................... 435/353; 435/325; 435/366; 530/350; 530/399

[58] Field of Search ................................ 530/350, 399; 435/325, 353, 366, 372

[56] References Cited

U.S. PATENT DOCUMENTS

| | | | |
|---|---|---|---|
| 4,877,864 | 10/1989 | Wang et al. | 514/12 |
| 4,968,590 | 11/1990 | Kuberasampath et al. | 530/326 |
| 4,975,526 | 12/1990 | Kuberasampath et al. | 530/350 |
| 5,002,965 | 3/1991 | Ramwell et al. | 435/1.2 |
| 5,011,691 | 4/1991 | Oppermann et al. | 424/423 |
| 5,013,649 | 5/1991 | Wang et al. | 435/69.1 |
| 5,091,513 | 2/1992 | Huston et al. | 530/387.1 |
| 5,106,626 | 4/1992 | Parsons et al. | 424/423 |
| 5,108,753 | 4/1992 | Kuberasampath et al. | 424/422 |
| 5,141,905 | 8/1992 | Rosen et al. | 435/69.1 |

FOREIGN PATENT DOCUMENTS

| | | |
|---|---|---|
| 1128881 | 8/1982 | Canada . |
| 0148155 | 7/1985 | European Pat. Off. . |
| 0416578 | 3/1991 | European Pat. Off. . |
| WO88/00205 | 1/1988 | WIPO . |
| WO89/09787 | 10/1989 | WIPO . |
| WO89/09788 | 11/1989 | WIPO . |
| WO89/10409 | 11/1989 | WIPO . |
| WO90/03733 | 4/1990 | WIPO . |

OTHER PUBLICATIONS

Wong et al. (1975), "Targeted Cells In Bone For Parathormone And Calcitonin Are Different: Enrichment For Each Cell Type By Sequential Digestion Of Mouse Calvaria And Selective Adhesion To Polymer Surfaces," 72 *Proc. Natl. Acad. Sci. USA* 3167–3171.

Sampath et al. (1983), "Homology Of Bone–Inductive Proteins From Human, Monkey, Bovine, And Rat Exttacellular Matrix," 80 *Proc. Natl. Acad. Sci. USA* 6591–6595.

Mason et al. (1985), "Complementary DNA Sequences Of Ovarian Follicular Fluid Inhibin Show Precursor Structure And Homology With Transforming Growth Factor–β," 318 *Nature*, 659–663.

Cate et al. (1986) "Isolation of the Bovine and Human Genes for Müllerian Inhibiting Substance and Expression of the Human Gene in Animal Cells," 45 *Cell* 685–698.

Edelman (1986), "Cell Adhesion Molecules in the Regulation of Animal Form and tissue Pattern," 2 *Ann. Rev. Cell Biol* 81–116.

Miller et al. (1987), "Phenotypic Modulation of the Swarm Rat Chondrosarcoma Induced by Morphogenetic Bone Matrix$^1$," 42 *Cancer Research* 2589–3594.

Padgett et al. (1987), "A Transcript From A Drosophila Pattern Gene Predicts A Protein Homologous To The Transforming Growth Factor–β Family," 325 *Nature* 81–84.

Weeks et al. (1987), "A Maternal mRNA Localized to the Vegetal Hemisphere in Xenopus Eggs Codes for a Growth Factor Related to TGF–β," 51 *Cell* 861–867.

Wang et al.; Wozney et al.; and Rosen et al. (1988), "Purification and Charaterization of Cartilage and Bone Inducing Factors," Identification Through Molecular Cloning of Factors Involved in In Vivo Cartilage Formation, and Developmental Expression of Cartilage and Bone–Specific Genes In The Rat Embryo, 42 *Calcified Tissue Int.* (Suppl.): Abstract Nos. 146, 147 and 136.

Wang et al. (1988), "Purification and Characterization of Other Distinct Bone–Inducing Factors" 85 *Proc. Natl. Acad. Sci. USA*, 9484–9488.

(List continued on next page.)

Primary Examiner—George C. Elliott
Assistant Examiner—Robert Schwartzman
Attorney, Agent, or Firm—Testa, Hurwitz & Thibeault

[57] ABSTRACT

Disclosed are (1) nucleic acid and amino acid sequences for a novel morphogenic protein; (2) methods for producing and expressing the protein in a biologically active form; and (3) methods for utilizing the protein to induce tissue morphogenesis in a mammal, including methods for increasing a progenitor cell population in a mammal, methods for stimulating progenitor cells to differentiate and maintain their differentiated phenotype in vivo or in vitro, methods for inducing tissue-specific growth in vivo and methods for the replacement of diseased or damaged tissue in vivo.

8 Claims, 3 Drawing Sheets

OTHER PUBLICATIONS

Wozney et al. (1988), "Novel Regulators of Bone Formation: Molecular Clones and Activities," 242 *Science* 1528–1534.

Ausubel et al. (1989) "Current Protocols in Molecular Biology," (John Wiley & Sons, N.Y.).

Lyons et al. (1989), "Patterns Of Expression Of Murine Vgr–1 And BMP–2a RNA Suggest That Transforming Factor–β–Like Genes Coordinately Regulate Aspects Of Embryonic Development," 3 *Genes & Development* 1657–1668.

Lyons et al. (1989), "Vgr–1, A Mammalian Gene Related To Xenopus Vg–1, Is A Member Of The Transforming Growth Factor β Gene Superfamily," 86 *Proc. Natl. Acad. Sci. USA* 4554–4558.

Mason et al. (1989), "Activin B: Precursor Sequences, Genomic Structure and in Vitro activities," 3 *Mol. Endocrinology* 1352–1358 (1989).

Rosen et al. (1989), "Purification and Molecular Cloning of a Novel Group of BMPS and Localization of BMP MRNA In Developing Bone," 20 *Connect. Tissue Res.* 1–5:313–319.

Behringer et al. (1990), "Abnormal Sexual Development In Transgenic Mice Chronically Expressing Müllerian Inhibiting Substance," 345 *Nature* 167–170.

Celeste et al. (1990), "Identification of Transforming Growth Factor Beta Family Members Present in Bone–Inductive Protein Purified from Bovine Bone," 87 *Proc. Natl. Acad. Sciences USA* 9843–9847.

Green et al. (1990), "Graded Changes In Dose Of A Xenopus Activin A Homologue Elicit Stepwise Transtions In Embryonic Cell Fate," 347 *Nature* 391–394.

Katagiri et al. (1990), "The Non–Osteogenic Mouse Pluripotent Cell Line, C3H10T1/2 is Introduced to Differentiate Into Osteoblastic Cells by Recombinant Human Bone Morphogenetic Protein–2," 172 *Biochem. Biophys. Res. Comm.* 1:295–299.

Lee (1990), "Identification of a Novel Member (GDF–1) of the Transforming Growth Factor–β Superfamily," 90 *Mol. Endrocr.* 1034–1040.

Ozkaynak et al. (1990), "OP–1 cDNA Encodes An Osteogenic Protein In The TGF–β Family," 9 *EMBO J.* 2085–2093.

Panganiban et al. (1990), "Biochemical Characterization of the *Drosophila dpp* Protein, a Member of the Transforming Growth Factor β Family of Growth Factors," 10 *Mol. Cell. Biol.* 2669–2677.

Rosen et al.; Celeste et al. (1990), "In Vivo and In Vitro Roles of BMP in Skeletal Formation and Repair," Highly Purified Bovine Bone–Inductive Activity Contains Multiple Protein Species Related to BMP–2, *J. Cell Biochem. Suppl.* 14E, 33 (Abstract No. 0004); 54 (Abstract No. 105).

Sampath et al. (1990), "Bovine Osteogenic Protein Is Composed of Dimers of OP–1 and BMP–2A, Two Members of the Transforming Growth Factor–B Superfamily," 265 *J. Biol. Chem.* 13198–13205.

Schubert et al. (1990), "Activin Is A Nerve Cell Survival Molecule," 344 *Nature* 868–870.

Smith et al. (1990), "Identification of A Potent Xenopus Mesoderm–Inducing Factor As A Hormologue Of Activin A," 345 *Nature* 729–731.

Sokol et al. (1990), "A Mouse Macrophage Factor Induces Head Structures and Organizes a Body Axis in Xenopus," 249 *Science* 561–563.

Wang et al. (1990), "Recombinant Human Bone Morphogenetic Protein Induces Bone Formation," 87 *Proc. Natl. Acad. Sci. USA* 2220–2224.

Wozney (1990), "Bone Morphogenic Proteins," 1 *Prog. In Growth Factor Res.* 267–280.

Wozney et al. (1990), "Growth Factors Influencing Bone Development," 13 *J. Cell Sci. Suppl.* 149–156.

Yannas (1990), "Biologically Active Analogues of the Extracellular Matrix: Artificial Skin and Nerves," 29 *Angew. Chem. Int. Ed. Engl.* 20–35.

D'Allesandro et al. (1991), "Purification, Characterization and, Activity of Recombinant Human BMP–5," *J. Cell. Biochem.* Suppl. 166 (Abstract No. 0105).

Israel et al. (1991), "Expression of Recombinant BMP–2 in Chinese Hamster Ovary Cells," *J. Cell. Biochem.* Suppl. 168 (Abstract No. Q–111).

Lee (1991), "Expression Of Growth/Differentiation Factor 1 In The Nervous System: Conservation Of A Bicistronic Structure," 88 *Proc. Natl. Acad. Sci. USA* 4250–4254.

Takuwa et al. (1991), "Bone Morphogenetic Protein–2 Stimulates Alkaline Phosphatase Activity and Collagen Synthesis in Cultured Osteoblastic Cells, MC3T3–E1," 174 *Biochem. Biophys. Res. Comm.* 1:96–101.

Ozkaynak et al. (1991), "Murine Osteogenic Protein–1 (OP–1): High Levels of mRNA in Kidney," 179 *Biochem. Biophys. Res. Commun.* 116–123.

Wharton et al. (1991), "Drosophila 60 A Gene, Another Transforming Growth Factor β Family Member, is Closely Related to Human Bone Morphogenetic Proteins," 88 *Proc. Natl. Acad. Sci. USA* 9214–9218.

Yamaguchi et al. (1991), "Recombinant Human Bone Morphogenetic Protein–2 Stimulates Osteoblastic Maturation and Inhibits Myogenic Differentiation In Vitro," 113 *J. Cell. Biol.* 3:681–687.

Israel et al. (1992), "Expression and Characterization of Bone Morphogenetic Protein–2 in Chinese Hamster Ovary Cells," 7 *Growth Factors* 139–150.

Rogers et al. (1992), "Bone Morphogenetic Proteins–2 and –4 are Involved In The Retinoic Acid–Induced Differentiation of Embryonal Carcinoma Cells," 3 *Mol. Biol. Cell* 2:189–196.

Thies et al. (1992), "Recombinant Human Bone Morphogenetic Protein–2 Induces Osteoblastic Differentiation in W–20–17 Stromal Cells," 130 *Endocrinology* 3:1318–1324.

Wozney et al.; Celeste et al.; Rosen et al. (1992), "Regulation of Chrondrogenesis and Osteogenesis by the BMP Proteins;" Molecular Cloning of BMP–8: A Protein Present in Bovine Bone Which is Highly Related to the BMP5/5/7 Subfamily of Osteoinductive Molecules; Isolation and Characterization of BMP–Responsive Cartilage and Bone Cell Progenitors From Mouse Embryo Limb Buds, *J. Cell Biochem. Suppl.* 16F, 76 (Abstract No. W026), 100 (Abstract No. W502) and 103 (Abstract No. W513).

Wozney (1992), "The Bone Morphogenetic Protein Family and Osteogenesis," 32 *Mol. Reprod. & Dev.* 160–167.

Padgett et al. (1993), "Human BMP Sequences Can Confer Normal Dorsal–Ventral Patterning in the Drosphila Embryo," 90 *Proc. Natl. Acad. Sci. USA* 2905–2909.

```
                        10              20              30              40              50              60              70
mOP-2                                                                                                                        1
mOP-3    ATGGCTATGCGTCGTCCCGGCCACTCTGGCTATTGGCCTTGCTCTGTGCGCTGGGAGGCGGCCACGGTCCGCG
         ATGGCTGCGCTGCGCTCGGGACTCCTATGCGGCTACTGGGCCTCTGTGTGCTGGGCGGCGGTCACCTCTGCA
         └── EXON 1

80              90             100             110             120             130             140
mOP-2    TCCCCCGCACACCTGTCCCCAGCGTCGCGGAGCCTGGGACGCGGCAGCGTGAAATCCTGGCGG
mOP-3    TCCCCCGCACGTCTTTCCCCAGCGTCGACTAGGAGTACGCGAGCACGCGACATGCAGCGCGAGATTCGGGAGG 150             160             170             180             190             200             210             220
mOP-2    TGCTCGGGCTACCGGGACGGCCCCCACCCCGTCACAACCCGCGTCGGTCCCGAGCCCGGCAGCGTCCGCCCCTC
mOP-3    TGCTGGGGCTAGCCGGGCGGCCCCGATCCCGAGCACCGGTCGCGAGCACCCAGCAGCCAGCCTCTGCGCCCCTC 230             240             250             260             270             280             290
mOP-2    TTCATGTTGGACCTATACCACGCCATGACCGATGACGACGGCGCCACCAGGCTCACTTAGGCCGTGC
mOP-3    TTTATGTTGGACCTGTACCGTGCCATGACGGATGACGACAGTGGCGGTGGGACCCCGCAGCCTCACTTGGACCGTGC 300             310             320             330             340             350             360             370
mOP-2    CGACCCTGGTCATGAGCTTCGTCAACATGGTGGAACGCGACCGTACCCTGGGCTACCCTGGGCTACCAGGAGCCACACTGGAAGG
mOP-3    TGACCCTGATTATGAGCTTTGTCAACATAGTGAACGCGACCGTACCCTGGCTACCAGGAGCCACACTGGAAGG
                                                              └── EXON 2

380             390             400             410             420             430             440
mOP-2    CGACCCTGGTCATGAGCTTCGTCAACATGGTGGAACGCGACCGTACCCTGGGCTACCCTGGGCTACCAGGAGCCACACTGGAAGG
mOP-3    AATTCCACTTTGACCTAACCCAGATCCCTGCTGGGGAGGCTGTCACAGCTGCTGAGTTCCGGATCTACAAAGAA
         AATTCCACTTTGACCTAACCCAGATCCCTGCTGGGGAGGCTGTCACAGCTGCTGAGTTCCGGATCTACAAAGAA
```

Fig. 1

```
             450         460         470         480         490         500         510
mOP-2   CCCAGCACCCACCCGCTCAACACAACCCTCCACATCAGCATGTTCGAAGTGGTCACTCCAACAGGA
mOP-3   CCCAGTACCCACCCGCTCAACACAACCCTCCACATCAGCATGTTCGAAGTGGTCACTCCAACAGGA
             EXON 2                                                        EXON 3

20  530         540         550         560         570         580         590
mOP-2   GTCTGACTTGTTCTTTTTGGATCTTCAGACGCTCCGATCTGGGGACGAGGGCTGGCTGCTGGACATCACAG
mOP-3   GTCTGACTTGTTCTTTTTGGATCTTCAGACGCTCCGATCTGGGGACGAGGGCTGGCTGCTGGACATCACAG
             EXON 3

600         610         620         630         640         650         660
mOP-2   CAGCCAGTGACCGATGGCTGCTGAACCATCACAAGGACCTGGGACTCCGCCTCTATGTGGAAACCGGGATGGG
mOP-3   CAGCCAGTGACCGATGGCTGCTGAACCATCACAAGGACCTAGGACTCCGCCTCTATGTGGAAACCGGGATGGG
                                                                                EXON 3

670         680         690         700         710         720         730         740
mOP-2   CTTCTTCAGGGCCAGCCAGAGTCCTGTGCCCACCCCAGAGTCCTGTGCGGGCCCCTCGGCTTGGACGACAAGCACCACGCTCCAGACAGCCTTTCATGGTAAC
mOP-3   TTTCTTCAGGGCCAGCCAGAGTCCTGTGCCCACCCCAGAGTCCTGTGCGGGCCCCTCGAACAGCAACAGCACCACGCTCCAGACAGCCTTTCATGGTTGG
             EXON 4                                                                                       EXON 5

820         830         840         850         860         870         880          8
mOP-2   AAACGAACCAGCTGCCGCACTCCGACTCCAAACAAACCTCCCAGGGATCTTTGATGATGGCCACGGTTCCCGCGGCCAGCCAAAGA
mOP-3   AAATCAACCAGCTGCCGCACTCCAACAAACACCTAGAATCCTTGATGATGGCCACGGTTCTCACGGCCAGAGAAGCAGCTAAATC
             EXON 4                                                                 EXON 5
```

Fig. 1 cont.

```
         90       900       910       920       930       940       950       960
mOP-2   GTTTGCCGCAGGCATGAGCTCTACGTCAGCTTCCGTGACCTTGGCTGGACTGGGTCATCGCCCCCAGGG
mOP-3   GTTTGCCGCAGGCATGAGCTCTATGTCAGCTTCCGTGACCTTGGCTGGACTGGGTCATCGCCCCCAGGG
                                                                  EXON 5

970       980       990      1000      1010      1020      1030
mOP-2   CTACTCTGCCTATTACTGTGAGGGGGAGTGTGCTTTCCCACTGAACTCCTGTATGAACGCCACCAACCATGCCA
mOP-3   CTACTCCGCCTATTACTGTGCTGGGGAGTGCATTCACCTACCCACTGAACTCCTGTATGAACTCCACCAACCACGCCA
                                                                  EXON 6

1040      1050      1060      1070      1080      1090      1100      1110
mOP-2   TCTTGCAGTCTCTGTGCACCTGATGAAGCCAGATGTGTCCCCAAGGCATGCTGTGCACCCACCAAAACTGAGT
mOP-3   CTATGCAGGCCCTGTGCACTCTGGTACATCTGATGAAGCCAGATATCATCCCCAAGGTGTGCTGTGCTACTGAGCTGAGT
                        EXON 6

1120      1130      1140      1150      1160      1170      1180
mOP-2   GCCACCCTCTGTGCTGTGTACTATGACAGCAGCAACAATGTCATCCTGCGTAAACACCGTAACATGGTGGTCAAGGC
mOP-3   GCCATTTCTCTGCTCTACTATGATAGAAAACAATAATGTCATCCTGCGCAGGAGCCAACATGGTAGTCCAGGC
                        EXON 7

1190      1200
mOP-2   CTGTGGCTGCCACTGA
mOP-3   CTGTGGCTGCCACTGA
        ——— EXON 7 ———→
```

Fig. 1 cont.

OP-3- INDUCED MORPHONGENESIS

REFERENCE TO RELATED APPLICATIONS

This application is a divisional of copending U.S. application Ser. No. 08/479,666, filed on Jun. 7, 1995, U.S. Pat. No. 5,652,337, which is a divisional of U.S. Ser. No. 07/971,091, filed Nov. 3, 1992, abandoned, which is a continuation-in-part of: (1) U.S. Ser. No. 07/922,813, filed Jul. 31, 1992, abandoned, which is a continuation-in-part of U.S. Ser. No. 07/752,964, filed Aug. 29, 1991, abandoned, which is a continuation-in-part of U.S. Ser. No. 07/667,274, filed Mar. 11, 1991 abandoned; (2) U.S. Ser. No. 07/923,780, filed Jul. 31, 1992, abandoned, which is a continuation-in-part of U.S. Ser. No. 07/752,764 and U.S. Ser. No. 07/752,857, both filed Aug. 30, 1991, both abandoned, and both continuations-in-part of U.S. Ser. No. 07/667,274, filed Mar. 11, 1991 abandoned,; (3) U.S. Ser. No. 07/938,336 and U.S. Ser. No. 07/938,337, both filed Aug.28, 1992, both abandoned, and both continuations-in-part of U.S. Ser. No. 07/753,059, filed Aug. 30, 1991, abandoned, which is a continuation-in-part of U.S. Ser. No. 07/667,274, filed Mar. 11, 1991 abandoned; (4) U.S. Ser. No. 07/938,021, filed Aug. 28, 1992, abandoned, which is a continuation-in-part of U.S. Ser. No. 07/752,861, filed Aug. 30, 1991, abandoned, which is a continuation-in-part of U.S. Ser. No. 07/667,274, filed Mar. 11, 1991 abandoned; (5) U.S. Ser. No. 07/945,285 and U.S. Ser. No. 07/945,286, both filed on Sep. 15, 1992, both abandoned, and both continuations-in-part of U.S. Ser. No. 07/752,764, filed Aug. 30, 1991, abandoned, which is a continuation-in-part of U.S. Ser. No. 07/667,274, filed Mar. 11, 1991 abandoned; (6) U.S. Ser. No. 07/946,235 and U.S. Ser. No. 07/946,238, both filed Sep. 16, 1992, both abandoned, and both continuations-in-part of U.S. Ser. No. 07/752,764, filed Aug. 30, 1991, abandoned, which is a continuation-in-part of U.S. Ser. No. 07/667,274, filed Mar. 11, 1991 abandoned. The disclosures of these applications are incorporated by reference herein.

FIELD OF THE INVENTION

This invention relates generally to the field of tissue morphogenesis and more particularly to a novel protein that induces tissue morphogenesis in mammals.

BACKGROUND OF THE INVENTION

Cell differentiation is the central characteristic of morphogenesis which initiates in the embryo, and continues to various degrees throughout the life of an organism in adult tissue repair and regeneration mechanisms. The degree of morphogenesis in adult tissue varies among different tissues and is related, among other things, to the degree of cell turnover in a given tissue. On this basis, tissues can be divided into three broad categories: (1) tissues with static cell populations such as nerve and skeletal muscle where there is no cell division and most of the cells formed during early development persist throughout adult life; (2) tissues containing conditionally renewing populations such as liver where there is generally little cell division but, in response to an appropriate stimulus, cells can divide to produce daughters of the same differentially defined type; and (3) tissues with permanently renewing populations including blood, testes and stratified squamous epithelia which are characterized by rapid and continuous cell turnover in the adult. Here, the terminally differentiated cells have a relatively short life span and are replaced through proliferation of a distinct subpopulation of cells, known as stem or progenitor cells.

The cellular and molecular events which govern the stimulus for differentiation of these cells is an area of intensive research. In the medical field, it is anticipated that the discovery of factor(s) which control cell differentiation and tissue morphogenesis will advance significantly medicine's ability to repair and regenerate diseased or damaged mammalian tissues and organs. Particularly useful areas include reconstructive surgery and in the treatment of tissue degenerative diseases including arthritis, emphysema, osteoporosis, cardiomyopathy, cirrhosis, and degenerative nerve diseases.

A number of different factors have been isolated in recent years which appear to play a role in cell differentiation. Recently, various members of the structurally related proteins of the transforming growth factor (TGF)-$\beta$ superfamily of proteins have been identified as true morphogens.

This "family" of proteins, sharing substantial amino acid sequence homology within their morphogenically active C-terminal domains, including a conserved six or seven cysteine skeleton, are capable of inducing tissue-specific morphogenesis in a variety of organs and tissues, including bone, cartilage, liver, dentin, periodontal ligament, cementum, nerve tissue and the epithelial mucosa of the gastrointestinal tract. The proteins apparently bind to surface receptors or otherwise contact and interact with progenitor cells, predisposing or stimulating the cells to proliferate and differentiate in a morphogenically permissive environment. The morphogens are capable of inducing the developmental cascade of cellular and molecular events that culminate in the formation of new organ-specific tissue, including any vascularization, connective tissue formation, and nerve ennervation as required by the naturally occurring tissue.

Among the proteins useful in tissue morphogenesis are proteins originally identified as bone inductive proteins, such as the OP-1, (also referred to in related applications as "OP1"), OP-2 (also referred to in related applications as "OP2"), and the CBMP2 proteins, as well as amino acid sequence-related proteins such as BMP5, BMP6 and its murine homolog, Vgr-1, DPP and 60A (from Drosophila), Vg1 (from Xenopus), and GDF-1 (from mouse see, for example, U.S. Ser. No. 752,764, abandoned, U.S. Ser. No. 667,274, abandoned, and U.S. Ser. No. 923,780, abandoned, and PCT documents US92/01968 and US92/07358). These TGF-$\beta$ superfamily members comprise a distinct subfamily of proteins different from other members of the TGF-$\beta$ superfamily in that the family of morphogenic proteins are able to induce the full cascade of events that result in tissue morphogenesis, including stimulating cell proliferation and cell differentiation, supporting the growth and maintenance of differentiated cells and inducing the "redifferentiation" of transformed cells to display a morphology characteristic of untransformed cells. The morphogenic proteins apparently can act as endocrine, paracrine or autocrine factors. Specifically, the endogenous morphogens may be synthesized by the cells on which they act, by neighboring cells, or by cells of a distant tissue, the secreted protein being transported to the cells to be acted on. In addition, the family of morphogenic proteins induce true tissue morphogenesis, rather than inducing formation of fibrotic (scar) tissue as, for example, TGF-$\beta$ does.

The morphogens are synthesized in the cell as a precursor molecule approximately three times larger than the mature protein that is processed to yield mature disulfide-linked dimers comprising the C-terminal domain of the precursor sequence. The proteins are inactive when reduced e.g., in monomeric form, but are active as oxidized homodimeric species as well as when oxidized in combination with other morphogens to produce heterodimers. The proteins useful in tissue morphogenesis typically require a suitable environment enabling cells to migrate, proliferate and differentiate in a tissue-specific manner into, e.g., cartilage-producing chondroblasts, bone-producing osteoblasts, hemopoietic cells, or liver cells, depending on the nature of the local environment. The proliferation and differentiation of cells induced by the morphogenic proteins requires a suitable local environment, including a suitable substratum on which the cells can anchor. The proliferating and differentiating cells also require the presence of appropriate signals to direct their tissue-specificity, such as cell surface markers.

It is an object of this invention to provide a novel purified morphogenic protein, "OP-3", including the amino acid sequence defining it and nucleic acids encoding it, including allelic, species, mutant and chimeric variants thereof, and methods for utilizing the protein to induce the developmental cascade of tissue morphogenesis for a variety of tissues in mammals. The morphogenic properties of OP-3 include the ability to induce proliferation and differentiation of progenitor cells, and the ability to support and maintain the differentiated phenotype through the progression of events that results in the formation of adult tissue. Another object is to provide methods for the expression and isolation of morphogenically active species of OP-3 using recombinant DNA techniques. Yet another object is to provide generic sequences defining useful morphogens. Still another object is to provide tissue-specific acellular matrices that may be used in combination with OP-3, and methods for their preparation. Other objects include utilizing OP-3 in a variety of applications including methods for increasing a progenitor cell population in a mammal; methods for stimulating progenitor cells to differentiate in vivo or in vitro and to maintain their differentiated phenotype; methods for inducing tissue-specific growth in vivo, and methods for the replacement of diseased or damaged tissue in vivo. These and other objects and features of the invention will be apparent from the description, drawings, and claims which follow.

SUMMARY OF THE INVENTION

A novel substantially pure genetic sequence encoding a novel substantially pure protein referred to herein as "OP-3" now has been discovered. This novel protein is a member of the morphogenic protein family previously described by Applicants (see U.S. Ser. No. 667,274, abandoned and U.S. Ser. No. 752,764, abandoned). Accordingly, the invention provides methods for utilizing OP-3 to induce the developmental cascade of tissue morphogenesis in a mammal. Specifically, methods are provided for utilizing OP-3 to induce the proliferation of uncommitted progenitor cells, to induce the differentiation of these stimulated progenitor cells in a tissue-specific manner under appropriate environmental conditions, and to support the growth and maintenance of these differentiated cells. The protein also may be used to stimulate the "redifferentiation" of cells that have strayed from their differentiated phenotypes. Accordingly, OP-3 can be utilized to initiate and maintain the developmental cascade of tissue morphogenesis in an appropriate, morphogenically permissive environment.

As used herein, useful OP-3 morphogens include proteins encoded by the DNA sequence provided in Seq. ID No. 1 ("mOP-3") and allelic and species variants thereof, as well as other naturally-occurring and biosynthetic mutants, including chimeric proteins, that are morphogenically active as defined herein. "Morphogenically active fragment" is understood to include all proteins and protein fragments encoded by part or all of the sequence of Seq. ID No. 1 and which have morphogenic activity as defined herein. Specifically, as defined herein, a morphogen is a dimeric protein comprising a pair of polypeptide chains, wherein each polypeptide chain comprises at least the C-terminal six cysteine skeleton defined by residues 303 to 399 of Seq. ID No. 1 (or residues 335–431 of OP1, Seq. ID no. 3), including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

In one aspect, the morphogens of this invention comprise a morphogenically active dimeric species comprising a pair of polypeptide chains, wherein at least one of the polypeptide chains comprises the amino acid sequence defined by residues 303 to 399 of Seq. ID No. 1 including allelic, species and other mutant variants thereof. In preferred morphogens, at least one polypeptide chain comprises the sequence defined by residues 298–399, residues 261–399 or residues 264–399 of Seq. ID No. 1. Alternatively, the amino acid sequence of both polypeptide chains may be defined by part or all of the amino acid sequence of Seq. ID No. 1, including allelic, species and other mutant variants thereof including chimeric constructs as described below. Where only one polypeptide chain is defined by the amino acid sequence of part or all of Seq. ID. No. 1, the other polypeptide chain preferably comprises at least the sequence defining the C-terminal six cysteine skeleton of any of the other known morphogen family members, including OP-1, OP-2, CBMP2A, CBMP2B, BMP3, BMP5, BMP6, Vgr-1, Vg1, 60A, DPP and GDF-1 (described, for example, in U.S. Ser. Nos. 752,764, abandoned 923,780, abandoned or US92/07358), including allelic, species and other mutant variants thereof, including chimeric variants. Other useful sequences include biosynthetic constructs, such as are described in U.S. Pat. No. 5,011,691.

In still another aspect of the invention, generic sequences are provided which accommodate the sequence identity of useful morphogens and incorporate OP-3's novel features.

In another aspect of the invention, morphogens of this invention comprise morphogenically active proteins encoded by part or all of the genetic sequence listed in Seq. ID No. 1, including allelic, species and other mutant variants thereof. In still another aspect, the invention comprises morphogens encoded by nucleic acids that hybridize to part or all of the pro region of the OP-3 protein, bases 120 to 848 of Seq ID No. 1, under stringent hybridization conditions. As used herein, "stringent hybridization conditions" are defined as hybridization in 40% formamide, 5×SSPE, 5×Denhardt's Solution, and 0.1% SDS at 37° C. overnight, and washing in 0.1×SSPE, 0.1% SDS at 50° C..

In one aspect of the invention, morphogenically active fragments of OP-3 are useful in the replacement of diseased or damaged tissue in a mammal, including, but not limited to, damaged lung tissue resulting from emphysema; cirrhotic tissue, including cirrhotic kidney or liver tissue; damaged heart or blood vessel tissue, as may result from cardiomyopathies and/or atherothrombotic or cardioembolic strokes; damaged stomach and other mucosal tissues of the gastrointestinal tract resulting from ulceric perforations and/or their repair; damaged nerve tissue as may result from physical injury, degenerative diseases such as Alzheimer's disease, multiple sclerosis, or strokes; damaged cartilage and bone tissue as may result from metabolic bone diseases and other bone remodeling disorders; damaged dentin, periodontal and/or cementum tissue as may result from disease or mechanical injury; and in the replacement of damaged tissue as a result of inflammation and/or chronic inflammatory disease.

As provided herein, morphogenically active fragments of OP-3 are provided to a tissue-specific locus in vivo, to induce the developmental cascade of tissue morphogenesis at that site. Cells stimulated ex vivo by contact with OP-3 also may be provided to the tissue locus. In these cases the existing tissue provides the necessary matrix requirements, providing a suitable substratum or scaffold for the proliferating and differentiating cells in a morphogenically permissive environment, as well as providing the necessary signals for directing the tissue-specificity of the developing tissue. The proteins or stimulated cells also may be combined with a formulated matrix and implanted as a device at a locus in vivo. The formulated matrix should be a biocompatible, preferably biodegradable acellular matrix having the characteristics described below. Where the necessary signals for directing the tissue-specificity of the developing tissue are not provided endogenously, the matrix preferably also is tissue-specific.

In another aspect, the members of the morphogen protein family also can control the body's cellular and humoral inflammatory response to a foreign object or an initial tissue injury. In many instances, the loss of tissue function results from the tissue destructive effects and the subsequent formation of scar tissue associated with the body's immune/inflammatory response to an initial or repeated injury to the tissue. The degree of scar tissue formation generally depends on the regenerative properties of the injured tissue, and on the degree and type of tissue damage. Thus; in another aspect, morphogenically active fragments of OP-3 may be used to prevent or to substantially inhibit the formation of scar tissue, including alleviating immune response-mediated tissue damage, by providing OP-3 or cells stimulated by exposure to OP-3 protein, to a newly injured tissue locus. The OP-3 protein also may be provided as a prophylactic, provided to a site in anticipation of tissue injury, such as part of a surgical or other clinical procedure likely to produce tissue damage, and to induce an inflammatory/immune response. In a particularly useful embodiment, OP-3 may be used as part of a transplant procedure, to enhance the tissue viability of the organ and/or tissue to be transplanted. The morphogen may be provided to the organ and/or tissue to be transplanted prior to harvest, during its transport, and/or during transplantation into the recipient host as described below.

OP-3 also may be used to increase or regenerate a mesenchymal progenitor or stem cell population in a mammal. For example, progenitor cells may be isolated from an individual's bone marrow, stimulated ex vivo with morphogenic OP-3 for a time and at a concentration sufficient to induce the cells to proliferate, and returned to the bone marrow. Other sources of progenitor cells that may be suitable include biocompatible cells obtained from a cultured cell line, stimulated in culture, and subsequently provided to the body. Alternatively, OP-3 may be provided by systemic (e.g., oral or parenteral) administration, or it may be injected or otherwise provided to a progenitor cell population in an individual to induce its mitogenic activity in vivo. For example, a morphogenically active fragment of OP-3 may be provided to the cells in vivo, e.g., by systemic injection, to induce mitogenic activity. Similarly, a particular population of hemopoietic stem cells may be increased by exposure to OP-3, for example by perfusing (plasmaphoresing) an individual's blood to extract the cells of interest, stimulating these cells ex vivo, and returning the stimulated cells to the blood.

It is anticipated that the ability to augment an individual's progenitor cell population will enhance existing methods for treating disorders resulting from a loss or reduction of a renewable cell population significantly. Two particularly significant applications include the treatment of blood disorders and diseases involving impaired or lost immune function.

The morphogens of this invention also can inhibit proliferation of epithelial cell populations. The ability to inhibit epithelial cell proliferation may be exploited to reduce tissue damage associated with psoriasis and dermatitis, and other inflammatory skin diseases, as well as ulcerative diseases of the gastrointestinal tract, such as, for example, in the healing of ulcers, including gastric ulcers, and the ulcerations induced in oral mucocitis and inflammatory bowel disease. Morphogens may be used to particular advantage as a cytoprotective agent in clinical therapies likely to effect proliferating epithelial populations, such as cancer radiotherapies and chemotherapies that typically induce oral mucositis, hair loss and/or skin disorders.

In another aspect of the invention, morphogenic OP-3 may be used to support the growth and maintenance of differentiated cells, inducing existing differentiated cells to continue expressing their phenotype. It is anticipated that this activity will be particularly useful in the treatment of tissue disorders where loss of function is caused by reduced or lost metabolic function in which cells become senescent or quiescent, such as may occur in aging cells and/or may be manifested in osteoporosis and a number of nerve degenerative diseases, including Alzheimer's disease. Application of OP-3 directly to the cells to be treated, or providing it systemically, as by oral or parenteral administration, can stimulate these cells to continue expressing their phenotype, thereby significantly reversing the effects of the dysfunction. In addition, a morphogenically active fragment of OP-3 also may be used in gene therapy protocols to stimulate the growth of quiescent cells, thereby potentially enhancing the ability of these cells to incorporate exogenous DNA.

In yet another aspect of the invention, a morphogenically active fragment of OP-3 also may be used to induce "redifferentiation" of cells that have strayed from their differentiation pathway, such as can occur during tumorgenesis. It is anticipated that this activity will be particularly useful in treatments to reduce or substantially inhibit the growth of neoplasms. The method also is anticipated to induce the de- and/or re-differentiation of these cells. As described supra, a morphogenically active OP-3 fragment may be provided to the cells directly or systemically, stimulating these cells to revert back to a morphology and phenotype characteristic of untransformed cells.

In still another aspect of the invention, OP-3 may be used to stimulate cell adhesion molecule (CAM) expression levels in a cell. CAMs are molecules defined as carrying out cell-cell interactions necessary for tissue formation. CAMs are believed to play a fundamental regulatory role in tissue development, including tissue boundary formation, embryonic induction and migration, and tissue stabilization and regeneration. Altered CAM levels have been implicated in a number of tissue disorders, including congenital defects, neoplasias, and degenerative diseases.

In particular, N-CAM expression is associated with normal neuronal cell development and differentiation, including retinal formation, synaptogenesis, and nerve-muscle tissue adhesion. Inhibition of one or more of the N-CAM isoforms is known to prevent proper tissue development. Altered N-CAM expression levels also are associated with neoplasias, including neuroblastomas (see infra), as well as with a number of neuropathies, including normal pressure hydrocephalous and type II schizophrenia. Application of the morphogen directly to the cells to be treated, or providing the morphogen to the mammal systemically, for example, parenterally, or indirectly by oral administration, may be used to induce cellular expression of one or more CAMs, particularly N-CAMs and L1.

CAMs also have been postulated as part of a morphoregulatory pathway whose activity is induced by a to date unidentified molecule (See, for example, Edelman, G. M. (1986) Ann. Rev. Cell Biol., 2:81–116). Without being limited to any given theory, the morphogens described herein may act as inducers of this pathway.

The matrices utilized in the methods of the invention may be derived from organ-specific tissue, or they may be formulated synthetically. In one embodiment of the invention, when OP-3 (or a collection of progenitor cells stimulated by OP-3) is provided at a tissue-specific locus, e.g., by systemic administration, implantation or injection at a tissue-specific locus, the existing tissue at that locus, whether diseased or damaged, has the capacity of acting as a suitable matrix or scaffold for the differentiation and proliferation of migrating progenitor cells. Alternatively, a formulated matrix may be provided externally together with the stimulated progenitor cells or morphogenically active OP-3 fragment, as may be necessary when the extent of injury sustained by the damaged tissue is large. The matrix should be a biocompatible, suitably modified acellular matrix having dimensions such that it allows the differentiation and proliferation of migratory progenitor cells, and is capable of providing a morphogenically permissive environment. The matrix also preferably allows cellular attachment and is biodegradable. Where the necessary tissue-directing signals can not be provided endogenously, the matrix preferably also is tissue-specific.

Formulated matrices may be generated from dehydrated organ-specific tissue prepared, for example, by treating the tissue with solvents to substantially remove the intracellular, non-structural components from the tissue. Alternatively, the matrix may be formulated synthetically using a biocompatible, preferably in vivo biodegradable, structural molecule, and may be formulated with suitable tissue-specific cell attachment factors. The molecule may be a naturally occurring one such as collagen, laminin or hyaluronic acid, or a synthetic polymer comprising, for example, polylactic acid, polybutyric acid, polyglycolic acid, and copolymers thereof. Currently preferred structural polymers comprise tissue-specific collagens. Currently preferred cell attachment factors include glycosaminoglycans and proteoglycans. The matrix further may be treated with an agent or agents to increase the number of pores and micropits on its surfaces, so as to enhance the influx, proliferation and differentiation of migratory progenitor cells from the body of the mammal.

The invention thus relates to compositions and methods for the use of morphogenically active fragments of OP-3, a novel species variant of the generic family of morphogens disclosed in U.S. Ser. No. 667,274, abandoned and U.S. Ser. No. 752,764, abandoned, as a tissue morphogen. Morphogenically active OP-3 and protein fragments can be isolated from naturally-occurring sources, or they may be constructed biosynthetically using conventional recombinant DNA technology. Active OP-3 useful in the compositions and methods of this invention may include forms having varying glycosylation patterns, varying N-termini and active truncated forms, e.g., produced by recombinant DNA techniques. Active OP-3 proteins also include chimeric constructs as described below, comprising both an OP-3 active domain and a non-OP-3 sequence as, for example, the pro domain and/or the N-terminal region of the mature protein. OP-3 protein can be expressed from intact or truncated cDNA or from synthetic DNAs in procaryotic or eucaryotic host cells, and purified, cleaved, refolded, and dimerized to form morphogenically active compositions. Useful host cells include procaryotes, including E. coli, and eucaryotic cells, including mammalian cells, such as CHO, COS, melanoma or BSC cells, or the insect/baculovirus system. Thus recombinant DNA techniques may be utilized to produce large quantities of OP-3 capable of inducing tissue-specific cell differentiation and tissue morphogenesis in a variety of mammals, including humans.

BRIEF DESCRIPTION OF THE DRAWINGS

FIG. 1 is a nucleotide sequence comparison of the mouse cDNA sequence of OP-2 (bases 93–1289 of SEQ ID NO:9) and OP-3 (bases 69–1265 of SEQ ID NO:1). Exon boundaries are indicated by bars beneath the sequence; diamonds indicate nucleotide differences within exons 2 and 3.

DETAILED DESCRIPTION

The invention provides a novel genetic sequence, mOP-3, encoding a novel protein, OP-3, having morphogenic properties. The genetic sequence originally was identified in a mouse cDNA library, and the invention provides methods for identifying and isolating the gene from other species. As will be appreciated by those skilled in the art, the methods described herein also may be used to isolate the OP-3 gene from other libraries, including genomic libraries. The invention also provides means for producing the OP-3 genetic sequence and the encoded protein. The invention further provides methods and compositions for inducing the developmental cascade of tissue morphogenesis in a mammal utilizing morphogenically active fragments of OP-3. The methods and compositions. provided herein may be utilized in a range of applications, including stimulating the proliferation and/or differentiation of progenitor cells and inducing the repair and regeneration of damaged tissue. The morphogenic OP-3 species of the invention are novel species variants of the family of morphogens disclosed in copending U.S. Ser. No. 667,274, U.S. Ser. No. 752,764, U.S. Ser. No. 923,780 and U.S. Ser. No. 922,813, all abandoned, the disclosures of which are incorporated hereinabove by reference. As described herein, OP-3 may be isolated from natural sources or constructed biosynthetically utilizing conventional recombinant DNA technology or constructed synthetically using standard chemical techniques.

Morphogenically active fragments of OP-3 are useful for initiating and maintaining the tissue-specific developmental cascade in a variety of tissues, including, but not limited to, bone, cartilage, dentin, neural tissue, liver, periodontal ligament, cementum, lung, heart, kidney and numerous tissues of the gastrointestinal tract. When combined with naive mesenchymal progenitor cells as disclosed herein, OP-3 can induce the proliferation and differentiation of these progenitor cells. In the presence of appropriate tissue-specific signals to direct the differentiation of these cells, and a morphogenically permissive environment, OP-3 is capable of reproducing the cascade of cellular and molecular events that occur during embryonic development to yield functional tissue. For example, the protein can induce the de novo formation of cartilage and endochondral bone, including inducing the proliferation and differentiation of progenitor cells into chondrocytes and osteoblasts, inducing appropriate mineralization and bone remodeling, inducing formation of an appropriate bone tissue vascular supply and inducing formation of differentiated bone marrow (see Example 7 below.)

Provided below is a detailed description of the nucleic acid and amino acid sequences which describe OP-3 proteins useful in the compositions and methods of this invention, including a description of how to make them, and methods and means for their therapeutic administration. Also provided are numerous, nonlimiting examples which (1) illustrate the suitability of these proteins as tissue morphogens and therapeutic agents, and (2) provide assays with which to test the morphogens encompassed by the invention in different tissues. Also provided in Example 9 is a method for screening compounds to identify morphogen stimulating agents capable of stimulating endogenous OP-3 expression and/or secretion. OP-3 stimulating agents then may be used in any of the therapeutic applications described herein in place of, or in addition to, OP-3 protein administration.

I. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogen family of proteins described herein first were identified, as well as a description of how to make, use and test them for morphogenic activity are disclosed in U.S. Ser. No. 667,274, filed Mar. 11, 1991, abandoned, and U.S. Ser. No. 752,764, filed Aug. 30, 1991, abandoned. As disclosed therein, the morphogens may be purified from naturally-sourced material or recombinantly produced from procaryotic or eucaryotic host cells, preferably as described therein. Alternatively, novel morphogenic sequences may be identified following the procedures disclosed therein.

Particularly useful morphogens identified to date include OP-1, OP-2, CBMP2A and CBMP2B (the morphogenically active domains of proteins referred to in the art as BMP2A and BMP2B, or BMP2 and BMP4, respectively), BMP3, BMP5, BMP6, Vgr-1, GDF-1, Vg1, DPP and 60A, including their allelic and species variants, as well as other mutant variants including chimeric morphogens. Detailed descriptions of the proteins may be found in, for example, U.S. Ser. No. 752,764, abandoned or U.S. Ser. No. 922,813, abandoned. Morphogenically active biosynthetic constructs such as those disclosed in U.S. Pat. No. 5,011,691, the disclosure of which is incorporated herein by reference (e.g., COP-1, COP-3, COP-4, COP-5, COP-7, and COP-16) also are envisioned to be useful.

Using the methodology disclosed in U.S. Ser. No. 752, 764, abandoned, and U.S. Ser. No. 667,274, abandoned, the novel morphogen OP-3 and its genetic sequence, now have been identified. The OP-3 proteins useful in the invention include any morphogenically active fragment of the OP-3 amino acid sequence present in Seq. ID No. 1, or allelic, species or other mutant variants thereof. The morphogenically active fragment of OP-3 also may include any morphogenically active protein encoded by part or all of the nucleic acid sequence presented in Seq. ID No. 1. The morphogenic protein also may comprise a protein encoded by part or all of a nucleic acid which hybridizes to at least part of the nucleic acid sequence encoding the "pro" region of the OP-3 protein, bases 120–848 of Seq. ID No. 1, under stringent conditions.

The mOP-3 gene encodes a protein ("mOP-3") first expressed as an immature translation product that is 399 amino acids in length. This precursor form, referred to herein as the "prepro" form, (Seq. ID. No. 1, amino acid residues 1–399) includes an N-terminal signal peptide sequence, typically less than about 20 residues, followed by a "pro" domain that is cleaved to yield the mature sequence. The "pro" form of the protein includes the pro domain and the mature domain, and forms a soluble species that appears to be the primary form secreted from cultured mammalian cells. The signal peptide is cleaved rapidly upon translation, at a cleavage site that can be predicted in a given sequence using the method of Von Heijne ((1986) *Nucleic Acids Research* 14:4683–4691). The preferred form of morphogenically active OP-3 protein comprises a processed sequence, including fragments thereof, appropriately dimerized and disulfide bonded. Where a soluble form of the protein is desired, the protein preferably comprises both the mature domain, or an active portion thereof, and part or all of the pro domain.

By amino acid sequence homology with other, known morphogens, the pro domain likely is cleaved at residues 257–260 of Seq. ID No. 1, which represent the canonical Arg-Xaa-Xaa-Arg cleavage site, to yield a mature sequence 139 amino acids in length (Seq. ID No. 1, residues 261–399). Alternatively, the pro domain may be cleaved at residues 260–263 to yield a shorter sequence 135 amino acids in length (Seq. ID No. 1, amino acid residues 264–399). All morphogens, including OP-1, OP-2 and the OP-3 proteins disclosed herein, comprise at least a conserved six cysteine skeleton in the amino acid sequence C-terminal domain and, preferably, a conserved seven cysteine skeleton (see, for example, U.S. Ser. No. 752,764, abandoned). The conserved six cysteine skeleton in mOP-3 (Seq. ID No. 1) is defined by amino acid residues 303–399; the conserved seven cysteine skeleton is defined by amino acid residues 298–399. In addition to the conserved six cysteine skeleton found in known morphogen family members including OP-1, OP-2, CBMP2A, CBMP2B, BMP3, BMP5, BMP6, Vgr-1, Vg1, 60A, DPP and GDF-1, (described, for example, in U.S. Ser. No. 752,764, abandoned, and 923,780, abandoned), the OP-3 proteins, like the OP-2 proteins, also has one additional cysteine residue (residue 338 of Seq. ID No. 1) in the conserved C-terminal domain.

The mature sequence of OP-3 shares significant amino acid sequence homology with the morphogens identified to date. Specifically, the seven cysteine fragment shows greater than 79% amino acid identity with the corresponding mOP-2 and hOP-2 sequences, and greater than 66% identity with the corresponding OP-1 sequences. Like OP-2, OP-3 has an eighth cysteine within the seven cysteine domain (e.g., at position 338 of Seq. ID No. 1). In addition, OP-3 is unique among the morphogens identified to date in that the residue at position 9 in the conserved seven cysteine domain (e.g., residue 315 of Seq. ID No. 1) is a serine, whereas other morphogens typically have a tryptophan at this location (see Table I below, and Table II in PCT/US92/07358, for example.)

Thus, useful OP-3 mutant variants include, but are not limited to, amino acid sequences derived from Seq. ID No. 1 and wherein the cysteine at position 338 is replaced with another amino acid, preferably a tyrosine, histidine, isoleucine or serine and conservative substitutions thereof, e.g., such as defined by Dayoff et al., *Atlas of Protein Sequence and Structure;* vol. 5, Suppl. 3, pp.345–362 (M. O. Dayoff, ed., Nat'l BioMed. Research Fdn., Washington D.C. 1979.). Still other useful OP-3 mutant variants include proteins wherein the serine at position 315 is replaced with another amino acid, preferably a tryptophan and conservative substitutions thereof.

Generic Sequence 7 (Seq. ID No. 12) and Generic Sequence 8 (Seq. ID No. 13) disclosed below, accommodate the homologies shared among perferred morphogen protein family members identified to date, including OP-1, OP-2, OP-3, CBMP2A, CBMP2B, BMP3, 60A, DPP, Vg1, BMP5, BMP6, Vrg-1, and GDF-1. The amino acid sequences for these proteins are described herein (see Sequence Listing and Table I below) and/or in the art, as well as in PCT publication US 92/07358, filed Aug. 28, 1992, for example. The generic sequences include both the amino acid identity shared by these sequences in the C-terminal domain, defined by the six and seven cysteine skeletons (Generic Sequences 7 and 8, respectively), as well as alternative residues for the variable positions within the sequence. The generic sequences allow for an additional cysteine at position 41 (Generic Sequence 7) or position 46 (Generic Sequence 8), providing an appropriate cysteine skeleton where inter- or intramolecular disulfide bonds can form, and containing certain critical amino acids which influence the tertiary structure of the proteins.

Generic Sequence 7

Leu Xaa Xaa Xaa Phe
1               5
Xaa Xaa Xaa Gly Trp Xaa Xaa Xaa Xaa
            10
Xaa Xaa Pro Xaa Xaa Xaa Xaa Ala
15              20
Xaa Tyr Cys Xaa Gly Xaa Cys Xaa
    25              30
Xaa Pro Xaa Xaa Xaa Xaa Xaa
            35
Xaa Xaa Xaa Asn His Ala Xaa Xaa
        40              45
Xaa Xaa Xaa Xaa Xaa Xaa Xaa Xaa
            50
Xaa Xaa Xaa Xaa Xaa Xaa Xaa Cys
55                  60

-continued
Generic Sequence 7

Cys Xaa Pro Xaa Xaa Xaa Xaa Xaa
        65
Xaa Xaa Xaa Leu Xaa Xaa Xaa
70              75
Xaa Xaa Xaa Xaa Val Xaa Leu Xaa
        80
Xaa Xaa Xaa Xaa Met Xaa Val Xaa
85                  90
Xaa Cys Xaa Cys Xaa
    95 wherein each Xaa is independently selected from a group of one or more specified amino acids defined as follows: "Res." means "residue" and Xaa at res. 2=(Tyr or Lys); Xaa at res. 3=(Val or Ile); Xaa at res. 4=(Ser. Asp or Glu); Xaa at res. 6=(Arg, Gln, Ser, Lys or Ala); Xaa at res. 7=(Asp or Glu); Xaa at res. 8=(Leu, Val or Ile); Xaa at res. 11=(Gln, Leu, Asp, His, Asn or Ser); Xaa at res. 12=(Asp, Arg, Asn or Glu); Xaa at res. 13=(Trp or Ser); Xaa at res. 14=(Ile or Val); Xaa at res. 15=(Ile or Val); Xaa at res. 16 (Ala or Ser); Xaa at res. 18=(Glu, Gln, Leu, Lys, Pro or Arg); Xaa at res. 19=(Gly or Ser); Xaa at res. 20=(Tyr or Phe); Xaa at res. 21=(Ala, Ser, Asp, Met, His, Gln, Leu or Gly); Xaa at res. 23=(Tyr, Asn or Phe); Xaa at res. 26=(Glu, His, Tyr, Asp, Gln, Ala or Ser); Xaa at res. 28=(Glu, Lys, Asp, Gln or Ala); Xaa at res. 30=(Ala, Ser, Pro, Gln, Ile or Asn); Xaa at res. 31=(Phe, Leu or Tyr); Xaa at res. 33=(Leu, Val or Met); Xaa at res. 34=(Asn, Asp, Ala, Thr or Pro); Xaa at res. 35=(Ser, Asp, Glu, Leu, Ala or Lys); Xaa at res. 36=(Tyr, Cys, His, Ser or Ile); Xaa at res. 37=(Met, Phe, Gly or Leu); Xaa at res. 38=(Asn, Ser or Lys); Xaa at res. 39=(Ala, Ser, Gly or Pro); Xaa at res. 40=(Thr, Leu or Ser); Xaa at res. 44=(Ile, Val or Thr); Xaa at res. 45=(Val, Leu, Met or Ile); Xaa at res. 46=(Gln or Arg); Xaa at res. 47=(Thr, Ala or Ser); Xaa at res. 48=(Leu or Ile); Xaa at res. 49=(Val or Met); Xaa at res. 50=(His, Asn or Arg); Xaa at res. 51=(Phe, Leu, Asn, Ser, Ala or Val); Xaa at res. 52=(Ile, Met, Asn, Ala, Val, Gly or Leu); Xaa at res. 53=(Asn, Lys, Ala, Glu, Gly or Phe); Xaa at res. 54=(Pro, Ser or Val); Xaa at res. 55=(Gilu, Asp, Asn, Gly, Val, Pro or Lys); Xaa at res. 56=(Thr, Ala, Val, Lys, Asp, Tyr, Ser, Gly, Ile or His); Xaa at res. 57=(Val, Ala or Ile); Xaa at res. 58=(Pro or Asp); Xaa at res. 59=(Lys, Leu or Glu); Xaa at res. 60=(Pro, Val or Ala); Xaa at res. 63=(Ala or Val); Xaa at res. 65=(Thr, Ala or Glu); Xaa at res. 66=(Gln, Lys, Arg or Glu); Xaa at res. 67=(Leu, Met or Val); Xaa at res. 68=(Asn, Ser, Asp or Gly); Xaa at res. 69=(Ala, Pro or Ser); Xaa at res. 70=(Ile, Thr, Val or Leu); Xaa at res. 71=(Ser, Ala or Pro); Xaa at res. 72=(Val, Leu, Met or Ile); Xaa at res. 74=(Tyr or Phe); Xaa at res. 75=(Phe, Tyr, Leu or His); Xaa at res. 76=(Asp, Asn or Leu); Xaa at res. 77=(Asp, Glu, Asn, Arg or Ser); Xaa at res. 78=(Ser, Gln, Asn, Tyr or Asp); Xaa at res. 79=(Ser, Asn, Asp, Glu or Lys); Xaa at res. 80=(Asn, Thr or Lys); Xaa at res. 82=(Ile, Val or Asn); Xaa at res. 84=(Lys or Arg); Xaa at res. 85=(Lys, Asn, Gln, His, Arg or Val); Xaa at res. 86=(Tyr, Glu or His); Xaa at res. 87=(Arg, Gln, Glu or Pro); Xaa at res. 88=(Asn, Glu, Trp or Asp); Xaa at res. 90=(Val, Thr, Ala or Ile); Xaa at res. 92=(Arg, Lys, Val, Asp, Gln or Glu); Xaa at res. 93=(Ala, Gly, Glu or Ser); Xaa at res. 95=(Gly or Ala) and Xaa at res. 97=(His or Arg).

As described above, Generic Sequence 8 (Seq. ID No. 13) includes all of Generic Sequence 7 and in addition includes the following sequence at its N-terminus:

Cys Xaa Xaa Xaa Xaa

Accordingly, beginning with residue 7, each "Xaa" in Generic Seq. 8 is a specified amino acid defined as for Generic Seq. 7, with the distinction that each residue number described for Generic Sequence 7 is shifted by five in Generic Seq. 8. Thus, "Xaa at res. 2=(Tyr or Lys)" in Gen. Seq. 7 refers to Xaa at res. 7 in Generic Seq. 8. In Generic Seq. 8, Xaa at res. 2=(Lys, Arg, Ala or Gln); Xaa at res. 3=(Lys, Arg or Met); Xaa at res. 4=(His, Arg or Gln); and Xaa at res. 5=(Glu, Ser, His, Gly, Arg, Pro, Thr, or Tyr).

Table I, set forth below, compares the C-terminal amino acid sequences defining the seven cysteine skeleton of human OP-1, mouse OP-1, human OP-2, mouse OP-2, and mouse OP-3 (mOP-3, Seq. ID No. 1). In the table, the sequences are aligned essentially following the method of Needleman et al. (1970) *J. Mol. Biol.,* 48:443–453, calculated using the Align Program (DNAstar, Inc.) In the table, three dots indicates that the amino acid in that position is the same as the amino acid in hOP-1. Three dashes indicate that no amino acid is present in that position, and are included for purposes of illustrating homologies. As is apparent from the following amino acid sequence comparisons, significant amino acid sequence homology exists between mouse OP-3 and mouse and human OP-1 and OP-2.

TABLE I

| | | | | | | | | | |
|---|---|---|---|---|---|---|---|---|---|
| hOP-1 | Cys | Lys | Lys | His | Glu | Leu | Tyr | Val | |
| mOP-1 | ... | ... | ... | ... | ... | ... | ... | ... | |
| hOP-2 | ... | Arg | Arg | ... | ... | ... | ... | ... | |
| mOP-2 | ... | Arg | Arg | ... | ... | ... | ... | ... | |
| mOP-3 | ... | Arg | Arg | ... | ... | ... | ... | ... | |
| | 1 | | | | 5 | | | | |
| hOP-1 | Ser | Phe | Arg | Asp | Leu | Gly | Trp | Gln | Asp |
| mOP-1 | ... | ... | ... | ... | ... | ... | ... | ... | ... |
| hOP-2 | ... | ... | Gln | ... | ... | ... | ... | Leu | ... |
| mOP-2 | ... | ... | ... | ... | ... | ... | ... | Leu | ... |
| mOP-3 | ... | ... | ... | ... | ... | ... | ... | Leu | ... |
| | | 10 | | | | | 15 | | |
| hOP-1 | Trp | Ile | Ile | Ala | Pro | Glu | Gly | Tyr | Ala |
| mOP-1 | ... | ... | ... | ... | ... | ... | ... | ... | ... |
| hOP-2 | ... | Val | ... | ... | ... | Gln | ... | ... | Ser |
| mOP-2 | ... | Val | ... | ... | ... | Gln | ... | ... | Ser |
| mOP-3 | Ser | Val | ... | ... | ... | Gln | ... | ... | Ser |
| | | | 20 | | | | | 25 | |
| hOP-1 | Ala | Tyr | Tyr | Cys | Glu | Gly | Glu | Cys | Ala |
| mOP-1 | ... | ... | ... | ... | ... | ... | ... | ... | ... |
| hOP-2 | ... | ... | ... | ... | ... | ... | ... | ... | Ser |
| mOP-2 | ... | ... | ... | ... | ... | ... | ... | ... | ... |
| mOP-3 | ... | ... | ... | ... | Ala | ... | ... | ... | Ile |
| | | | | | 30 | | | | 35 |
| hOP-1 | Phe | Pro | Leu | Asn | Ser | Tyr | Met | Asn | Ala |
| mOP-1 | ... | ... | ... | ... | ... | ... | ... | ... | ... |
| hOP-2 | ... | ... | ... | Asp | ... | Cys | ... | ... | ... |
| mOP-2 | ... | ... | ... | Asp | ... | Cys | ... | ... | ... |
| mOP-3 | Tyr | ... | ... | ... | ... | Cys | ... | ... | Ser |
| | | | | | | 40 | | | |
| hOP-1 | Thr | Asn | His | Ala | Ile | Val | Gln | Thr | Leu |
| mOP-1 | ... | ... | ... | ... | ... | ... | ... | ... | ... |
| hOP-2 | ... | ... | ... | ... | ... | Leu | ... | Ser | ... |
| mOP-2 | ... | ... | ... | ... | ... | Leu | ... | Ser | ... |
| mOP-3 | ... | ... | ... | ... | Thr | Met | ... | Ala | ... |
| | 45 | | | | | 50 | | | |
| hOP-1 | Val | His | Phe | Ile | Asn | Pro | Glu | Thr | Val |
| mOP-1 | ... | ... | ... | ... | ... | ... | Asp | ... | ... |
| hOP-2 | ... | ... | Leu | Met | Lys | ... | Asn | Ala | ... |
| mOP-2 | ... | ... | Leu | Met | Lys | ... | Asp | Val | ... |
| mOP-3 | ... | ... | Leu | Met | Lys | ... | Asp | Ile | Ile |
| | | 55 | | | | | 60 | | |
| hOP-1 | Pro | Lys | Pro | Cys | Cys | Ala | Pro | Thr | Gln |
| mOP-1 | ... | ... | ... | ... | ... | ... | ... | ... | ... |
| hOP-2 | ... | ... | Ala | ... | ... | ... | ... | ... | Lys |
| mOP-2 | ... | ... | Ala | ... | ... | ... | ... | ... | Lys |
| mOP-3 | ... | ... | Val | ... | ... | Val | ... | ... | Glu |
| | | | 65 | | | | | 70 | |
| hOP-1 | Leu | Asn | Ala | Ile | Ser | Val | Leu | Tyr | Phe |
| mOP-1 | ... | ... | ... | ... | ... | ... | ... | ... | ... |

TABLE I-continued

| | | | | | | | | |
|---|---|---|---|---|---|---|---|---|
| hOP-2 | ... | Ser | ... | Thr | ... | ... | ... | ... | Tyr |
| mOP-2 | ... | Ser | ... | Thr | ... | ... | ... | ... | Tyr |
| mOP-3 | ... | Ser | ... | ... | ... | Leu | ... | ... | Tyr |
| | | | | 75 | | | | | 80 |
| hOP-1 | Asp | Asp | Ser | Ser | Asn | Val | Ile | Leu | Lys |
| mOP-1 | ... | ... | ... | ... | ... | ... | ... | ... | ... |
| hOP-2 | ... | Ser | ... | Asn | ... | ... | ... | ... | Arg |
| mOP-2 | ... | Ser | ... | Asn | ... | ... | ... | ... | Arg |
| mOP-3 | ... | Arg | Asn | Asn | ... | ... | ... | ... | Arg |
| | | | | | 85 | | | | |
| hOP-1 | Lys | Tyr | Arg | Asn | Met | Val | Val | Arg | |
| mOP-1 | ... | ... | ... | ... | ... | ... | ... | ... | |
| hOP-2 | ... | His | ... | ... | ... | ... | ... | Lys | |
| mOP-2 | ... | His | ... | ... | ... | ... | ... | Lys | |
| mOP-3 | Arg | Glu | ... | ... | ... | ... | ... | Gln | |
| | 90 | | | | | | 95 | | |
| hOP-1 | Ala | Cys | Gly | Cys | His | | | | |
| mOP-1 | ... | ... | ... | ... | ... | | | | |
| hOP-2 | ... | ... | ... | ... | ... | | | | |
| mOP-2 | ... | ... | ... | ... | ... | | | | |
| mOP-3 | ... | ... | ... | ... | ... | | | | |
| | | | 100 | | | | | | |

II. Formulations and Methods for Administering OP-3 Protein as Therapeutic Agents II.A OP-3 Protein Considerations The morphogens described herein may be provided to an individual by any suitable means, preferably directly or systemically, e.g., parenterally or orally. Where the morphogen is to be provided directly (e.g., locally, as by injection, to a desired tissue site), or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (0.9% NaCl, 0.15M), pH 7–7.4. The aqueous solution containing the morphogen can be made, for example, by dissolving the protein in 50% ethanol, or acetonitrile containing 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively.

If desired, a given morphogen may be made more soluble by association with a suitable molecule. For example, association of the mature dimer with the pro domain of the morphogen increases solubility of the protein significantly. For example, the pro form of OP-3 comprises a species that is soluble in physiologically buffered solutions. In fact, the endogenous protein is thought to be transported (e.g., secreted and circulated) to particular tissues in this form. This soluble form of the protein may be obtained from the culture medium of morphogen-secreting mammalian cells. Alternatively, a soluble species may be formulated by complexing the mature dimer (or an active fragment thereof) with part or all of a pro domain. Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for oral or parenteral administration may be prepared by any of the methods well known in the pharmaceutical art, described, for example, in *Remington's Pharmaceutical Sciences,* (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen in vivo.

Other potentially useful parenteral delivery systems for these morphogens include ethylene-vinyl acetate copolymer particles, osmotic pumps, implantable infusion systems, and liposomes. Formulations for inhalation administration may contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration.

Alternatively, the morphogens described herein may be administered orally. Oral administration of proteins as therapeutics generally is not practiced as most proteins readily are degraded by digestive enzymes and acids in the mammalian digestive system before they can be absorbed into the bloodstream. However, the morphogens described herein typically are acid-stable and protease-resistant (see, for example, U.S. Pat. No. 4,968,590.) In addition, at least one morphogen, OP-1, has been identified in bovine mammary gland extract, colostrum and milk, as well as saliva. Moreover, the OP-1 purified from mammary gland extract is morphogenically active. For example, this protein induces endochondral bone formation in mammals when implanted subcutaneously in association with a suitable matrix material, using a standard in vivo bone assay, such as is disclosed in U.S. Pat. No. 4,968,590. In addition, endogenous morphogen also is detected in human serum. These findings indicate that oral and parenteral administration are viable means for administering morphogens to an individual. Moreover, while the mature forms of certain morphogens described herein typically are sparingly soluble, the morphogen form found in milk (and mammary gland extract and colostrum) is readily soluble, probably by association of the mature, morphogenically active form with the pro domain of the intact sequence and/or by association with one or more milk components. Accordingly, the compounds provided herein also may be associated with molecules capable of enhancing their solubility in vitro or in vivo, including, for example, part or all of a morphogen pro domain, and casein, as described above.

The compounds provided herein also may be associated with molecules capable of targeting the morphogen to a desired tissue. For example, tetracycline and diphosphonates (bisphosphonates) are known to bind to bone mineral, particularly at zones of bone remodeling, when they are provided systemically in a mammal. Accordingly, these molecules may be included as useful agents for targeting OP-3 to bone tissue. Alternatively, an antibody or other binding protein that interacts specifically with a surface molecule on the desired target tissue cells also may be used. Such targeting molecules further may be covalently associated to the morphogen, e.g., by chemical crosslinking, or by using standard genetic engineering means to create, for example, an acid labile bond such as an Asp-Pro linkage. Useful targeting molecules may be designed, for example, using the single chain binding site technology disclosed, for example, in U.S. Pat. No. 5,091,513.

As described above, the morphogen family members share significant sequence homology in the C-terminal active domains. By contrast, the sequences diverge significantly in the sequences which define the pro domain and the N-terminal 39 amino acids of the mature protein. Accordingly, the pro domain and/or N-terminal sequence may be morphogen-specific. As described above, it also is known that the various morphbgens identified to date are differentially expressed in the different tissues. Accordingly, without being limited to any given theory, it is likely that, under natural conditions in the body, selected morphogens typically act on a given tissue. Accordingly, part or all of morphogen-specific sequences may serve as targeting molecules for the morphogens described herein. For example, the pro domains may interact specifically with one or more molecules at the target tissue to direct the morphogen associated with the pro domain to that tissue. Thus, another useful targeting molecule for targeting OP-3 to bone tissue, for example, may include part or all of a morphogen-specific sequence, such as part or all of a pro domain and/or the N-terminus of the mature protein. Particularly useful are the morphogen-specific sequences of OP-1, BMP2 or BMP4, all of which proteins are found naturally associated with bone tissue (see, for example, U.S. Pat. No. 5,011,691). Alternatively, the morphogen-specific sequences of GDF-1 may be used to target morphogenic OP-3 to nerve tissue, particularly brain tissue where GDF-1 appears to be primarily expressed (see, for example, U.S. Ser. No. 922,813, abandoned, and Lee, *PNAS,* 88:4250–4254 (1991), incorporated herein by reference). As described above, pro forms of the proteins may be obtained from the culture medium of morphogen-secreting mammalian cells. Alternatively, a suitable species may be formulated by complexing the mature dimer (or an active fragment thereof) with part or all of a pro domain. Chimeric OP-3 proteins comprising, for example, non-OP-3 pro domains and/or non-OP-3 N-termini, may be synthesized using standard recombinant DNA methodology and/or automated chemical nucleic acid synthesis methodology well described in the art and as disclosed below.

Finally, the OP-3 proteins provided herein may be administered alone or in combination with other molecules known to have a beneficial effect on tissue morphogenesis, including molecules capable of tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration may include nerve growth factors. Other useful cofactors include symptom-alleviating cofactors, including antiseptics, antibiotics, antiviral and antifungal agents and analgesics and anesthetics.

The compounds provided herein can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition may include the morphogen dispersed in a fibrinogen-thrombin composition or other bioadhesive such as is disclosed, for example in PCT US91/09275, the disclosure of which is incorporated herein by reference. The composition then may be painted, sprayed or otherwise applied to the desired tissue surface.

The compositions can be formulated for parenteral or oral administration to humans or other mammals in therapeutically effective amounts, e.g., amounts which provide appropriate concentrations of OP-3 to target tissue for a time sufficient to induce morphogenesis, including particular steps thereof, as described above.

Where OP-3 is to be used as part of a transplant procedure, the morphogen may be provided to the living tissue or organ to be transplanted prior to removal of tissue or organ from the donor. OP-3 may be provided to the donor host directly, as by injection of a formulation comprising OP-3 into the tissue, or indirectly, e.g., by oral or parenteral administration, using any of the means described above.

Alternatively or, in addition, once removed from the donor, the organ or living tissue may be placed in a preservation solution containing OP-3. In addition, the recipient also preferably is provided with the morphogen just prior to, or concommitant with, transplantation. In all cases, OP-3 may be administered directly to the tissue at risk, as by injection to the tissue, or it may be provided systemically, either by oral or parenteral administration, using any of the methods and formulations described herein and/or known in the art.

Where OP-3 comprises part of a tissue or organ preservation solution, any commercially available preservation solution may be used to advantage. For example, useful solutions known in the art include Collins solution, Wisconsin solution, Belzer solution, Eurocollins solution and lactated Ringer's solution. Generally, an organ preservation solution usually possesses one or more of the following properties: (a) an osmotic pressure substantially equal to that of the inside of a mammalian cell,(solutions typically are hyperosmolar and have K+ and/or Mg++ ions present in an amount sufficient to produce an osmotic pressure slightly higher than the inside of a mammalian cell); (b) the solution typically is capable of maintaining substantially normal ATP levels in the cells; and (c) the solution usually allows optimum maintenance of glucose metabolism in the cells. organ preservation solutions also may contain anticoagulants, energy sources such as glucose, fructose and other sugars, metabolites, heavy metal chelators, glycerol and other materials of high viscosity to enhance survival at low temperatures, free oxygen radical inhibiting and/or scavenging agents and a pH indicator. A detailed description of preservation solutions and useful components may be found, for example, in U.S. Pat. No. 5,002,965, the disclosure of which is incorporated herein by reference.

OP-3 is envisioned to be useful in enhancing viability of any organ or living tissue to be transplanted. The morphogens may be used to particular advantage in lung, heart, liver, kidney or pancreas transplants, as well as in the transplantation and/or grafting of bone marrow, skin, gastrointestinal mucosa, and other living tissues.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of tissue loss or defect, the overall health status of the particular patient, the relative biological efficacy of the compound selected, the formulation of the compound, the presence and types of excipients in the formulation, and the route of administration. In general terms, the compounds of this invention may be provided in an aqueous physiological buffer solution containing about 0.001 to 10% w/v compound for parenteral administration. Typical dose ranges are from about 10 ng/kg to about 1 g/kg of body weight per day; a preferred dose range is from about 0.1 μg/kg to 100 mg/kg of body weight. No obvious morphogen-induced pathological lesions are induced when mature morphogen (e.g., OP-1, 20 μg) is administered daily to normal growing rats for 21 consecutive days. Moreover, 10 μg systemic injections of morphogen (e.g., OP-1) injected daily for 10 days into normal newborn mice does not produce any gross abnormalities.

II.B Matrix Preparation

A morphogenically active fragment of OP-3 may be implanted surgically, dispersed in a biocompatible, preferably in vivo biodegradable matrix appropriately modified to provide a structure or scaffold in which the OP-3 may be dispersed and which allows the differentiation and proliferation of migrating progenitor cells. The matrix also may provide signals capable of directing the tissue specificity of the differentiating cells, as well as providing a morphogenically permissive environment, being essentially free of growth inhibiting signals.

The formulated matrix may be shaped as desired in anticipation of surgery or may be shaped by the physician or technician during surgery. Thus, the material may be used in topical, subcutaneous, intraperitoneal, or intramuscular implants to repair tissue or to induce its growth de novo. The matrix preferably is biodegradable in vivo, being slowly absorbed by the body and replaced by new tissue growth, in the shape or very nearly in the shape of the implant. The matrix also may be particulate in nature.

Details of how to make and how to use the matrices useful in this invention are disclosed below and in co-pending U.S. Ser. No. 752,764, abandoned, the disclosure of which is incorporated herein by reference.

II.B(i) Tissue-Derived Matrices

Suitable biocompatible, in vivo biodegradable acellular matrices may be prepared from naturally-occurring tissue. The tissue is treated with suitable agents to substantially extract the cellular, nonstructural components of the tissue. The agents also should be capable of extracting any morphogenesis inhibiting components associated with the tissue. The resulting material is a porous, acellular matrix, substantially depleted in nonstructurally-associated components.

The matrix also may be further treated with agents that modify the matrix, increasing the number of pores and micropits on its surfaces. Those skilled in the art will know how to determine which agents are best suited to the extraction of nonstructural components for different tissues. For example, soft tissues such as liver and lung may be thin-sectioned and exposed to a nonpolar solvent such as, for example, 100% ethanol, to destroy the cellular structure of the tissue and extract nonstructural components. The material then may be dried and pulverized to yield nonadherent porous particles or it may be maintained as a gel-like solution. Structural tissues such as cartilage and dentin where collagen is a primary proteinaceous component may be demineralized and extracted with guanidinium hydrochloride, essentially following the method of Sampath et al. (1983) *PNAS* 80:6591–6595. For example, pulverized and demineralized dentin is extracted with five volumes of 4M guanidinium-HCl, 50 mM Tris-HCl, pH 7.0 for 16 hours at 4° C. The suspension then is filtered. The insoluble material that remains is collected and used to fabricate the matrix. The material is mostly collagenous in matter. It is devoid of morphogenic activity. The matrix particles may further be treated with a collagen fibril-modifying agent that extracts potentially unwanted components from the matrix, and alters the surface structure of the matrix material. Useful agents include acids, organic solvents or heated aqueous media. A detailed description of these matrix treatments are disclosed, for example, in U.S. Pat. No. 4,975,526 and PCT publication US90/00912, published Sep. 7, 1990 (WO90/10018).

The currently most preferred agent is a heated aqueous fibril-modifying medium such as water, to increase the matrix particle surface area and porosity. The currently most preferred aqueous medium is an acidic aqueous medium having a pH of less than about 4.5, e.g., within the range of about pH 2–pH 4 which may help to "swell" the collagen before heating. 0.1% acetic acid, which has a pH of about 3, currently is most preferred. 0.1M acetic acid also may be used.

Various amounts of delipidated, demineralized guanidine-extracted bone collagen are heated in the aqueous medium (1g matrix/30 ml aqueous medium) under constant stirring in a water jacketed glass flask, and maintained at a given temperature for a predetermined period of time. Preferred treatment times are about one hour, although exposure times of between about 0.5 to two hours appear acceptable. The temperature employed is held constant at a temperature within the range of about 37° C. to 65° C. The currently preferred heat treatment temperature is within the range of about 45° C. to 60° C.

After the heat treatment, the matrix is filtered, washed, lyophilized and used for implant. Where an acidic aqueous medium is used, the matrix also is preferably neutralized prior to washing and lyophilization. A currently preferred neutralization buffer is a 200 mM sodium phosphate buffer, pH 7.0. To neutralize the matrix, the matrix preferably first is allowed to cool following thermal treatment, the acidic aqueous medium (e.g., 0.1% acetic acid) then is removed and replaced with the neutralization buffer and the matrix agitated for about 30 minutes. The neutralization buffer then may be removed and the matrix washed and lyophilized.

Other useful fibril-modifying treatments include acid treatments (e.g., trifluoroacetic acid and hydrogen fluoride) and solvent treatments such as dichloromethane, acetonitrile, isopropanol and chloroform, as well as particular acid/solvent combinations.

After contact with the fibril-modifying agent, the treated matrix may be washed to remove any extracted components, following a form of the procedure set forth below:

1. Suspend matrix preparation in TBS (Tris-buffered saline) 1 g/200 ml and stir at 4° C. for 2 hrs; or in 6M urea, 50 mM Tris-HCl, 500 mM NaCl, pH 7.0 (UTBS) or water and stir at room temperature (RT) for 30 minutes (sufficient time to neutralize the pH);

2. Centrifuge and repeat wash step; and

3. Centrifuge; discard supernatant; water wash esidue; and then lyophilize.

Alternatively, suitable matrix materials may be btained commercially. For example, an extracellular atrix extract such as Matrigel™, (Collaborative Research, Inc., Bedford) derived from mouse sarcoma cells, may be used to advantage.

II.B(ii) Synthetic Matrices

In addition to the naturally-derived tissue-specific matrices described above, useful tissue-specific matrices may be formulated synthetically. These porous biocompatible, in vivo biodegradable synthetic matrices are disclosed in PCT publication US91/03603, published Dec. 12, 1991 (WO91/18558), the disclosure of which is hereby incorporated by reference. Briefly, the matrix comprises a porous crosslinked structural polymer of biocompatible, biodegradable collagen and appropriate, tissue-specific glycosaminoglycans as tissue-specific cell attachment factors. Collagen derived from a number of sources may be suitable for use in these synthetic matrices, including insoluble collagen, acid-soluble collagen, collagen soluble in neutral or basic aqueous solutions, as well as those collagens which are commercially available.

Glycosaminoglycans (GAGS) or mucopolysaccharides are hexosamine-containing polysaccharides of animal origin that have a tissue specific distribution, and therefore may be used to help determine the tissue specificity of the morphogen-stimulated differentiating cells. Reaction with the GAGs also provides collagen with another valuable property, i.e., inability to provoke an immune reaction (foreign body reaction) from an animal host.

Chemically, GAGs are made up of residues of hexosamines glycosidically bound and alternating in a more-or-less regular manner with either hexouronic acid or hexose moieties (see, e.g., Dodgson et al. in *Carbohydrate Metabolism and its Disorders* (Dickens et al., eds.) Vol. 1, Academic Press (1968)). Useful GAGs include hyaluronic acid, heparin, heparin sulfate, chondroitin 6-sulfate, chondroitin 4-sulfate, dermatan sulfate, and keratin sulfate. Other GAGs are suitable for forming the matrix described herein, and those skilled in the art will either know or be able to ascertain other suitable GAGs using no more than routine experimentation. For a more detailed description of mucopolysaccharides, see Aspinall, *Polysaccharides,* Pergamon Press, Oxford (1970). For example, as disclosed in U.S. application Ser. No. 529,852, abandoned, chondroitin-6-sulfate can be used where endochondral bone formation is desired. Heparin sulfate, on the other hand, may be used to formulate synthetic matrices for use in lung tissue repair.

Collagen can be reacted with a GAG in aqueous acidic solutions, preferably in diluted acetic acid solutions. By adding the GAG dropwise into the aqueous collagen dispersion, coprecipitates of tangled collagen fibrils coated with GAG results. This tangled mass of fibers then can be homogenized to form a homogeneous dispersion of fine fibers and then filtered and dried.

Insolubility of the collagen-GAG products can be raised to the desired degree by covalently cross-linking these materials, which also serves to raise the resistance to resorption of these materials. In general, any covalent cross-linking method suitable for cross-linking collagen also is suitable for cross-linking these composite materials, although crosslinking by a dehydrothermal process is preferred.

When dry, the crosslinked particles are essentially spherical, with diameters of about 500 $\mu$m. Scanning electron miscroscopy shows pores of about 20 $\mu$m on the surface and 40 $\mu$m on the interior. The interior is made up of both fibrous and sheet-like structures, providing surfaces for cell attachment. The voids interconnect, providing access to the cells throughout the interior of the particle. The material appears to be roughly 99.5% void volume, making the material very efficient in terms of the potential cell mass that can be grown per gram of microcarrier.

Another useful synthetic matrix is one formulated from biocompatible, in vivo biodegradable synthetic polymers, such as those composed of glycolic acid, lactic acid and/or butyric acid, including copolymers and derivatives thereof.

These polymers are well described in the art and are available commercially. For example, polymers composed of polyactic acid (e.g., MW 100 kDa), 80% polylactide/20% glycoside or poly 3-hydroxybutyric acid (e.g., MW 30 kDa) all may be purchased from PolySciences, Inc. The polymer compositions generally are obtained in particulate form. In addition, one can alter the morphology of the polymer compositions, for example to increase porosity, using any of a number of particular solvent treatments known in the art. Where the morphogen is adsorbed to the matrix surface, the steps preferably are performed under conditions which avoid hydrolysis of the polymers (e.g., non-aqueous conditions such as in an ethanol-trifluoro-acetic acid solution).

The OP-3 proteins described herein can be combined and dispersed in a suitable matrix using any of the methods described below:

1. Ethanol Precipitation

Matrix is added to the morphogen dissolved in guanidine-HCl. Samples are vortexed and incubated at a low temperature. Samples are then further vortexed. Cold absolute ethanol is added to the mixture which is then stirred and incubated. After centrifugation (microfuge, high speed) the supernatant is discarded. The matrix is washed with cold concentrated ethanol in water and then lyophilized.

2. Acetonitrile Trifluoroacetic Acid Lyophilization

In this procedure, a morphogenically active fragment of OP-3 in an acetonitrile trifluroacetic acid (ACN/TFA) solution is added to the carrier material. Samples are vigorously vortexed many times and then lyophilized.

3. Buffered Saline Lyophilization

A preparation of a morphogenically active fragment of OP-3 in physiological saline also may be vortexed with the matrix and lyophilized to produce morphogenically active material.

Tissue morphogenesis requires a morphogenically permissive environment. Clearly, in fully-functioning healthy tissue that is not composed of a permanently renewing cell population, there must exist signals to prevent continued tissue growth. Thus, it is postulated that there exists a control mechanism, such as a feedback control mechanism, which regulates the control of cell growth and differentiation. In fact, it is known that both TGF-β, and MIS are capable of inhibiting cell growth when present at appropriate concentrations. In addition, using the bone model system it can be shown that osteogenic devices comprising a bone-derived carrier (matrix) that has been demineralized and guanidine-extracted to substantially remove the noncollagenous proteins does allow endochondral bone formation when implanted in association with an osteoinductive morphogen. If, however, the bone-derived carrier is not demineralized but rather is washed only in low salt, for example, induction of endochondral bone formation is inhibited, suggesting the presence of one or more inhibiting factors within the carrier.

III. Examples

Example 1

Recombinant Production of OP-3

OP-3 proteins useful in the methods and compositions of this invention may be purified from natural sources or produced using standard recombinant methodology. General considerations for the recombinant production of morphogens are described in U.S. Ser. No. 752,764, abandoned, the disclosure of which is incorporated hereinabove by reference.

A. Identification of Novel mOP-3 Sequences

A genetic sequence encoding the morphogenic OP-3 protein was identified using a 0.3 kb EcoRI-BamHl OP-2 fragment from a mouse OP-2 cDNA as a hybridization probe, specific to the mid-pro region of OP-2 (corresponding to amino acid residues 125 to 225 of the pre-pro protein) essentially as described in U.S. Ser. No. 667,274, abandoned. The $^{32}$P-labeled probe was prepared using the random hexanucleotide priming method, and the hybridizations were performed using the following conditions: 40% formamide, 5×SSPE, 5×Denhardt's Solution, 0.1% SDS, at 37° C. overnight, and washing in 0.1×SSPE, 0.1% SDS at 50° C. Approximately 1×10$^6$ phages from a mouse cDNA (carried in lambda zapII) library made from the teratocarcinoma cell line PCC4 (Stratagene, Inc., La Jolla, Calif., cat #936301) were screened. This screening yielded four individual clones which were purified over three rounds of screening. The plasmid DNA containing the cDNAs was obtained using the lambda zapII excision process following manufacturer's directions. Three of the four clones were shown by DNA sequencing to encode OP-3. The DNA sequence, referred to herein as mOP-3 and described in Seq. ID No. 1, was identified by this procedure.

The isolated mOP-3 DNA sequence, in accordance with other known morphogens, encodes a protein comprising a "pro" region (defined essentially by residues 20–260 or 20–263 of Seq. ID No. 1) and a mature region (defined essentially by residues 261–399 or 264–399 of Seq. ID No. 1), including a functional domain comprising the conserved cysteine skeleton.

Like OP-2, OP-3 is marked by an eighth cysteine within the seven cysteine domain (e.g., at position 338 of Seq. ID No.1). The extra cysteine likely helps stabilize the folded structure, possibly by providing inter-molecular disulfide bonding. The extra cysteine also allows for heterodimer formation between OP-3 and another morphogen comprising the "eighth" cysteine, like OP-2 for example, or a modified OP-1, wherein an extra cysteine has been inserted at the appropriate location. The extra cysteine also may allow tetramer formation. The extra cysteine does not inhibit synthesis or reduce the stability of the translated sequence significantly as expressed proteins comprising the extra cysteine are readily detected by SDS gel electrophoresis. A primary glycosylation site occurs just C terminal to the extra cysteine in both OP-2 and OP-3, which may provide a protective effect.

The CDNA sequences for both human and mouse OP-2 are provided in Seq. ID Nos. 7 and 9, and the genomic sequence for human OP-2 is provided in Seq. ID No. 11 SEQ ID NO: 14 and SEQ ID: 15, wherein the exons defining the coding region of these proteins are indicated. The exon boundaries also are indicated in FIG. 1, described below. The human OP-2 locus was isolated from a genomic library (Clontech, EMBL-3 #HL1067J) on three overlapping phage clones, using standard cloning procedures. The OP-2 coding information was spread over 27 kb and, like OP-1, contains 7 exons. A comparison of exon-intron boundaries in the 7 cysteine domain showed matching locations with those of OP-1. The first OP-2 exon contains 334 bp of coding sequence (111 amino acids), including the signal peptide, and is followed by the largest intron (14.6 kb). The second exon (190 bp, 64 amino acids) is separated by a short intron (0.4 kb) from exon 3 (149 bp, 49 amino acids). It follows a large third intron of 9.5 kb. The fourth exon (195 bp, 65 amino acids) encodes the maturation site ("OP-2-Ala") and is followed by a 0.8 kb intron. The 7 cysteine domains resides on exons 5 to 7: exon 5 (80 bp, 27 amino acids) encodes the first cysteine of mature OP-2 and is followed by intron 5 (0.5 kb in length), exon 6 (111 bp, 37 amino acids) is separated by a 2.5 kb intron from the seventh, last exon with 147 bp (49 amino acids) of coding sequence. As stated above, the exon-intron boundaries are conserved between human OP-1 and OP-2, two different members of the morphogen family of proteins. By analogy, the exon-intron boundaries between human and mouse OP-2, two species variants of a morphogen, are anticipated to be conserved as well.

FIG. 1 shows the alignment of the murine OP-2 (bases 93–1289 of SEQ ID NO:9) and murine OP-3 (bases 69–1265 of SEQ ID NO:1) coding regions of the cDNA. The exon boundaries are indicated by bars beneath the sequence. Both sequences have the same number of nucleotides. The nucleotide sequence is about 80% conserved in the N-terminal and C-terminal regions. In the figure, nucleotide identity between the sequences is indicated by stippling. In addition, the central region of the sequence is highly conserved and this conserved region falls into the boundaries of exon 2 and 3. There are only three nucleotideidifferences in this region, indicated in the figure by diamonds.

The high degree of conservation in the nucleotide sequences indicates that OP-2 and OP-3 likely share the nucleotide sequence of exon 2 and 3. The different proteins may result from alternatively spliced transcripts, or they may arise from independent genes which share part of their coding sequence. Intron 1, which lies upstream of exon 2 in OP-2 (see Seq. ID No. 11 and SEQ ID NO. 14) is large (14.6 kb) and could include the start of the OP-3 gene and/or its first exon sequence. Certainly, as has been found for other mammalian genes, one or more of the introns of these morphogens may include sequences having a transcription regulatory function.

Using the screening procedure described herein and in U.S. Ser. No. 752,764, abandoned, and the labelled OP-2 fragment, or preferably a labelled OP-3 fragment, OP-3 genetic sequences from other species and other libraries may be isolated. Alternatively, or in addition, a probe to the N-terminal region of the mature protein, or the 3' noncoding region flanking and immediately following the stop codon, also may be used to screen for other OP-3 species variants. These sequences vary substantially among the morphogens and represent morphogen-specific sequences. Mammalian cell expression of OP-3 readily can be achieved using COS (simian kidney ATCC, CRL-1650) or CHO (Chinese hamster ovary) cells (e.g., CHO-DXBII, from Lawrence Chasin, Columbia University, NY). An exemplary protocol for mammalian cell expression is provided below. Other useful eukaryotic cell systems include the insect/baculovirus system or the mammalian complement system.

B. Expression of Novel OP-3 Sequences

To express the OP-3 protein, the OP-3 DNA is subcloned into an insertion site of a suitable, commercially available pUC-type vector (e.g., pUC-19, ATCC #37254, Mannassas, Va.), along with a suitable promoter/enhancer sequences and 3' termination sequences. Currently preferred promoter/enhancer sequences are the CMV promoter (human cytomegalovirus major intermediate—early promoter) and the mouse mammary tumor virus promoter (mMTV) boosted by the rous sarcoma virus LTR enhancer sequence (e.g., from Clontech, Inc., Palo Alto). Expression also may be further enhanced using transactivating enhancer sequences. The plasmid also contains DHFR as an amplifiable marker, under SV40 early promoter control (ATCC #37148). Transfection, cell culturing, gene amplification and protein expression conditions are standard conditions, well known in the art, such as are described, for example in Ausubel et al., ed., *Current Protocols in Molecular Biology*, John Wiley & Sons, NY (1989). Briefly, transfected cells are cultured in medium containing 0.1–0.5% dialyzed fetal calf serum (FCS), stably transfected high expression cell lines obtained by subcloning and evaluated by standard Northern blot. Southern blots also are used to assess the state of integrated OP-3 sequences and the extent of their copy number amplification.

Chimeric OP-3 morphogens, e.g., comprising an OP-3 active domain and, for example, part or all of a pro domain from another, different morphogen may be constructed using standard recombinant DNA technology and/or an automated DNA synthesizer to construct the desired sequence. Useful chimeras include those wherein the non-OP-3 sequence is joined to the OP-3 sequence encoding the mature OP-3 protein, and the non-OP-3 sequence encodes part or all of the sequence between the signal peptide processing site and the "Arg-Xaa-Xaa-Arg" processing sequence from at least one morphogen. Alternatively, the non-OP-3 sequence may be joined to an OP-3 sequence encoding, for example, the 6 or 7 cysteine skeletons, wherein the non-OP-3 sequence includes the sequence encoding the N-terminus of the mature protein. As will be appreciated by persons skilled in the art, the non-OP-3 sequences may be composed of sequences from one or morphogens and/or may comprise novel biosynthetic sequences.

The expressed protein then is purified as follows. For a typical 2 L preparation of transfected mammalian cells conditioned in 0.5% FCS, for example, the total protein is typically about 700 mg. The amount of OP-3 in the media, estimated by Western blot, is between about 0.1–5.0 mg. OP-3 media then is diluted in a low salt, physiologically buffered 6M urea solution, and loaded onto an S-Sepharose column, which acts as a strong cation exchanger. OP-3 binds to the column in low salt, and serum proteins are removed. The column subsequently is developed with an NaCl gradient, e.g., 0.1M NaCl–1.0M NaCl, in 6M urea, 20 mM HEPES, pH 7.0. Most contaminants are removed at the start of the gradient, and OP-3 is eluted primarily at a higher salt concentration.

The sample then is loaded onto a phenyl-Sepharose column (hydrophobic interaction chromatography). OP-3 binds phenyl-Sepharose in the presence of high concentrations of a weak chaotropic salt (e.g., 1M $(NH_4)_2SO_4$ in a physiologically buffered 6M urea solution). Once OP-3 is bound, the column is developed with a decreasing ammonium sulfate gradient, e.g., 0.6M–0.0M $(NH_4)_2SO_4$ gradient in a physiologically buffered, 6M urea solution. Again, most contaminants are removed at the start of the gradient, and OP-3 elutes primarily at low or no ammonium sulfate concentrations.

The OP-3 eluted from the phenyl-Sepharose column then is dialyzed against water, and prepared for loading onto a reverse phase chromatography column (e.g., C-18 HPLC), for example, by dialyzing against 30% acetonitrile, 0.1% TFA.

An alternative chromatography protocol is to perform the S-Sepharose chromatography in the absence of 6M urea. The bound proteins then are eluted with salt step elutions (e.g., 0.1–0.6M NaCl). Remaining OP-3 then can be eluted in the presence of 6M urea. The 6M urea elution also may be used in place of the non-urea elution to achieve maximum recovery in one step. In addition, OP-3 may be eluted from the phenyl-Sepharose column in 38% ethanol-0.01% TFA, thereby eliminating the need to dialyze the eluent before applying it to the C-18 column. Finally, multiple C-18 columns may be used (e.g., three), to further enhance purification and concentration of the protein.

OP-3 also will bind hydroxyapatite efficiently, typically in the absence of 6 M urea and at low phosphate concentrations (less than 5 mM phosphate). Bound OP-3 can be removed from the column with an elution gradient of about 0.001–0.5M step elution of phosphate in a physiologically buffered solution. Additionally, urea (6M) may be added during the elution step.

Other related chromatography methods also may be useful in purifying OP-3 from eucaryotic cell culture systems. For example, heparin-Sepharose may be used in combination with the S-Sepharose column. Alternatively, immobilized metal-ion affinity chromatography (IMAC) (e.g., $Cu^{2+}$ or $Zn^+$) and a physiologically buffered phosphate solution may be used to advantage.

Example 2

Mitogenic Effect of OP-3

2.1 Mitogenic Effect of Morphogen on Rat and Human Osteoblasts

The following example demonstrates the ability of OP-3 to induce proliferation of osteoblasts in vitro using the following assay. In this and all examples involving osteoblast cultures, rat osteoblast-enriched primary cultures preferably are used. Although these cultures are heterogeneous in that the individual cells are at different stages of differentiation, the culture is believed to more accurately reflect the metabolism and function of osteoblasts in vivo than osteoblast cultures obtained from established cell lines. Unless otherwise indicated, all chemicals referenced are standard, commercially available reagents, readily available from a number of sources, including Sigma Chemical, Co., St. Louis; Calbiochem, Corp., San Diego and Aldrich Chemical Co., Milwaukee.

Rat osteoblast-enriched primary cultures are prepared by sequential collagenase digestion of newborn suture-free rat calvaria (e.g., from 1–2 day-old animals, Long-Evans strain, Charles River Laboratories, Wilmington, Mass.), following standard procedures, such as are described, for example, in Wong et al., (1975) *PNAS* 72:3167–3171. Rat osteoblast single cell suspensions then are plated onto a multi-well plate (e.g., a 24 well plate) at a concentration of 50,000 osteoblasts per well in alpha MEM (modified Eagle's medium, Gibco, Inc., Long Island) containing 10% FBS (fetal bovine serum), L-glutamine and penicillin/streptomycin. The cells are incubated for 24 hours at 37° C., at which time the growth medium is replaced with alpha MEM containing 1% FBS and the cells incubated for an additional 24 hours so that cells are in serum-deprived growth medium at the time of the experiment.

The cultured cells are divided into three groups: (1) wells which receive, for example, 0.1, 1.0, 10.0, 40 and 80.0 ng of OP-3; (2) wells which receive 0.1, 1.0, 10.0 and 40 ng of a local-acting growth factor (e.g., TGF-β); and (3) the control group, which receive no growth factors. The cells then are incubated for an additional 18 hours after which the wells are pulsed with 2 μCi/well of $^3$H-thymidine and incubated for six more hours. The excess label then is washed off with a cold solution of 0.15M NaCl and then 250 μl of 10% tricholoracetic acid is added to each well and the wells incubated at room temperature for 30 minutes. The cells then are washed three times with cold distilled water, and lysed by the addition of 250 μl of 1% sodium dodecyl sulfate (SDS) for a period of 30 minutes at 37° C. The resulting cell lysates are harvested using standard means well known in the art, and the incorporation of $^3$H-thymidine into cellular DNA determined by liquid scintillation as an indication of mitogenic activity of the cells. In the experiment, OP-3 stimulates $^3$H-thymidine incorporation into DNA, and thus promote osteoblast cell proliferation. By contrast, the effect of TGF-β is transient and biphasic. At high concentrations, TGF-β has no significant effect on osteoblast cell proliferation.

The in vitro effect of OP-3 on osteoblast proliferation also may be evaluated using human primary osteoblasts (obtained from bone tissue of a normal adult patient and prepared as described above) and on human osteosarcoma-derived cell lines. In all cases OP-3 induces cell proliferation in accordance with the morphogen's ability to induce endochondral bone formation (see Example 7, below).

2.2 Progenitor Cell Stimulation

The following example demonstrates the ability ability of OP-3 to stimulate the proliferation of mesenchymal progenitor cells. Useful naive stem cells include pluripotential stem cells, which may be isolated from bone marrow or umbilical cord blood using conventional methodologies, (see, for example, Faradji et al., (1988) *Vox Sang.*, 55 (3):133–138 or Broxmeyer et al., (1989) *PNAS* 86:3828–3832), as well as naive stem cells obtained from blood. Alternatively, embryonic cells (e.g., from a cultured mesodermal cell line) may be useful.

Another method for obtaining progenitor cells and for determining the ability of OP-3 fragments to stimulate cell proliferation is to capture progenitor cells from an in vivo source. For example, a biocompatible matrix material able to allow the influx of migratory progenitor cells may be implanted at an in vivo site long enough to allow the influx of migratory progenitor cells. For example, a bone-derived, guanidine-extracted matrix, formulated as disclosed for example in Sampath et al. ((1983) *PNAS* 80:6591–6595), or U.S. Pat. No. 4,975,526, may be implanted into a rat at a subcutaneous site, essentially following the method of Sampath et al. After three days the implant is removed, and the progenitor cells associated with the matrix dispersed and cultured.

Progenitor cells, however obtained, then are incubated in vitro with OP-3 under standard cell culture conditions well described in the art and described hereinabove. In the absence of external stimuli, the progenitor cells do not, or only minimally, proliferate on their own in culture. However, progenitor cells cultured in the presence of a morphogenically active fragment of OP-3 do proliferate. Cell growth can be determined visually or spectrophotometrically using standard methods well known in the art.

Example 3

Morphogen-Induced Cell Differentiation 3.1 Embryonic Mesenchyme Differentiation

Morphogenically active fragments of OP-3 can be utilized to induce cell differentiation. The ability of OP-3 to induce cell differentiation can be demonstrated by culturing early mesenchymal cells in the presence of OP-3 and then studying the histology of the cultured cells by staining with toluidine blue using standard cell culturing and cell staining methodologies well described in the art. For example, it is known that rat mesenchymal cells destined to become mandibular bone, when separated from the overlying epithelial cells at stage 11 and cultured in vitro under standard tissue culture conditions, e.g., in a chemically defined, serum-free medium, containing for example, 67% DMEM (Dulbecco's modified Eagle's medium), 22% F-12 medium, 10 mM Hepes pH 7, 2 mM glutamine, 50 µg/ml transferrin, 25 µg/ml insulin, trace elements, 2 mg/ml bovine serum albumin coupled to oleic acid, with HAT (0.1 mM hypoxanthine, 10 µM aminopterin, 12 µM thymidine, will not continue to differentiate. However, if these same cells are left in contact with the overlying endoderm for an additional day, at which time they become stage 12 cells, they will continue to differentiate on their own in vitro to form chondrocytes. Further differentiation into osteoblasts and, ultimately, mandibular bone, requires an appropriate local environment, e.g., a vascularized environment.

Stage 11 mesenchymal cells, cultured in vitro in the presence of OP-3, e.g., 10–100 ng/ml, will continue to differentiate in vitro to form chondrocytes just as they continue to differentiate in vitro if they are cultured with the cell products harvested from the overlying endodermal cells. This experiment may be performed with different mesenchymal cells to demonstrate the cell differentiation capability of OP-3 in different tissues.

As another example of morphogen-induced cell differentiation, the ability of OP-3 to induce osteoblast differentiation may be demonstrated in vitro using primary osteoblast cultures, or osteoblast-like cells lines, and assaying for a variety of bone cell markers that are specific markers for the differentiated osteoblast phenotype, e.g., alkaline phosphatase activity, parathyroid hormone-mediated cyclic AMP (cAMP) production, osteocalcin synthesis, and enhanced mineralization rates.

3.2 Alkaline Phosphatase Induction of Osteoblasts by OP-3

The cultured cells in serum-free medium are incubated with, a range of OP-3 concentrations, for example, 0.1, 1.0, 10.0, 40.0 or 80.0 ng OP-3/ml medium; or with a similar range of TGF-β concentrations. 72 hours after the incubation period the cell layer is extracted with 0.5 ml of 1% Triton X-100. The resultant cell extract then, is centrifuged, and 100 pl of the extract is added to 90 µl of paranitrosophenylphosphate (PNPP)/glycerine mixture and incubated for 30 minutes in a 37° C. water bath and the reaction stopped with 100 µl NaOH. The samples then are run through a plate reader (e.g., Dynatech MR700 plate reader, and absorbance measured at 400 nm, using p-nitrophenol as a standard) to determine the presence and amount of alkaline phosphate activity. Protein concentrations are determined by the Biorad method. Alkaline phosphatase activity is calculated in units/µg protein, where 1 unit=1 nmol p-nitrophenol liberated/30 minutes at 37° C.

OP-3 alone stimulates the production of alkaline phosphatase in osteoblasts, and thus promotes the growth and expression of the osteoblast differentiated phenotype.

The long term effect of OP-3 morphogen on the production of alkaline phosphatase by rat osteoblasts also may be demonstrated as follows.

Rat osteoblasts are prepared and cultured in multi-well plates as described above. In this example six sets of 24 well plates are plated with 50,000 rat osteoblasts per well. The wells in each plate, prepared as described above, then are divided into three groups: (1) those which receive, for example, 1 ng of OP-3 per ml of medium; (2) those which receive 40 ng of OP-3 per ml of medium; and (3) those which received 80 ng of OP-3 per ml of medium. Each plate then is incubated for different lengths of time: 0 hours (control time), 24 hours, 48 hours, 96 hours, 120 hours and 144 hours. After each incubation period, the cell layer is extracted with 0.5 ml of 1% Triton X-100. The resultant cell extract is centrifuged, and alkaline phosphatase activity determined as for Example 3.1, using paranitrosophenylphosphate (PNPP). OP-3 stimulates the production of alkaline phosphatase in osteoblasts in dose-dependent manner so that increasing doses of OP-3 further increase the level of alkaline phosphatase production, and moreover, the OP-3-stimulated elevated levels of alkaline phosphatase in the treated osteoblasts is anticipated to last for an extended period of time.

3.3 OP-3 Protein Induction of PTH-Mediated cAMP.

The effect of a OP-3 on parathyroid hormone-mediated cAMP production in rat osteoblasts in vitro may be demonstrated as follows.

Rat osteoblasts are prepared and cultured in a multiwell plate as described above. The cultured cells then are divided into three groups: (1) wells which receive, for example, 1.0, 10.0 and 40.0 ng OP-3/ml medium); (2) wells which receive for example, TGF-β, at similar concentration ranges; and (3) a control group which receives no growth factors. The plate is then incubated for another 72 hours. At the end of the 72 hours the cells are treated with medium containing 0.5% bovine serum albumin (BSA) and 1 mM 3-isobutyl-1-methylxanthine for 20 minutes followed by the addition into half of the wells of human recombinant parathyroid hormone (hPTH, Sigma, St. Louis) at a concentration of 200 ng/ml for 10 minutes. The cell layer then is extracted from each well with 0.5 ml of 1% Triton X-100. The cAMP levels then are determined using a radioimmunoassay kit (e.g., Amersham, Arlington Heights, Ill.). OP-3 alone stimulates an increase in the PTH-mediated cAMP response, and thus promotes the growth and expression of the osteoblast differentiated phenotype.

3.4 OP-3 Protein Induction of Osteocalcin Production

Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to demonstrate OP-3 morphogenic efficacy in vitro.

Rat osteoblasts are prepared and cultured in a multi-well plate as above. In this experiment the medium is supplemented with 10% FBS, and on day 2, cells are fed with fresh medium supplemented with fresh 10 mM β-glycerophosphate (Sigma, Inc.). Beginning on day 5 and twice weekly thereafter, cells are fed with a complete mineralization medium containing all of the above components plus fresh L(+)-ascorbate, at a final concentration of 50 µg/ml medium. OP-3 then is added to the wells directly, e.g., in 50% acetonitrile (or 50% ethanol) containing 0.1% trifluoroacetic acid (TFA), at no more than 5 µl morphogen/ml medium. Control wells receive solvent vehicle only. The cells then are re-fed and the conditioned medium sample diluted 1:1 in standard radioimmunoassay buffer containing standard protease inhibitors and stored at −20° C. until assayed for osteocalcin. Osteocalcin synthesis is measured by standard radioimmunoassay using a commercially available osteocalcin-specific antibody.

Mineralization is determined on long term cultures (13 day) using a modified von Kossa staining technique on fixed cell layers: cells are fixed in fresh 4% paraformaldehyde at 23° C. for 10 min, following rinsing cold 0.9% NaCl. Fixed cells then are stained for endogenous alkaline phosphatase at pH 9.5 for 10 min, using a commercially available kit (Sigma, Inc.) Purple stained cells then are dehydrated with methanol and air dried. after 30 min incubation in 3% AgNO$_3$ in the dark, H$_2$O-rinsed samples are exposed for 30 sec to 254 nm UV light to develop the black silver-stained phosphate nodules. Individual mineralized foci (at least 20 μm in size) are counted under a dissecting microscope and expressed as nodules/culture.

OP-3 stimulates osteocalcin synthesis in osteoblast cultures. The increased osteocalcin synthesis in response to OP-3 is dose dependent and shows a significant increase over the basal level after 13 days of incubation. The enhanced osteocalcin synthesis also can be confirmed by detecting the elevated osteocalcin MRNA message (20-fold increase) using a rat osteocalcin-specific probe. In addition, the increase in osteoclacin synthesis correlates with increased mineralization in long term osteoblast cultures as determined by the appearance of mineral nodules. OP-3 increases the initial mineralization rate significantly compared to untreated cultures.

3.5 Morphogen-Induced CAM Expression

The morphogens described herein induce CAM expression, particularly N-CAM expression, as part of their induction of morphogenesis (see copending U.S. Ser. No. 922,813, abandoned). CAMs are morphoregulatory molecules identified in all tissues as an essential step in tissue development. N-CAMs, which comprise at least 3 isoforms (N-CAM-180, N-CAM-140 and N-CAM-120, where "180", "140" and "120" indicate the apparent molecular weights of the isoforms as measured by SDS polyacrylamide gel electrophoresis) are expressed at least transiently in developing tissues, and permanently in nerve tissue. Both the N-CAM-180 and N-CAM-140 isoforms are expressed in both developing and adult tissue. The N-CAM-120 isoform is found bnly in adult tissue. Another neural CAM is L1.

The ability of OP-3 to stimulate CAM expression can be demonstrated using the following protocol, using NG108-15 cells. NG108-15 is a transformed hybrid cell line (neuroblastoma×glioma, America Type Tissue Culture (ATCC), Manassas, Va.), exhibiting a morphology characteristic of transformed embryonic neurons. As described in Example 4, below, untreated NG108-15 cells exhibit a fibroblastic, or minimally differentiated, morphology and express only the 180 and 140 isoforms of N-CAM normally associated with a developing cell. Following morphogen treatment these cells exhibit a morphology characteristic of adult neurons and express enhanced levels of all three N-CAM isoforms.

In this example, NG108-15 cells are cultured for 4 days in the presence of increasing concentrations of OP-3 using standard culturing procedures, and standard Western blots performed on whole cell extracts. N-CAM isoforms are detected with an antibody which crossreacts with all three isoforms, mAb H28.123, obtained from Sigma Chemical Co., St. Louis, the different isoforms being distinguishable by their different mobilities on an electrophoresis gel. Control NG108-15 cells (untreated) express both the 140 kDa and the 180 kDa isoforms, but not the 120 kDa, as determined by Western blot analyses using up to 100 μg of protein. Treatment of NG108-15 cells with OP-3 results in a dose-dependent increase in the expression of the 180 kDa and 140 kDa isoforms, as well as the induction of the 120 kDa isoform induced. In addition, OP-3-induced CAM expression correlates with cell aggregation, as determined by histology.

Example 4

OP-3 Protein-Induced Redifferentiation of Transformed Phenotype

The OP-3 morphogens described herein also can induce redifferentiation of transformed cells to a morphology characteristic of untransformed cells. The examples provided below detail morphogen-induced redifferentiation of a transformed human cell line of neuronal origin (NG108-15); as well as mouse euroblastoma cells (N1E-115), and human embryo arcinoma cells, to a morphology characteristic of ntransformed cells.

As described above, NG108-15 is a transformed hybrid cell line produced by fusing neuroblastoma×glioma cells (obtained from ATTC, Manassas, Va.), and exhibiting a morphology characteristic of transformed embryonic neurons, e.g., having a fibroblastic morphology. Specifically, the cells have polygonal cell bodies, short, spike-like processes and make few contacts with neighboring cells (see copending U.S. Ser. No. 922,813, abandoned). Incubation of NG108-15 cells, cultured in a chemically defined, serum-free medium, with 0.1 to 300 ng/ml of morphogen (e.g.; OP-3) for four hours induces an orderly, dose-dependent change in cell morphology.

In the example, NG108-15 cells are subcultured on poly-L-lysine coated 6 well plates. Each well contains 40–50,000 cells in 2.5 ml of chemically defined medium. On the third day, 2.5 μl of morphogen (e.g., OP-3) in 60% ethanol containing 0.025% trifluoroacetic is added to each well. Morphogenic OP-3 of varying concentrations are tested (typically, concentration ranges of 0–300 ng/ml are tested). The media is changed daily with new aliquots of morphogen. OP-3 induces a dose-dependent redifferentiation of the transformed cells, including a rounding of the soma, an increase in phase brightness, extension of the short neurite processes, and other significant changes in the cellular ultrastructure. After several days treated cells begin to form epithelioid sheets that then become highly packed, multi-layered aggregates, as determined visually by microscopic examination.

Moreover, morphogen-induced redifferentiation occurs without any associated changes in DNA synthesis, cell division, or cell viability, making it unlikely that the morphologic changes are secondary to cell differentiation or a toxic effect of the morphogen. In addition, the morphogen-induced redifferentiation does not inhibit cell division, as determined by $^3$H-thymidine uptake, unlike other molecules which have been shown to stimulate differentiation of transformed cells, such as butyrate, DMSO, retanoic acid or Forskolin in analogous experiments. Thus, OP-3 maintains cell stability and viability after inducing redifferentiation.

The OP-3 morphogens described herein accordingly provide useful therapeutic agents for the treatment of neoplasias and neoplastic lesions of the nervous system, particularly in the treatment of neuroblastomas, including retinoblastomas, and gliomas.

As yet another, related example, the ability of OP-3 to induce the "redifferentiation" of transformed human cells may be demonstrated using the following assay. Specifically, the effect of OP-3 on human EC cells (embryo carcinoma cells, e.g., NTERA-Z CL.D1, ATCC, Manassas, Va.) may be determined. In the absence of an external stimulant, these cells can be maintained as undifferentiated stem cells, and can be induced to grow in serum free media (SFM). In the absence of treatment with a morphogen, the cells proliferate rampantly and are anchorage-independent. In the presence of morphogen, EC cells grow as flattened cells, becoming anchorage dependent and forming aggregates. In addition, growth rate is reduced approximately 10 fold. Ultimately, the cells are induced to differentiate. In the example, varying concentrations of OP-3 (e.g., 0–300 ng/ml) are added daily to cultured cells (e.g., 40–50,000 cells in 2.5 ml chemically defined medium), and the effects of treatment determined by visual examination. OP-3 stimulates redifferentiation of these cells to a morphology characteristic of untransformed embryo cells.

Example 5

Maintenance of Phenotype

Morphogenically active fragments of OP-3 also may be used to maintain a cell's differentiated phenotype. This application is particularly useful for inducing the continued expression of phenotype in senescent or quiescent cells.

5.1 In Vitro Model for Phenotypic Maintenance

The phenotypic maintenance capability of morphogens is determined readily. A number of differentiated cells become senescent or quiescent after multiple passages in vitro under standard tissue culture conditions well described in the art (e.g., Culture of Animal Cells: A Manual of Basic Techniques, C. R. Freshney, ed., Wiley, 1987). However, if these cells are cultivated in vitro in association with a morphogen such as OP-3, cells are stimulated to maintain expression of their phenotype through multiple passages. For example, the alkaline phosphatase activity of cultured osteoblasts, such as cultured osteosarcoma cells and calvaria cells, is significantly reduced after multiple passages in vitro. However, if the cells are cultivated in the presence of OP-3, alkaline phosphatase activity is maintained over extended periods of time. Similarly, phenotypic expression of myocytes also is maintained in the presence of a morphogen. In the experiment, osteoblasts are cultured as described in Example 2. The cells are divided into groups, incubated with varying concentrations of OP-3 (e.g., 0–300 ng/ml) and passaged multiple times (e.g., 3–5 times) using standard methodology. Passaged cells then are tested for alkaline phosphatase activity, as described in Example 3 as an indication of differentiated cell metabolic function. Osteoblasts cultured in the absence of OP-3 have reduced alkaline phosphatase activity, as compared to OP-3-treated cells.

5.2 In Vivo Model for Phenotypic Maintenance

Phenotypic maintenance capability also may be demonstrated in vivo, using a rat model for osteoporosis, as disclosed in the copending U.S. Ser. No. 752,857, filed Aug. 30, 1991, and U.S. Ser. No. 923,780 incorporated hereinabove. As described therein, Long Evans female rats (Charles River Laboratories, Wilmington, Mass.) are Sham-operated (control animals) or ovariectomized using standard surgical techniques, to produce an osteoporotic condition resulting from decreased estrogen production. Shortly following surgery, e.g., 200 days after ovariectomy, rats are systemically provided with phosphate buffered saline (PBS) or morphogen, (e.g., OP-3, 1–100 $\mu$g) for 21 days (e.g., by daily tail vein injection.) The rats then are sacrificed and serum alkaline phosphatase levels, serum calcium levels, and serum osteocalcin levels are determined, using standard methodologies as described therein and above. Elevated levels of osteocalcin and alkaline phosphatase are observed in the rats treated with an effective amount of OP-3. Moreover, histomorphometric analysis on the tibial diasypheal bone shows improved bone mass in OP-3-treated animals as compared with untreated, ovariectomized rats. In fact, the bone mass of OP-3-animals is comparable to (e.g., approaches) that of the sham-operated (e.g., nonovarectomized) rats.

Example 6

Proliferation of Progenitor Cell Populations

Progenitor cells may be stimulated to proliferate in vivo or ex vivo. The cells may be stimulated in vivo by injecting or otherwise providing a sterile preparation containing the morphogenically active fragment of OP-3 into the individual. For example, the hemopoietic pluripotential stem cell population of an individual may be stimulated to proliferate by injecting or otherwise providing an appropriate concentration of OP-3 to the individual's bone marrow.

Progenitor cells may be stimulated ex vivo by contacting progenitor cells of the population to be enhanced with a morphogenically active fragment of OP-3 under sterile conditions at a concentration and for a time sufficient to stimulate proliferation of the cells. Suitable concentrations and stimulation times may be determined empirically, essentially following the procedure described in Example 2, above. A morphogen concentration of between about 0.1–100 ng/ml and a stimulation period of from about 10 minutes to about 72 hours, or, more generally, about 24 hours, typically should be sufficient to stimulate a cell population of about $10^4$ to $10^6$ cells. The stimulated cells then are provided to the individual as, for example, by injecting the cells to an appropriate in vivo locus. Suitable biocompatible progenitor cells may be obtained by any of the methods known in the art or described hereinabove.

Example 7

Regeneration of Damaged or Diseased Tissue

OP-3 may be used to repair diseased or damaged mammalian tissue. The tissue to be repaired preferably is assessed first, and excess necrotic or interfering scar tissue removed as needed, e.g., by ablation or by surgical, chemical, or other methods known in the medical arts.

OP-3 then may be provided directly to the tissue locus as part of a sterile, biocompatible composition, either by surgical implantation or injection. The morphogen also may be provided systemically, as by oral or parenteral administration. Alternatively, a sterile, biocompatible composition containing progenitor cells stimulated by a morphogenically active fragment of OP-3 may be provided to the tissue locus. The existing tissue at the locus, whether diseased or damaged, provides the appropriate matrix to allow the proliferation and tissue-specific differentiation of progenitor cells. In addition, a damaged or diseased tissue locus, particularly one that has been further assaulted by surgical means, provides a morphogenically permissive environment. Systemic provision of OP-3 will be sufficient for certain applications (e.g., in the treatment of osteoporosis and other disorders of the bone remodeling cycle, as an example).

In some circumstances, particularly where tissue damage is extensive, the tissue may not be capable of providing a sufficient matrix for cell influx and proliferation. In these instances, it may be necessary to provide OP-3 or progenitor cells stimulated by OP-3 to the tissue locus in association with a suitable, biocompatible, formulated matrix, prepared by any of the means described below. The matrix preferably is in vivo biodegradable. The matrix also may be tissue-specific and/or may comprise porous particles having dimensions within the range of 70–850 $\mu$m, most preferably 150–420 $\mu$m.

OP-3 also may be used to prevent or substantially inhibit immune/inflammatory response-mediated tissue damage and scar tissue formation following an injury. OP-3 is provided to a newly injured tissue locus, to induce tissue morphogenesis at the locus, preventing the aggregation of migrating fibroblasts into non-differentiated connective tissue. OP-3 preferably is provided as a sterile pharmaceutical preparation injected into the tissue locus within five hours of the injury. Where an immune/inflammatory response is unavoidably or deliberately induced, as part of, for example, a surgical or other aggressive clinical therapy, OP-3 preferably is provided prophylactically to the patient, prior to, or concomitant with, the therapy.

Below are several examples, describing protocols for demonstrating OP-3-induced tissue morphogenesis in bone, liver, nerve, dentin, cementum and periodontal tissue.

7.1 OP-3-Induced Bone Morphogenesis

A particularly useful mammalian tissue model system for demonstrating and evaluating the morphogenic activity of a protein is the endochondral bone tissue morphogenesis model known in the art and described, for example, in U.S. Pat. No. 4,968,590 and incorporated herein by reference. The ability to induce endochondral bone formation includes the ability to induce the proliferation of progenitor cells into chondroblasts and osteoblasts, the ability to induce cartilage matrix formation, cartilage calcification, and bone remodeling, and the ability to induce formation of an appropriate vascular supply and hematopoeitic bone marrow differentiation.

The local environment in which the morphogenic material is placed is important for tissue morphogenesis. As used herein, "local environment" is understood to include the tissue structural matrix and the environment surrounding the tissue. For example, in addition to needing an appropriate anchoring substratum for their proliferation, the cells stimulated by morphogens need signals to direct the tissue-specificity of their differentiation. These signals vary for the different tissues and may include cell surface markers. In addition, vascularization of new tissue requires a local environment which supports vascularization.

The following sets forth various procedures for evaluating the in vivo morphogenic utility of OP-3 and OP-3-containing compositions. The compositions may be injected or surgically implanted in a mammal, following any of a number of procedures well known in the art. For example, surgical implant bioassays may be performed essentially following the procedure of Sampath et al. (1983) *PNAS* 80:6591–6595 and U.S. Pat. No. 4,968,590.

Histological sectioning and staining is preferred to determine the extent of morphogenesis in vivo, particularly in tissue repair procedures. Excised implants are fixed in Bouins Solution, embedded in paraffin, and cut into 6–8 $\mu$m sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include: (1) leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoclastic cells, and the commencement of bone remodeling and dissolution of the implanted matrix on days twelve to eighteen; and (8) hematopoietic bone marrow differentiation in the resulting ossicles on day twenty-one.

In addition to histological evaluation, biological markers may be used as markers for tissue morphogenesis. Useful markers include tissue-specific enzymes whose activities may be assayed (e.g., spectrophotometrically) after homogenization of the implant. These assays may be useful for quantitation and for rapidly obtaining an estimate of tissue formation after the implants are removed from the animal. For example, alkaline phosphatase activity may be used as a marker for osteogenesis.

Incorporation of systemically provided OP-3 may be followed using tagged fragments (e.g., radioactively labelled) and determining their localization in the new tissue, and/or by monitoring their disappearance from the circulatory system using a standard labeling protocol and pulse-chase procedure. OP-3 also may be provided with a tissue-specific molecular tag, whose uptake may be monitored and correlated with the concentration of OP-3 provided. As an example, ovary removal in female rats results in reduced bone alkaline phosphatase activity, and renders the rats predisposed to osteoporosis (as described in Example 5). If the female rats now are provided with OP-3, a reduction in the systemic concentration of calcium may be seen, which correlates with the presence of the provided OP-3 and which is anticipated to correspond with increased alkaline phosphatase activity.

7.2 Morphogen-Induced Liver Regeneration

As another example, a method for inducing morphogenesis of substantially injured liver tissue following a partial hepatectomy utilizing OP-3 is presented. Variations on this general protocol may be used to test morphogen activity of OP-3 in other different tissues. The general method involves excising an essentially nonregenerating portion of a tissue and providing OP-3, preferably as a soluble pharmaceutical preparation to the excised tissue locus, closing the wound, and examining the site at a future date. Like bone, liver has a potential to regenerate upon injury during post-fetal life.

OP-3, e.g., 1 mg/ml, in a biocompatible solution, for example, (e.g., a purified recombinant mature form of OP-3, is solubilized in 50% ethanol, or compatible solvent, containing 0.1% trifluoroacetic acid, or compatible acid. Alternatively, the mature protein may be solubilized by association with a pro domain. The injectable OP-3 solution is prepared, e.g., by diluting one volume of OP-3 solvent-acid stock solution with 9 volumes of 0.2% rat serum albumin in sterile PBS (phosphate-buffered saline).

In the experiment, growing rats or aged rats (e.g., Long Evans, Charles River Laboratories, Wilmington) are anesthetized by using ketamine. Two of the liver lobes (left and right) are cut out (approximately ⅓ of the lobe) and the OP-3 is injected locally at multiple sites along the cut ends. The amount of OP-3 injected may be, e.g., 100 $\mu$g in 1000 $\mu$l of PBS/RSA (phosphate buffered saline/rat serum albumin) injection buffer. Placebo samples are injection buffer only. In experimental essays, five rats in each group preferably are used. The wound is closed and the rats are allowed to eat normal food and drink tap water.

After 12 days, the rats are sacrificed and liver regeneration is observed visually, to evaluate the effects of the OP-3 on liver regeneration most effectively. The OP-3 fragment-injected group shows, e.g., complete liver tissue regeneration with no sign remaining of any cut in the liver. By contrast, the control group into which only PBS is injected, shows only minimal regeneration with the incision remaining in the sample. Previous experiments with other morphogens (e.g., OP-1) show these morphogens alone induce liver tissue regeneration.

7.3 Morphogen-Induced Dentin, Cementum and Periodontal Ligament Regeneration As still another example, the ability of OP-3 to induce dentinogenesis also may be demonstrated. To date, the unpredictable response of dental pulp tissue to injury is a basic clinical problem in dentistry. Cynomolgus monkeys are chosen as primate models as monkeys are presumed to be more indicative of human dental biology than models based on lower non-primate mammals.

Using standard dental surgical procedures, small areas (e.g., 2 mm) of dental pulps are surgically exposed by removing the enamel and dentin immediately above the pulp (by drilling) of sample teeth, performing a partial amputation of the coronal pulp tissue, inducing hemostasis, application of the pulp treatment, and sealing and filling the cavity by standard procedures.

Pulp treatments used may include: a morphogenically active fragment of OP-3 dispersed in a carrier matrix; carrier matrix alone, and no treatment. Twelve teeth per animal (four for each treatment) are prepared, and two animals are used. At four weeks, teeth are extracted and processed histologically for analysis of dentin formation, and/or ground to analyze dentin mineralization. The effect of OP-3 on osteodentin reparation may be observed visually by comparing control samples treatment (PBS) with OP-3. OP-3 plus a carrier matrix induces formation of reparative or osteodentin bridges on surgically exposed healthy dental pulps. By contrast, pulps treated with carrier matrix alone, do not form reparative dentin.

Similarly, implanting demineralized teeth and OP-3 into surgically prepared canine tooth sockets stimulates new periodontal tissue formation, including new cementum and periodontal ligament, as well as new alveolar bone and dentin tissue, as described for OP-1 in U.S. Ser. No. 07/945, 285, filed on even date herewith, abandoned, the disclosure of which is incorporated herein by reference. By contrast, untreated teeth or teeth treated with carrier vehicle alone do not induce periodontal tissue growth.

7.4 Morphogen-Induced Nerve Tissue Repair

As yet another example, the induction of regenerative effects on central nervous system (CNS) repair, by a morphogenically active fragment of OP-3, may be demonstrated using a rat brain stab model. Details of the protocol are described in copending U.S. Ser. No. 922,813, abandoned. Briefly, male Long Evans rats are anesthetized and the head area prepared for surgery. The calvariae is exposed using standard surgical procedures and a hole drilled toward the center of each lobe using a 0.035K wire, just piercing the calvariae. 25 µl solutions containing either morphogen (e.g., OP-3, 25 µg) or PBS then is provided to each of the holes by Hamilton syringe. Solutions are delivered to a depth approximately 3 mm below the surface, into the underlying cortex, corpus callosum and hippocampus. The skin then is sutured and the animal allowed to recover.

Three days post surgery, rats are sacrificed by decapitation and their brains processed for sectioning. Scar tissue formation is evaluated by immunofluoresence staining for glial fibrillary acidic protein, a marker protein for glial scarring, to qualitatively determine the degree of scar formation. Sections also are probed with OP-3-specific antibody to determine the presence of the protein. Reduced levels of glial fibrillary acidic protein are observed in the tissue sections of animals treated with OP-3, evidencing the ability of the morphogen to inhibit glial scar formation, thereby stimulating nerve regeneration.

The ability of OP-3 to stimulate peripheral nervous system axonal growth over extended distances may be demonstrated using the following model. Neurons of the peripheral nervous system can sprout new processes on their own following injury, but without guidance these sproutings typically fail to connect appropriately and die. Where the break is extensive, e.g., greater than 5 or 10 mm, regeneration is poor or nonexistent. Previous experiments with other morphogens, e.g., OP-1, show that morphogens stimulate peripheral nervous system axonal growth over extended distances, allowing repair and regeneration of damaged peripheral neural pathways.

In this example OP-3 stimulation of nerve regeneration is demonstrated using the rat sciatic nerve model. The rat sciatic nerve can regenerate spontaneously across a 5 mm gap, and occasionally across a 10 mm gap, provided that the severed ends are inserted in a saline-filled nerve guidance channel. In this experiment, nerve regeneration across at least a 12 mm gap is tested.

Adult female Sprague-Dawley rats (Charles River Laboratories, Inc.) weighing 230–250 g are anesthetized with intraperitoneal injections of sodium pentobarbital (35 mg/kg body weight). A skin incision is made parallel and just posterior to the femur. The avascular intermuscular plane between vastus lateralis and hamstring muscles are entered and followed to the loose fibroareolar tissue surrounding the sciatic nerve. The loose tissue is divided longitudinally thereby freeing the sciatic nerve over its full extent without devascularizing any portion. Under a surgical microscope the sciatic nerves are transected with -microscissors at mid-thigh and grafted with a OP-3 gel graft that separates the nerve stumps by 12 mm. The graft region is encased in a silicone tube 20 mm in length with a 1.5 mm inner diameter, the interior of which is filled with the morphogen solution. Specifically, the central 12 mm of the tube consists of an OP-3 gel prepared by mixing 1 to 5 µg of substantially pure recombinantly produced OP-3protein with approximately 100 µl of MATRIGEL™ (from Collaborative Research, Inc., Bedford, Mass.), an extracellular matrix extract derived from mouse sarcoma tissue, and containing solubilized tissue basement membrane, including laminin, type IV collagen, heparin sulfate, proteoglycan and entactin, in phosphate-buffered saline. The morphogen-filled tube then is implanted directly into the defect site, allowing 4 mm on each end to insert the nerve stumps. Each stump is abutted against the morphogen gel and is secured in the silicone tube by three stitches of commercially available surgical 10-0 nylon through the epineurium, the fascicle protective sheath.

In addition to OP-3 gel grafts, control grafts of empty silicone tubes, silicone tubes filled with gel only and "reverse" autografts, wherein 12 mm transected segments of the animal's sciatic nerve are rotated 180° prior to suturing, preferably also are grafted. All experiments preferably are performed in quadruplicate. All wounds preferably are closed by wound clips that are removed after 10 days. Rats can be grafted on both legs. At 3 weeks the animals are sacrificed, and the grafted segments removed and frozen on dry ice immediately. Frozen sections then are cut throughout the graft site, and examined for axonal regeneration by immunofluorescent staining using anti-neurofilament antibodies labeled with flurocein (obtained, for example, from Sigma Chemical Co., St. Louis).

Regeneration of the sciatic nerve occurs across the entire 12 mm distance in all graft sites wherein the gap is filled with the OP-3 gel. By contrast, empty silicone tubes, gel alone and reverse autografts do not show nerve regeneration.

Example 8

Identification of Morphogen-Expressing Tissue

Determining the tissue distribution of morphogens may be used to identify different morphogens expressed in a given tissue, as well as to identify new, related morphogens. Tissue distribution also may be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific probes.

Any probe capable of hybridizing specifically to a transcript, and distinguishing the transcript of interest from other, related transcripts may be used. Because the morphogens described herein share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful OP-3-specific probe sequence is one derived from a portion of the 3' untranslated sequence, e.g., nucleotides 1310–1674 of Seq. ID No. 1, which shares little or no homology with other morphogen sequences, including OP-2. The chosen fragment then is labelled using standard means well known and described in the art.

Using these morphogen-specific probes, which may be synthetically engineered or obtained from cloned sequences, morphogen transcripts can be identified in mammalian tissue, using standard methodologies well known to those having ordinary skill in the art. A detailed description of a suitable hybridization protocol is described in Ozkaynak, et al., (1991) Biochem. Biophys. Res. Commn. 179:116–123, and Ozkaynak, et al. (1992) (JBC, in press), the disclosures of which are incorporated herein by reference. Briefly, total RNA is prepared from various tissues (e.g., murine embryo and developing and adult liver, kidney, testis, heart, brain, thymus, stomach) by a standard methodology such as by the method of Chomczyaski et al. ((1987) Anal. Biochem 162:156–159) and described below. Poly (A)+ RNA is prepared by using oligo (dT)-cellulose chromatography (e.g., Type 7, from Pharmacia LKB Biotechnology, Inc.). Poly (A)+ RNA (generally 15 µg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5×Denhardts, 5×SSPE, and 0.1% SDS. Following hybridization, the non-specific counts are washed off the filters in 0.1×SSPE, 0.1% SDS at 50° C.

An OP-3-specific 0.5 kb probe was made from a StuI-BglII fragment of OP-3 cDNA. The fragment contains the 3' untranslated sequence from nucleotides 1310–1674, plus an additional 140 bases. The fragment was labelled using standard techniques and the hybridization performed as described. To date, OP-3, like OP-2, appears to be expressed primarily in early embryonic tissue. Specifically, Northern blots of murine embryos show abundant OP-3 expression in 8-day embryos, demonstrated by a strong band at 2.9 kb and a weaker band at 2.3 kb.

Example 9

Screening Assay for Candidate Compounds which Alter Endogenous Morphogen Levels

Candidate compound(s) which may be administered to affect the level of endogenous OP-3 morphogen may be found using the following screening assay, in which the level of OP-3 production by a cell type which produces measurable levels of the morphogen is determined with and without incubating the cell in culture with the compound, in order to assess the effects of the compound on the cell. This can be accomplished by detection of the morphogen either at the protein or RNA level. A detailed description also may be found in U.S. Ser. No. 752,861, abandoned, and U.S. Ser. No. 938,021, abandoned, incorporated hereinabove by reference.

9.1 Growth of Cells in Culture

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production includes culture supernatants or cell lysates, collected periodically and evaluated for morphogen production by immunoblot analysis (Sambrook et al., eds., 1989, Molecular Cloning, Cold Spring Harbor Press, Cold Spring Harbor, N.Y.), or a portion of the cell culture itself, collected periodically and used to prepare polyA+ RNA for RNA analysis. To monitor de novo morphogen synthesis, some cultures are labeled according to conventional procedures with an $^{35}$S-methionine/$^{35}$S-cysteine mixture for 6–24 hours and then evaluated for morphogenic protein synthesis by conventional immunoprecipitation methods.

9.2 Determination of Level of Morphogenic Protein

In order to quantitate the production of a morphogenic protein, e.g., OP-3, by a cell type, an immunoassay may be performed to detect the morphogen using a polyclonal or monoclonal antibody specific for that protein. For example, OP-3 may be detected using a polyclonal antibody specific for OP-3 in an ELISA, as follows.

1 µg/100 µl of affinity-purified polyclonal rabbit IgG specific for OP-3 is added to each well of a 96-well plate and incubated at 37° C. for an hour. The wells are washed four times with 0.167M sodium borate buffer with 0.15M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 µl aliquot of an appropriate dilution of each of the test samples of cell culture supernatant is added to each well in triplicate and incubated at 37° C. for 30 min. After incubation, 100 μl biotinylated rabbit anti-OP-3 serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 μl strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 μl substrate (ELISA Amplification System Kit, Life Technologies, Inc., Bethesda, Md.) is added to each well incubated at room temperature for 15 min. Then, 50 μl amplifier (from the same amplification system kit) is added and incubated for another 15 min at room temperature. The reaction is stopped by the addition of 50 μl 0.3M sulphuric acid. The OD at 490 nm of the solution in each well is recorded. To quantitate OP-3 in culture media, an OP-3 standard curve is performed in parallel with the test samples.

Polyclonal antibody may be prepared as follows. Each rabbit is given a primary immunization of 100 ug/500 μl recombinantly-produced OP-3 protein or protein fragment in 0.1% SDS mixed with 500 μl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-3 is detected in the serum using an ELISA assay. Then, the rabbit is boosted monthly with 100 μg of antigen and bled (15 ml per bleed) at days seven and ten after boosting.

Monoclonal antibody specific for a given morphogen may be prepared as follows. A mouse is given two injections of OP-3 protein or a protein fragment specific for OP-3. The protein preferably is recombinantly produced. The first injection contains 100 μg of OP-3 in complete Freund's adjuvant and is given subcutaneously. The second injection contains 50 μg of OP-3 in incomplete adjuvant and is given intraperitoneally. The mouse then receives a total of 230 μg of OP-3 in four intraperitoneal injections at various times over an eight month period. One week prior to fusion, the mouse is boosted intraperitoneally with OP-3 (e.g., 100 μg) and may be additionally boosted with an OP-3-specific peptide (e.g., corresponding to the N-terminus of the mature protein) conjugated to bovine serum albumin with a suitable crosslinking agent. This boost can be repeated five days (IP), four days (IP), three days (IP) and one day (IV) prior to fusion. The mouse spleen cells then are fused to commercially available myeloma cells at a ratio of 1:1 using PEG 1500 (Boeringer Mannheim, Germany), and the fused cells plated and screened for OP-3-specific antibodies using OP-3 as antigen. The cell fusion and monoclonal screening steps readily are performed according to standard procedures well described in standard texts widely available in the art.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An in vitro or ex vivo composition comprising a progenitor cell population isolated from a renewable or conditionally renewable tissue and at least a fragment of OP-3, wherein said fragment induces endochondral bone formation in an in vivo assay.

2. The composition of claim 1, wherein said fragment comprises amino acids 303 to 399 of SEQ ID NO: 1 or a conservative variant thereof.

3. The composition of claim 2 wherein said fragment has an amino acid substitution for the serine at position 315 or the cysteine at position 338 in SEQ ID NO: 1.

4. The composition of claim 2, wherein said fragment comprises amino acids 298 to 399 of SEQ ID NO: 1 or a conservative variant thereof.

5. The composition of claim 4, wherein said fragment comprises amino acids 264 to 399 of SEQ ID NO: 1 or a conservative variant thereof.

6. The composition of claim 5, wherein said fragment comprises amino acids 261 to 399 of SEQ ID NO: 1 or a conservative variant thereof.

7. The composition of claim 6, wherein said fragment comprises amino acids 18 to 399 of SEQ ID NO:1 or a conservative variant thereof.

8. The composition of claim 7, wherein said fragment comprises amino acids 1 to 399 of SEQ ID NO: 1 or a conservative variant thereof.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 1674 base pairs
( B ) TYPE: nucleic acid
( C ) STRANDEDNESS: single
( D ) TOPOLOGY: linear ( i i ) MOLECULE TYPE:

( i x ) FEATURE:
( A ) NAME/KEY: CDS
( B ) LOCATION: 69..1265
( D ) OTHER INFORMATION: /note= "mOP3-PP"

( x i ) SEQUENCE DESCRIPTION: SEQ ID NO:1:

```
GGATCCGCGG  CGCTGTCCCA  TCCTTGTCGT  CGAGGCGTCG  CTGGATGCGA  GTCCGCTAAA           60

CGTCCGAG  ATG  GCT  GCG  CGT  CCG  GGA  CTC  CTA  TGG  CTA  CTG  GGC  CTG  GCT    110
          Met  Ala  Ala  Arg  Pro  Gly  Leu  Leu  Trp  Leu  Leu  Gly  Leu  Ala
           1                5                         10

CTG  TGC  GTG  TTG  GGC  GGC  GGT  CAC  CTC  TCG  CAT  CCC  CCG  CAC  GTC  TTT    158
Leu  Cys  Val  Leu  Gly  Gly  Gly  His  Leu  Ser  His  Pro  Pro  His  Val  Phe
 15                      20                      25                      30
```

| | | | | | | | | | | | | | | | | |
|---|---|---|---|---|---|---|---|---|---|---|---|---|---|---|---|---|
| CCC | CAG | CGT | CGA | CTA | GGA | GTA | CGC | GAG | CCC | CGC | GAC | ATG | CAG | CGC | GAG | 206 |
| Pro | Gln | Arg | Arg | Leu 35 | Gly | Val | Arg | Glu 40 | Pro | Arg | Asp | Met | Gln | Arg 45 | Glu | |
| ATT | CGG | GAG | GTG | CTG | GGG | CTA | GCC | GGG | CGG | CCC | CGA | TCC | CGA | GCA | CCG | 254 |
| Ile | Arg | Glu | Val | Leu 50 | Gly | Leu | Ala | Gly 55 | Arg | Pro | Arg | Ser | Arg 60 | Ala | Pro | |
| GTC | GGG | GCT | GCC | CAG | CAG | CCA | GCG | TCT | GCG | CCC | CTC | TTT | ATG | TTG | GAC | 302 |
| Val | Gly | Ala | Ala | Gln 65 | Gln | Pro | Ala | Ser 70 | Ala | Pro | Leu | Phe | Met 75 | Leu | Asp | |
| CTG | TAC | CGT | GCC | ATG | ACG | GAT | GAC | AGT | GGC | GGT | GGG | ACC | CCG | CAG | CCT | 350 |
| Leu | Tyr 80 | Arg | Ala | Met | Thr | Asp 85 | Asp | Ser | Gly | Gly | Gly 90 | Thr | Pro | Gln | Pro | |
| CAC | TTG | GAC | CGT | GCT | GAC | CTG | ATT | ATG | AGC | TTT | GTC | AAC | ATA | GTG | GAA | 398 |
| His 95 | Leu | Asp | Arg | Ala | Asp 100 | Leu | Ile | Met | Ser | Phe 105 | Val | Asn | Ile | Val | Glu 110 | |
| CGC | GAC | CGT | ACC | CTG | GGC | TAC | CAG | GAG | CCA | CAC | TGG | AAG | GAA | TTC | CAC | 446 |
| Arg | Asp | Arg | Thr | Leu 115 | Gly | Tyr | Gln | Glu 120 | Pro | His | Trp | Lys | Glu | Phe 125 | His | |
| TTT | GAC | CTA | ACC | CAG | ATC | CCT | GCT | GGG | GAG | GCT | GTC | ACA | GCT | GCT | GAG | 494 |
| Phe | Asp | Leu | Thr 130 | Gln | Ile | Pro | Ala | Gly 135 | Glu | Ala | Val | Thr | Ala 140 | Ala | Glu | |
| TTC | CGG | ATC | TAC | AAA | GAA | CCC | AGT | ACC | CAC | CCG | CTC | AAC | ACA | ACC | CTC | 542 |
| Phe | Arg | Ile | Tyr 145 | Lys | Glu | Pro | Ser | His 150 | His | Pro | Leu | Asn | Thr 155 | Thr | Leu | |
| CAC | ATC | AGC | ATG | TTC | GAA | GTG | GTC | CAA | GAG | CAC | TCC | AAC | AGG | GAG | TCT | 590 |
| His | Ile | Ser | Met 160 | Phe | Glu | Val | Val | Gln 165 | Glu | His | Ser | Asn | Arg 170 | Glu | Ser | |
| GAC | TTG | TTC | TTT | TTG | GAT | CTT | CAG | ACG | CTC | CGA | TCT | GGG | GAC | GAG | GGC | 638 |
| Asp 175 | Leu | Phe | Phe | Leu | Asp 180 | Leu | Gln | Thr | Leu | Arg 185 | Ser | Gly | Asp | Glu | Gly 190 | |
| TGG | CTG | GTG | CTG | GAC | ATC | ACA | GCA | GCC | AGT | GAC | CGA | TGG | CTG | CTG | AAC | 686 |
| Trp | Leu | Val | Leu | Asp 195 | Ile | Thr | Ala | Ala | Ser 200 | Asp | Arg | Trp | Leu | Leu 205 | Asn | |
| CAT | CAC | AAG | GAC | CTA | GGA | CTC | CGC | CTC | TAT | GTG | GAA | ACC | GAG | GAT | GGG | 734 |
| His | His | Lys | Asp 210 | Leu | Gly | Leu | Arg | Leu 215 | Tyr | Val | Glu | Thr | Glu 220 | Asp | Gly | |
| CAC | AGC | ATA | GAT | CCT | GGC | CTA | GCT | GGT | CTG | CTT | GGA | CGA | CAA | GCA | CCA | 782 |
| His | Ser | Ile | Asp 225 | Pro | Gly | Leu | Ala | Gly 230 | Leu | Leu | Gly | Arg | Gln 235 | Ala | Pro | |
| CGC | TCC | AGA | CAG | CCT | TTC | ATG | GTT | GGT | TTC | TTC | AGG | GCC | AAC | CAG | AGT | 830 |
| Arg | Ser | Arg | Gln 240 | Pro | Phe | Met | Val | Gly 245 | Phe | Phe | Arg | Ala | Asn 250 | Gln | Ser | |
| CCT | GTG | CGG | GCC | CCT | CGA | ACA | GCA | AGA | CCA | CTG | AAG | AAG | AAG | CAG | CTA | 878 |
| Pro 255 | Val | Arg | Ala | Pro | Arg 260 | Thr | Ala | Arg | Pro | Leu 265 | Lys | Lys | Lys | Gln | Leu 270 | |
| AAT | CAA | ATC | AAC | CAG | CTG | CCG | CAC | TCC | AAC | AAA | CAC | CTA | GGA | ATC | CTT | 926 |
| Asn | Gln | Ile | Asn | Gln 275 | Leu | Pro | His | Ser | Asn 280 | Lys | His | Leu | Gly | Ile 285 | Leu | |
| GAT | GAT | GGC | CAC | GGT | TCT | CAC | GGC | AGA | GAA | GTT | TGC | CGC | AGG | CAT | GAG | 974 |
| Asp | Asp | Gly | His 290 | Gly | Ser | His | Gly | Arg 295 | Glu | Val | Cys | Arg | Arg 300 | His | Glu | |
| CTC | TAT | GTC | AGC | TTC | CGT | GAC | CTT | GGC | TGG | CTG | GAC | TCT | GTC | ATT | GCC | 1022 |
| Leu | Tyr | Val | Ser 305 | Phe | Arg | Asp | Leu | Gly 310 | Trp | Leu | Asp | Ser | Val 315 | Ile | Ala | |
| CCC | CAG | GGC | TAC | TCC | GCC | TAT | TAC | TGT | GCT | GGG | GAG | TGC | ATC | TAC | CCA | 1070 |
| Pro | Gln | Gly | Tyr 320 | Ser | Ala | Tyr | Tyr | Cys 325 | Ala | Gly | Glu | Cys | Ile 330 | Tyr | Pro | |
| CTG | AAC | TCC | TGT | ATG | AAC | TCC | ACC | AAC | CAC | GCC | ACT | ATG | CAG | GCC | CTG | 1118 |
| Leu | Asn | Ser | Cys | Met 335 | Asn | Ser | Thr | Asn | His 340 | Ala | Thr | Met | Gln | Ala 345 | Leu 350 | |

| | | | | | | | | | | | | | | | | |
|---|---|---|---|---|---|---|---|---|---|---|---|---|---|---|---|---|
| GTA | CAT | CTG | ATG | AAG | CCA | GAT | ATC | ATC | CCC | AAG | GTG | TGC | TGT | GTG | CCT | 1166 |
| Val | His | Leu | Met | Lys | Pro | Asp | Ile | Ile | Pro | Lys | Val | Cys | Cys | Val | Pro | |
| | | | 355 | | | | | 360 | | | | | | 365 | | |
| ACT | GAG | CTG | AGT | GCC | ATT | TCT | CTG | CTC | TAC | TAT | GAT | AGA | AAC | AAT | AAT | 1214 |
| Thr | Glu | Leu | Ser | Ala | Ile | Ser | Leu | Leu | Tyr | Tyr | Asp | Arg | Asn | Asn | Asn | |
| | | | 370 | | | | 375 | | | | | | 380 | | | |
| GTC | ATC | CTG | CGC | AGG | GAG | CGC | AAC | ATG | GTA | GTC | CAG | GCC | TGT | GGC | TGC | 1262 |
| Val | Ile | Leu | Arg | Arg | Glu | Arg | Asn | Met | Val | Val | Gln | Ala | Cys | Gly | Cys | |
| | | | 385 | | | | | 390 | | | | | 395 | | | |

| | | | | |
|---|---|---|---|---|
| CAC | TGAGTCCCTG | CCCAACAGCC | TGCTGCCATC | CCATCTATCT | AGTCAGGCCT | 1315 |
| His | | | | | |
| CTCTTCCAAG | GCAGGAAACC | AACAAGAGG | GAAGGCAGTG | CTTTCAACTC | CATGTCCACA | 1375 |
| TTCACAGTCT | TGGCCCTCTC | TGTTCTTTTT | GCCAAGGCTG | AGAAGATGGT | CCTAGTTATA | 1435 |
| ACCCTGGTGA | CCTCAGTAGC | CCGATCTCTC | ATCTCCCCAA | ACTCCCAAT | GCAGCCAGGG | 1495 |
| GCATCTATGT | CCTTTGGGAT | TGGGCACAGA | AGTCCAATTT | ACCAACTTAT | TCATGAGTCA | 1555 |
| CTACTGGCCC | AGCCTGGACT | TGAACCTGGA | ACACAGGGTA | GAGCTCAGGC | TCTTCAGTAT | 1615 |
| CCATCAGAAG | ATTTAGGTGT | GTGCAGACAT | GACCACACTC | CCCCTAGCAC | TCCATAGCC | 1674 |

( 2 ) INFORMATION FOR SEQ ID NO:2:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Ala | Arg | Pro | Gly | Leu | Leu | Trp | Leu | Leu | Gly | Leu | Ala | Leu | Cys |
| 1 | | | | 5 | | | | 10 | | | | | | 15 | |
| Val | Leu | Gly | Gly | Gly | His | Leu | Ser | His | Pro | Pro | His | Val | Phe | Pro | Gln |
| | | | 20 | | | | 25 | | | | 30 | | | | |
| Arg | Arg | Leu | Gly | Val | Arg | Glu | Pro | Arg | Asp | Met | Gln | Arg | Glu | Ile | Arg |
| | | | 35 | | | | 40 | | | | 45 | | | | |
| Glu | Val | Leu | Gly | Leu | Ala | Gly | Arg | Pro | Arg | Ser | Arg | Ala | Pro | Val | Gly |
| | 50 | | | | 55 | | | | | 60 | | | | | |
| Ala | Ala | Gln | Gln | Pro | Ala | Ser | Ala | Pro | Leu | Phe | Met | Leu | Asp | Leu | Tyr |
| 65 | | | | 70 | | | | 75 | | | | | | 80 | |
| Arg | Ala | Met | Thr | Asp | Asp | Ser | Gly | Gly | Thr | Pro | Gln | Pro | His | Leu | |
| | | | 85 | | | | 90 | | | | | 95 | | | |
| Asp | Arg | Ala | Asp | Leu | Ile | Met | Ser | Phe | Val | Asn | Ile | Val | Glu | Arg | Asp |
| | | | 100 | | | | 105 | | | | 110 | | | | |
| Arg | Thr | Leu | Gly | Tyr | Gln | Glu | Pro | His | Trp | Lys | Glu | Phe | His | Phe | Asp |
| | | 115 | | | | 120 | | | | | 125 | | | | |
| Leu | Thr | Gln | Ile | Pro | Ala | Gly | Glu | Ala | Val | Thr | Ala | Ala | Glu | Phe | Arg |
| | 130 | | | | 135 | | | | | 140 | | | | | |
| Ile | Tyr | Lys | Glu | Pro | Ser | Thr | His | Pro | Leu | Asn | Thr | Thr | Leu | His | Ile |
| 145 | | | | 150 | | | | 155 | | | | | | 160 | |
| Ser | Met | Phe | Glu | Val | Val | Gln | Glu | His | Ser | Asn | Arg | Glu | Ser | Asp | Leu |
| | | | 165 | | | | 170 | | | | | 175 | | | |
| Phe | Phe | Leu | Asp | Leu | Gln | Thr | Leu | Arg | Ser | Gly | Asp | Glu | Gly | Trp | Leu |
| | | 180 | | | | 185 | | | | | 190 | | | | |
| Val | Leu | Asp | Ile | Thr | Ala | Ala | Ser | Asp | Arg | Trp | Leu | Leu | Asn | His | His |
| | | 195 | | | | 200 | | | | | 205 | | | | |
| Lys | Asp | Leu | Gly | Leu | Arg | Leu | Tyr | Val | Glu | Thr | Glu | Asp | Gly | His | Ser |
| | 210 | | | | 215 | | | | | 220 | | | | | |

| Ile | Asp | Pro | Gly | Leu | Ala | Gly | Leu | Leu | Gly | Arg | Gln | Ala | Pro | Arg | Ser |
| 225 | | | | 230 | | | | | 235 | | | | | | 240 |

| Arg | Gln | Pro | Phe | Met | Val | Gly | Phe | Phe | Arg | Ala | Asn | Gln | Ser | Pro | Val |
| | | | | 245 | | | | | 250 | | | | | 255 | |

| Arg | Ala | Pro | Arg | Thr | Ala | Arg | Pro | Leu | Lys | Lys | Lys | Gln | Leu | Asn | Gln |
| | | | 260 | | | | | 265 | | | | | 270 | | |

| Ile | Asn | Gln | Leu | Pro | His | Ser | Asn | Lys | His | Leu | Gly | Ile | Leu | Asp | Asp |
| | | 275 | | | | | 280 | | | | | 285 | | | |

| Gly | His | Gly | Ser | His | Gly | Arg | Glu | Val | Cys | Arg | Arg | His | Glu | Leu | Tyr |
| | 290 | | | | | 295 | | | | | 300 | | | | |

| Val | Ser | Phe | Arg | Asp | Leu | Gly | Trp | Leu | Asp | Ser | Val | Ile | Ala | Pro | Gln |
| 305 | | | | | 310 | | | | | 315 | | | | | 320 |

| Gly | Tyr | Ser | Ala | Tyr | Tyr | Cys | Ala | Gly | Glu | Cys | Ile | Tyr | Pro | Leu | Asn |
| | | | | 325 | | | | | 330 | | | | | 335 | |

| Ser | Cys | Met | Asn | Ser | Thr | Asn | His | Ala | Thr | Met | Gln | Ala | Leu | Val | His |
| | | | 340 | | | | | 345 | | | | | 350 | | |

| Leu | Met | Lys | Pro | Asp | Ile | Ile | Pro | Lys | Val | Cys | Cys | Val | Pro | Thr | Glu |
| | | 355 | | | | | 360 | | | | | 365 | | | |

| Leu | Ser | Ala | Ile | Ser | Leu | Leu | Tyr | Tyr | Asp | Arg | Asn | Asn | Asn | Val | Ile |
| | 370 | | | | | 375 | | | | | 380 | | | | |

| Leu | Arg | Arg | Glu | Arg | Asn | Met | Val | Val | Gln | Ala | Cys | Gly | Cys | His | |
| 385 | | | | | 390 | | | | | 395 | | | | | |

( 2 ) INFORMATION FOR SEQ ID NO:3:

( i ) SEQUENCE CHARACTERISTICS:
        ( A ) LENGTH: 1822 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 49..1341
        ( D ) OTHER INFORMATION: /function="OSTEOGENIC PROTEIN"
            / product= "hOP1-PP"
            / note= "hOP1 cDNA"

( x i ) SEQUENCE DESCRIPTION: SEQ ID NO:3:

| GGTGCGGGCC | CGGAGCCCGG | AGCCCGGGTA | GCGCGTAGAG | CCGGCGCG | ATG | CAC | GTG | 57 |
| | | | | | Met | His | Val | |
| | | | | | 1 | | | |

| CGC | TCA | CTG | CGA | GCT | GCG | GCG | CCG | CAC | AGC | TTC | GTG | GCG | CTC | TGG | GCA | 105 |
| Arg | Ser | Leu | Arg | Ala | Ala | Ala | Pro | His | Ser | Phe | Val | Ala | Leu | Trp | Ala | |
| | 5 | | | | | 10 | | | | | 15 | | | | | |

| CCC | CTG | TTC | CTG | CTG | CGC | TCC | GCC | CTG | GCC | GAC | TTC | AGC | CTG | GAC | AAC | 153 |
| Pro | Leu | Phe | Leu | Leu | Arg | Ser | Ala | Leu | Ala | Asp | Phe | Ser | Leu | Asp | Asn | |
| 20 | | | | | 25 | | | | | 30 | | | | | 35 | |

| GAG | GTG | CAC | TCG | AGC | TTC | ATC | CAC | CGG | CGC | CTC | CGC | AGC | CAG | GAG | CGG | 201 |
| Glu | Val | His | Ser | Ser | Phe | Ile | His | Arg | Arg | Leu | Arg | Ser | Gln | Glu | Arg | |
| | | | | 40 | | | | | 45 | | | | | 50 | | |

| CGG | GAG | ATG | CAG | CGC | GAG | ATC | CTC | TCC | ATT | TTG | GGC | TTG | CCC | CAC | CGC | 249 |
| Arg | Glu | Met | Gln | Arg | Glu | Ile | Leu | Ser | Ile | Leu | Gly | Leu | Pro | His | Arg | |
| | | | 55 | | | | | 60 | | | | | 65 | | | |

| CCG | CGC | CCG | CAC | CTC | CAG | GGC | AAG | CAC | AAC | TCG | GCA | CCC | ATG | TTC | ATG | 297 |
| Pro | Arg | Pro | His | Leu | Gln | Gly | Lys | His | Asn | Ser | Ala | Pro | Met | Phe | Met | |
| | | 70 | | | | | 75 | | | | | 80 | | | | |

| CTG | GAC | CTG | TAC | AAC | GCC | ATG | GCG | GTG | GAG | GAG | GGC | GGC | GGG | CCC | GGC | 345 |
| Leu | Asp | Leu | Tyr | Asn | Ala | Met | Ala | Val | Glu | Glu | Gly | Gly | Gly | Pro | Gly | |

-continued

|  |  | 85 |  |  |  |  | 90 |  |  |  |  | 95 |  |  |  |  |
|---|---|---|---|---|---|---|---|---|---|---|---|---|---|---|---|---|
| GGC | CAG | GGC | TTC | TCC | TAC | CCC | TAC | AAG | GCC | GTC | TTC | AGT | ACC | CAG | GGC | 393 |
| Gly | Gln | Gly | Phe | Ser | Tyr | Pro | Tyr | Lys | Ala | Val | Phe | Ser | Thr | Gln | Gly |  |
| 100 |  |  |  |  | 105 |  |  |  |  | 110 |  |  |  |  | 115 |  |
| CCC | CCT | CTG | GCC | AGC | CTG | CAA | GAT | AGC | CAT | TTC | CTC | ACC | GAC | GCC | GAC | 441 |
| Pro | Pro | Leu | Ala | Ser | Leu | Gln | Asp | Ser | His | Phe | Leu | Thr | Asp | Ala | Asp |  |
|  |  |  |  | 120 |  |  |  |  | 125 |  |  |  |  | 130 |  |  |
| ATG | GTC | ATG | AGC | TTC | GTC | AAC | CTC | GTG | GAA | CAT | GAC | AAG | GAA | TTC | TTC | 489 |
| Met | Val | Met | Ser | Phe | Val | Asn | Leu | Val | Glu | His | Asp | Lys | Glu | Phe | Phe |  |
|  |  |  | 135 |  |  |  |  | 140 |  |  |  |  | 145 |  |  |  |
| CAC | CCA | CGC | TAC | CAC | CAT | CGA | GAG | TTC | CGG | TTT | GAT | CTT | TCC | AAG | ATC | 537 |
| His | Pro | Arg | Tyr | His | His | Arg | Glu | Phe | Arg | Phe | Asp | Leu | Ser | Lys | Ile |  |
|  |  | 150 |  |  |  |  | 155 |  |  |  |  | 160 |  |  |  |  |
| CCA | GAA | GGG | GAA | GCT | GTC | ACG | GCA | GCC | GAA | TTC | CGG | ATC | TAC | AAG | GAC | 585 |
| Pro | Glu | Gly | Glu | Ala | Val | Thr | Ala | Ala | Glu | Phe | Arg | Ile | Tyr | Lys | Asp |  |
| 165 |  |  |  |  | 170 |  |  |  |  | 175 |  |  |  |  |  |  |
| TAC | ATC | CGG | GAA | CGC | TTC | GAC | AAT | GAG | ACG | TTC | CGG | ATC | AGC | GTT | TAT | 633 |
| Tyr | Ile | Arg | Glu | Arg | Phe | Asp | Asn | Glu | Thr | Phe | Arg | Ile | Ser | Val | Tyr |  |
| 180 |  |  |  |  | 185 |  |  |  |  | 190 |  |  |  |  | 195 |  |
| CAG | GTG | CTC | CAG | GAG | CAC | TTG | GGC | AGG | GAA | TCG | GAT | CTC | TTC | CTG | CTC | 681 |
| Gln | Val | Leu | Gln | Glu | His | Leu | Gly | Arg | Glu | Ser | Asp | Leu | Phe | Leu | Leu |  |
|  |  |  |  | 200 |  |  |  |  | 205 |  |  |  |  | 210 |  |  |
| GAC | AGC | CGT | ACC | CTC | TGG | GCC | TCG | GAG | GAG | GGC | TGG | CTG | GTG | TTT | GAC | 729 |
| Asp | Ser | Arg | Thr | Leu | Trp | Ala | Ser | Glu | Glu | Gly | Trp | Leu | Val | Phe | Asp |  |
|  |  |  | 215 |  |  |  |  | 220 |  |  |  |  | 225 |  |  |  |
| ATC | ACA | GCC | ACC | AGC | AAC | CAC | TGG | GTG | GTC | AAT | CCG | CGG | CAC | AAC | CTG | 777 |
| Ile | Thr | Ala | Thr | Ser | Asn | His | Trp | Val | Val | Asn | Pro | Arg | His | Asn | Leu |  |
|  |  | 230 |  |  |  |  | 235 |  |  |  |  | 240 |  |  |  |  |
| GGC | CTG | CAG | CTC | TCG | GTG | GAG | ACG | CTG | GAT | GGG | CAG | AGC | ATC | AAC | CCC | 825 |
| Gly | Leu | Gln | Leu | Ser | Val | Glu | Thr | Leu | Asp | Gly | Gln | Ser | Ile | Asn | Pro |  |
| 245 |  |  |  |  | 250 |  |  |  |  | 255 |  |  |  |  |  |  |
| AAG | TTG | GCG | GGC | CTG | ATT | GGG | CGG | CAC | GGG | CCC | CAG | AAC | AAG | CAG | CCC | 873 |
| Lys | Leu | Ala | Gly | Leu | Ile | Gly | Arg | His | Gly | Pro | Gln | Asn | Lys | Gln | Pro |  |
| 260 |  |  |  |  | 265 |  |  |  |  | 270 |  |  |  |  | 275 |  |
| TTC | ATG | GTG | GCT | TTC | TTC | AAG | GCC | ACG | GAG | GTC | CAC | TTC | CGC | AGC | ATC | 921 |
| Phe | Met | Val | Ala | Phe | Phe | Lys | Ala | Thr | Glu | Val | His | Phe | Arg | Ser | Ile |  |
|  |  |  | 280 |  |  |  |  | 285 |  |  |  |  | 290 |  |  |  |
| CGG | TCC | ACG | GGG | AGC | AAA | CAG | CGC | AGC | CAG | AAC | CGC | TCC | AAG | ACG | CCC | 969 |
| Arg | Ser | Thr | Gly | Ser | Lys | Gln | Arg | Ser | Gln | Asn | Arg | Ser | Lys | Thr | Pro |  |
|  |  | 295 |  |  |  |  | 300 |  |  |  |  | 305 |  |  |  |  |
| AAG | AAC | CAG | GAA | GCC | CTG | CGG | ATG | GCC | AAC | GTG | GCA | GAG | AAC | AGC | AGC | 1017 |
| Lys | Asn | Gln | Glu | Ala | Leu | Arg | Met | Ala | Asn | Val | Ala | Glu | Asn | Ser | Ser |  |
|  |  | 310 |  |  |  |  | 315 |  |  |  |  | 320 |  |  |  |  |
| AGC | GAC | CAG | AGG | CAG | GCC | TGT | AAG | AAG | CAC | GAG | CTG | TAT | GTC | AGC | TTC | 1065 |
| Ser | Asp | Gln | Arg | Gln | Ala | Cys | Lys | Lys | His | Glu | Leu | Tyr | Val | Ser | Phe |  |
| 325 |  |  |  |  | 330 |  |  |  |  | 335 |  |  |  |  |  |  |
| CGA | GAC | CTG | GGC | TGG | CAG | GAC | TGG | ATC | ATC | GCG | CCT | GAA | GGC | TAC | GCC | 1113 |
| Arg | Asp | Leu | Gly | Trp | Gln | Asp | Trp | Ile | Ile | Ala | Pro | Glu | Gly | Tyr | Ala |  |
| 340 |  |  |  |  | 345 |  |  |  |  | 350 |  |  |  |  | 355 |  |
| GCC | TAC | TAC | TGT | GAG | GGG | GAG | TGT | GCC | TTC | CCT | CTG | AAC | TCC | TAC | ATG | 1161 |
| Ala | Tyr | Tyr | Cys | Glu | Gly | Glu | Cys | Ala | Phe | Pro | Leu | Asn | Ser | Tyr | Met |  |
|  |  |  |  | 360 |  |  |  |  | 365 |  |  |  |  | 370 |  |  |
| AAC | GCC | ACC | AAC | CAC | GCC | ATC | GTG | CAG | ACG | CTG | GTC | CAC | TTC | ATC | AAC | 1209 |
| Asn | Ala | Thr | Asn | His | Ala | Ile | Val | Gln | Thr | Leu | Val | His | Phe | Ile | Asn |  |
|  |  |  | 375 |  |  |  |  | 380 |  |  |  |  | 385 |  |  |  |
| CCG | GAA | ACG | GTG | CCC | AAG | CCC | TGC | TGT | GCG | CCC | ACG | CAG | CTC | AAT | GCC | 1257 |
| Pro | Glu | Thr | Val | Pro | Lys | Pro | Cys | Cys | Ala | Pro | Thr | Gln | Leu | Asn | Ala |  |
|  |  | 390 |  |  |  |  | 395 |  |  |  |  | 400 |  |  |  |  |
| ATC | TCC | GTC | CTC | TAC | TTC | GAT | GAC | AGC | TCC | AAC | GTC | ATC | CTG | AAG | AAA | 1305 |
| Ile | Ser | Val | Leu | Tyr | Phe | Asp | Asp | Ser | Ser | Asn | Val | Ile | Leu | Lys | Lys |  |

|     |     |     |     |     | 405 |     |     |     | 410 |     |     |     |     | 415 |     |     |      |
|-----|-----|-----|-----|-----|-----|-----|-----|-----|-----|-----|-----|-----|-----|-----|-----|-----|------|
| TAC | AGA | AAC | ATG | GTG | GTC | CGG | GCC | TGT | GGC | TGC | CAC | TAGCTCCTCC |  |  |  |  | 1351 |
| Tyr | Arg | Asn | Met | Val | Val | Arg | Ala | Cys | Gly | Cys | His |     |     |     |     |     |      |
| 420 |     |     |     |     | 425 |     |     |     |     | 430 |     |     |     |     |     |     |      |

```
GAGAATTCAG   ACCCTTTGGG   GCCAAGTTTT   TCTGGATCCT   CCATTGCTCG   CCTTGGCCAG          1411

GAACCAGCAG   ACCAACTGCC   TTTTGTGAGA   CCTTCCCCTC   CCTATCCCCA   ACTTTAAAGG          1471

TGTGAGAGTA   TTAGGAAACA   TGAGCAGCAT   ATGGCTTTTG   ATCAGTTTTT   CAGTGGCAGC          1531

ATCCAATGAA   CAAGATCCTA   CAAGCTGTGC   AGGCAAAACC   TAGCAGGAAA   AAAAAACAAC          1591

GCATAAAGAA   AAATGGCCGG   GCCAGGTCAT   TGGCTGGGAA   GTCTCAGCCA   TGCACGGACT          1651

CGTTTCCAGA   GGTAATTATG   AGCGCCTACC   AGCCAGGCCA   CCCAGCCGTG   GGAGGAAGGG          1711

GGCGTGGCAA   GGGGTGGGCA   CATTGGTGTC   TGTGCGAAAG   GAAAATTGAC   CCGGAAGTTC          1771

CTGTAATAAA   TGTCACAATA   AAACGAATGA   ATGAAAAAAA   AAAAAAAAA A                      1822
```

( 2 ) INFORMATION FOR SEQ ID NO:4:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  His  Val  Arg  Ser  Leu  Arg  Ala  Ala  Ala  Pro  His  Ser  Phe  Val  Ala
  1              5                         10                        15

Leu  Trp  Ala  Pro  Leu  Phe  Leu  Leu  Arg  Ser  Ala  Leu  Ala  Asp  Phe  Ser
                20                         25                        30

Leu  Asp  Asn  Glu  Val  His  Ser  Ser  Phe  Ile  His  Arg  Arg  Leu  Arg  Ser
                35                         40                        45

Gln  Glu  Arg  Arg  Glu  Met  Gln  Arg  Glu  Ile  Leu  Ser  Ile  Leu  Gly  Leu
           50                         55                        60

Pro  His  Arg  Pro  Arg  Pro  His  Leu  Gln  Gly  Lys  His  Asn  Ser  Ala  Pro
 65                         70                         75                        80

Met  Phe  Met  Leu  Asp  Leu  Tyr  Asn  Ala  Met  Ala  Val  Glu  Glu  Gly  Gly
                85                         90                        95

Gly  Pro  Gly  Gly  Gln  Gly  Phe  Ser  Tyr  Pro  Tyr  Lys  Ala  Val  Phe  Ser
               100                        105                       110

Thr  Gln  Gly  Pro  Pro  Leu  Ala  Ser  Leu  Gln  Asp  Ser  His  Phe  Leu  Thr
               115                        120                       125

Asp  Ala  Asp  Met  Val  Met  Ser  Phe  Val  Asn  Leu  Val  Glu  His  Asp  Lys
          130                        135                       140

Glu  Phe  Phe  His  Pro  Arg  Tyr  His  His  Arg  Glu  Phe  Arg  Phe  Asp  Leu
145                        150                        155                       160

Ser  Lys  Ile  Pro  Glu  Gly  Glu  Ala  Val  Thr  Ala  Ala  Glu  Phe  Arg  Ile
               165                        170                       175

Tyr  Lys  Asp  Tyr  Ile  Arg  Glu  Arg  Phe  Asp  Asn  Glu  Thr  Phe  Arg  Ile
              180                        185                       190

Ser  Val  Tyr  Gln  Val  Leu  Gln  Glu  His  Leu  Gly  Arg  Glu  Ser  Asp  Leu
              195                        200                       205

Phe  Leu  Leu  Asp  Ser  Arg  Thr  Leu  Trp  Ala  Ser  Glu  Glu  Gly  Trp  Leu
         210                        215                        220

Val  Phe  Asp  Ile  Thr  Ala  Thr  Ser  Asn  His  Trp  Val  Val  Asn  Pro  Arg
225                        230                        235                       240

His  Asn  Leu  Gly  Leu  Gln  Leu  Ser  Val  Glu  Thr  Leu  Asp  Gly  Gln  Ser
```

|     |     |     |     |     |     |     |     |     |     |     |     |     |     |     |
|---|---|---|---|---|---|---|---|---|---|---|---|---|---|---|
|     |     |     |     | 245 |     |     |     | 250 |     |     |     | 255 |     |     |
| Ile | Asn | Pro | Lys<br>260 | Leu | Ala | Gly | Leu | Ile<br>265 | Gly | Arg | His | Gly | Pro<br>270 | Gln | Asn |
| Lys | Gln | Pro<br>275 | Phe | Met | Val | Ala | Phe<br>280 | Phe | Lys | Ala | Thr | Glu<br>285 | Val | His | Phe |
| Arg | Ser<br>290 | Ile | Arg | Ser | Thr | Gly<br>295 | Ser | Lys | Gln | Arg | Ser<br>300 | Gln | Asn | Arg | Ser |
| Lys<br>305 | Thr | Pro | Lys | Asn | Gln<br>310 | Glu | Ala | Leu | Arg | Met<br>315 | Ala | Asn | Val | Ala | Glu<br>320 |
| Asn | Ser | Ser | Ser | Asp<br>325 | Gln | Arg | Gln | Ala | Cys<br>330 | Lys | Lys | His | Glu | Leu<br>335 | Tyr |
| Val | Ser | Phe | Arg<br>340 | Asp | Leu | Gly | Trp | Gln<br>345 | Asp | Trp | Ile | Ile | Ala<br>350 | Pro | Glu |
| Gly | Tyr | Ala<br>355 | Ala | Tyr | Tyr | Cys | Glu<br>360 | Gly | Glu | Cys | Ala | Phe<br>365 | Pro | Leu | Asn |
| Ser | Tyr | Met<br>370 | Asn | Ala | Thr | Asn | His<br>375 | Ala | Ile | Val | Gln | Thr<br>380 | Leu | Val | His |
| Phe<br>385 | Ile | Asn | Pro | Glu | Thr<br>390 | Val | Pro | Lys | Pro | Cys<br>395 | Cys | Ala | Pro | Thr | Gln<br>400 |
| Leu | Asn | Ala | Ile | Ser<br>405 | Val | Leu | Tyr | Phe | Asp<br>410 | Asp | Ser | Ser | Asn | Val<br>415 | Ile |
| Leu | Lys | Lys | Tyr<br>420 | Arg | Asn | Met | Val | Val<br>425 | Arg | Ala | Cys | Gly | Cys<br>430 | His |     |

( 2 ) INFORMATION FOR SEQ ID NO:5:

( i ) SEQUENCE CHARACTERISTICS:
        ( A ) LENGTH: 1873 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 104..1393
        ( D ) OTHER INFORMATION: /function="OSTEOGENIC PROTEIN"
            / product= "mOP1-PP"
            / note= "mOP1 cDNA"

( x i ) SEQUENCE DESCRIPTION: SEQ ID NO:5:

| | | | | | | | | | | | | | | | |
|---|---|---|---|---|---|---|---|---|---|---|---|---|---|---|---|
| CTGCAGCAAG | | | TGACCTCGGG | | | TCGTGGACCG | | | CTGCCCTGCC | | | CCCTCCGCTG | | CCACCTGGGG | 60 |
| CGGCGCGGGC | | | CCGGTGCCCC | | | GGATCGCGCG | | | TAGAGCCGGC | | | GCG | ATG<br>Met<br>1 | CAC<br>His | GTG<br>Val | CGC<br>Arg | 115 |
| TCG<br>Ser<br>5 | CTG<br>Leu | CGC<br>Arg | GCT<br>Ala | GCG<br>Ala | GCG<br>Ala<br>10 | CCA<br>Pro | CAC<br>His | AGC<br>Ser | TTC<br>Phe | GTG<br>Val<br>15 | GCG<br>Ala | CTC<br>Leu | TGG<br>Trp | GCG<br>Ala | CCT<br>Pro<br>20 | 163 |
| CTG<br>Leu | TTC<br>Phe | TTG<br>Leu | CTG<br>Leu | CGC<br>Arg<br>25 | TCC<br>Ser | GCC<br>Ala | CTG<br>Leu | GCC<br>Ala | GAT<br>Asp<br>30 | TTC<br>Phe | AGC<br>Ser | CTG<br>Leu | GAC<br>Asp | AAC<br>Asn<br>35 | GAG<br>Glu | 211 |
| GTG<br>Val | CAC<br>His | TCC<br>Ser | AGC<br>Ser<br>40 | TTC<br>Phe | ATC<br>Ile | CAC<br>His | CGG<br>Arg | CGC<br>Arg<br>45 | CTC<br>Leu | CGC<br>Arg | AGC<br>Ser | CAG<br>Gln | GAG<br>Glu<br>50 | CGG<br>Arg | CGG<br>Arg | 259 |
| GAG<br>Glu | ATG<br>Met | CAG<br>Gln<br>55 | CGG<br>Arg | GAG<br>Glu | ATC<br>Ile | CTG<br>Leu | TCC<br>Ser<br>60 | ATC<br>Ile | TTA<br>Leu | GGG<br>Gly | TTG<br>Leu | CCC<br>Pro<br>65 | CAT<br>His | CGC<br>Arg | CCG<br>Pro | 307 |
| CGC<br>Arg | CCG<br>Pro<br>70 | CAC<br>His | CTC<br>Leu | CAG<br>Gln | GGA<br>Gly | AAG<br>Lys<br>75 | CAT<br>His | AAT<br>Asn | TCG<br>Ser | GCG<br>Ala | CCC<br>Pro<br>80 | ATG<br>Met | TTC<br>Phe | ATG<br>Met | TTG<br>Leu | 355 |

| | | | | | | | | | | | | | | | | |
|---|---|---|---|---|---|---|---|---|---|---|---|---|---|---|---|---|
| GAC | CTG | TAC | AAC | GCC | ATG | GCG | GTG | GAG | GAG | AGC | GGG | CCG | GAC | GGA | CAG | 403 |
| Asp | Leu | Tyr | Asn | Ala | Met | Ala | Val | Glu | Glu | Ser | Gly | Pro | Asp | Gly | Gln | |
| 85 | | | | 90 | | | | | 95 | | | | | 100 | | |
| GGC | TTC | TCC | TAC | CCC | TAC | AAG | GCC | GTC | TTC | AGT | ACC | CAG | GGC | CCC | CCT | 451 |
| Gly | Phe | Ser | Tyr | Pro | Tyr | Lys | Ala | Val | Phe | Ser | Thr | Gln | Gly | Pro | Pro | |
| | | | | 105 | | | | | 110 | | | | | 115 | | |
| TTA | GCC | AGC | CTG | CAG | GAC | AGC | CAT | TTC | CTC | ACT | GAC | GCC | GAC | ATG | GTC | 499 |
| Leu | Ala | Ser | Leu | Gln | Asp | Ser | His | Phe | Leu | Thr | Asp | Ala | Asp | Met | Val | |
| | | | 120 | | | | | 125 | | | | | 130 | | | |
| ATG | AGC | TTC | GTC | AAC | CTA | GTG | GAA | CAT | GAC | AAA | GAA | TTC | TTC | CAC | CCT | 547 |
| Met | Ser | Phe | Val | Asn | Leu | Val | Glu | His | Asp | Lys | Glu | Phe | Phe | His | Pro | |
| | | 135 | | | | | 140 | | | | | 145 | | | | |
| CGA | TAC | CAC | CAT | CGG | GAG | TTC | CGG | TTT | GAT | CTT | TCC | AAG | ATC | CCC | GAG | 595 |
| Arg | Tyr | His | His | Arg | Glu | Phe | Arg | Phe | Asp | Leu | Ser | Lys | Ile | Pro | Glu | |
| | | 150 | | | | | 155 | | | | | 160 | | | | |
| GGC | GAA | CGG | GTG | ACC | GCA | GCC | GAA | TTC | AGG | ATC | TAT | AAG | GAC | TAC | ATC | 643 |
| Gly | Glu | Arg | Val | Thr | Ala | Ala | Glu | Phe | Arg | Ile | Tyr | Lys | Asp | Tyr | Ile | |
| 165 | | | | 170 | | | | | 175 | | | | | 180 | | |
| CGG | GAG | CGA | TTT | GAC | AAC | GAG | ACC | TTC | CAG | ATC | ACA | GTC | TAT | CAG | GTG | 691 |
| Arg | Glu | Arg | Phe | Asp | Asn | Glu | Thr | Phe | Gln | Ile | Thr | Val | Tyr | Gln | Val | |
| | | | | 185 | | | | | 190 | | | | | 195 | | |
| CTC | CAG | GAG | CAC | TCA | GGC | AGG | GAG | TCG | GAC | CTC | TTC | TTG | CTG | GAC | AGC | 739 |
| Leu | Gln | Glu | His | Ser | Gly | Arg | Glu | Ser | Asp | Leu | Phe | Leu | Leu | Asp | Ser | |
| | | | 200 | | | | | 205 | | | | | 210 | | | |
| CGC | ACC | ATC | TGG | GCT | TCT | GAG | GAG | GGC | TGG | TTG | GTG | TTT | GAT | ATC | ACA | 787 |
| Arg | Thr | Ile | Trp | Ala | Ser | Glu | Glu | Gly | Trp | Leu | Val | Phe | Asp | Ile | Thr | |
| | | 215 | | | | | 220 | | | | | 225 | | | | |
| GCC | ACC | AGC | AAC | CAC | TGG | GTG | GTC | AAC | CCT | CGG | CAC | AAC | CTG | GGC | TTA | 835 |
| Ala | Thr | Ser | Asn | His | Trp | Val | Val | Asn | Pro | Arg | His | Asn | Leu | Gly | Leu | |
| | 230 | | | | | 235 | | | | | 240 | | | | | |
| CAG | CTC | TCT | GTG | GAG | ACC | CTG | GAT | GGG | CAG | AGC | ATC | AAC | CCC | AAG | TTG | 883 |
| Gln | Leu | Ser | Val | Glu | Thr | Leu | Asp | Gly | Gln | Ser | Ile | Asn | Pro | Lys | Leu | |
| 245 | | | | | 250 | | | | | 255 | | | | | 260 | |
| GCA | GGC | CTG | ATT | GGA | CGG | CAT | GGA | CCC | CAG | AAC | AAG | CAA | CCC | TTC | ATG | 931 |
| Ala | Gly | Leu | Ile | Gly | Arg | His | Gly | Pro | Gln | Asn | Lys | Gln | Pro | Phe | Met | |
| | | | | 265 | | | | | 270 | | | | | 275 | | |
| GTG | GCC | TTC | TTC | AAG | GCC | ACG | GAA | GTC | CAT | CTC | CGT | AGT | ATC | CGG | TCC | 979 |
| Val | Ala | Phe | Phe | Lys | Ala | Thr | Glu | Val | His | Leu | Arg | Ser | Ile | Arg | Ser | |
| | | | 280 | | | | | 285 | | | | | 290 | | | |
| ACG | GGG | GGC | AAG | CAG | CGC | AGC | CAG | AAT | CGC | TCC | AAG | ACG | CCA | AAG | AAC | 1027 |
| Thr | Gly | Gly | Lys | Gln | Arg | Ser | Gln | Asn | Arg | Ser | Lys | Thr | Pro | Lys | Asn | |
| | | 295 | | | | | 300 | | | | | 305 | | | | |
| CAA | GAG | GCC | CTG | AGG | ATG | GCC | AGT | GTG | GCA | GAA | AAC | AGC | AGC | AGT | GAC | 1075 |
| Gln | Glu | Ala | Leu | Arg | Met | Ala | Ser | Val | Ala | Glu | Asn | Ser | Ser | Ser | Asp | |
| | 310 | | | | | 315 | | | | | 320 | | | | | |
| CAG | AGG | CAG | GCC | TGC | AAG | AAA | CAT | GAG | CTG | TAC | GTC | AGC | TTC | CGA | GAC | 1123 |
| Gln | Arg | Gln | Ala | Cys | Lys | Lys | His | Glu | Leu | Tyr | Val | Ser | Phe | Arg | Asp | |
| 325 | | | | | 330 | | | | | 335 | | | | | 340 | |
| CTT | GGC | TGG | CAG | GAC | TGG | ATC | ATT | GCA | CCT | GAA | GGC | TAT | GCT | GCC | TAC | 1171 |
| Leu | Gly | Trp | Gln | Asp | Trp | Ile | Ile | Ala | Pro | Glu | Gly | Tyr | Ala | Ala | Tyr | |
| | | | | 345 | | | | | 350 | | | | | 355 | | |
| TAC | TGT | GAG | GGA | GAG | TGT | GCC | TTC | CCT | CTG | AAC | TCC | TAC | ATG | AAC | GCC | 1219 |
| Tyr | Cys | Glu | Gly | Glu | Cys | Ala | Phe | Pro | Leu | Asn | Ser | Tyr | Met | Asn | Ala | |
| | | | | 360 | | | | | 365 | | | | | 370 | | |
| ACC | AAC | CAC | GCC | ATC | GTC | CAG | ACA | CTG | GTT | CAC | TTC | ATC | AAC | CCA | GAC | 1267 |
| Thr | Asn | His | Ala | Ile | Val | Gln | Thr | Leu | Val | His | Phe | Ile | Asn | Pro | Asp | |
| | | 375 | | | | | 380 | | | | | 385 | | | | |
| ACA | GTA | CCC | AAG | CCC | TGC | TGT | GCG | CCC | ACC | CAG | CTC | AAC | GCC | ATC | TCT | 1315 |
| Thr | Val | Pro | Lys | Pro | Cys | Cys | Ala | Pro | Thr | Gln | Leu | Asn | Ala | Ile | Ser | |
| | 390 | | | | | 395 | | | | | 400 | | | | | |

-continued

```
GTC CTC TAC TTC GAC GAC AGC TCT AAT GTC ATC CTG AAG AAG TAC AGA          1363
Val Leu Tyr Phe Asp Asp Ser Ser Asn Val Ile Leu Lys Lys Tyr Arg
405                     410                 415                 420

AAC ATG GTG GTC CGG GCC TGT GGC TGC CAC TAGCTCTTCC TGAGACCCTG           1413
Asn Met Val Val Arg Ala Cys Gly Cys His
                425                 430

ACCTTTGCGG GGCCACACCT TTCCAAATCT TCGATGTCTC ACCATCTAAG TCTCTCACTG        1473
CCCACCTTGG CGAGGAGAAC AGACCAACCT CTCCTGAGCC TTCCCTCACC TCCCAACCGG        1533
AAGCATGTAA GGGTTCCAGA AACCTGAGCG TGCAGCAGCT GATGAGCGCC CTTTCCTTCT        1593
GGCACGTGAC GGACAAGATC CTACCAGCTA CCACAGCAAA CGCCTAAGAG CAGGAAAAAT        1653
GTCTGCCAGG AAAGTGTCCA GTGTCCACAT GGCCCCTGGC GCTCTGAGTC TTTGAGGAGT        1713
AATCGCAAGC CTCGTTCAGC TGCAGCAGAA GGAAGGGCTT AGCCAGGGTG GGCGCTGGCG        1773
TCTGTGTTGA AGGGAAACCA AGCAGAAGCC ACTGTAATGA TATGTCACAA TAAAACCCAT        1833
GAATGAAAAA AAAAAAAAAA AAAAAAAAA AAAAGAATTC                               1873
```

(2) INFORMATION FOR SEQ ID NO:6:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:6:

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
    130                 135                 140

Phe Phe His Pro Arg Tyr His His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
        195                 200                 205

Leu Leu Asp Ser Arg Thr Ile Trp Ala Ser Glu Glu Gly Trp Leu Val
    210                 215                 220

Phe Asp Ile Thr Ala Thr Ser Asn His Trp Val Val Asn Pro Arg His
```

-continued

| | | | | 225 | | | | | 230 | | | | | 235 | | | | | 240 |
|---|---|---|---|---|---|---|---|---|---|---|---|---|---|---|---|---|---|---|---|
| Asn | Leu | Gly | Leu | Gln | Leu | Ser | Val | Glu | Thr | Leu | Asp | Gly | Gln | Ser | Ile |
| | | | | | | 245 | | | | 250 | | | | | 255 | | | | |
| Asn | Pro | Lys | Leu | Ala | Gly | Leu | Ile | Gly | Arg | His | Gly | Pro | Gln | Asn | Lys |
| | | | | 260 | | | | | 265 | | | | | 270 | | | | | |
| Gln | Pro | Phe | Met | Val | Ala | Phe | Phe | Lys | Ala | Thr | Glu | Val | His | Leu | Arg |
| | | | 275 | | | | | 280 | | | | | 285 | | | | | | |
| Ser | Ile | Arg | Ser | Thr | Gly | Gly | Lys | Gln | Arg | Ser | Gln | Asn | Arg | Ser | Lys |
| | | 290 | | | | | 295 | | | | | 300 | | | | | | | |
| Thr | Pro | Lys | Asn | Gln | Glu | Ala | Leu | Arg | Met | Ala | Ser | Val | Ala | Glu | Asn |
| 305 | | | | | 310 | | | | | 315 | | | | | 320 | | | | |
| Ser | Ser | Ser | Asp | Gln | Arg | Gln | Ala | Cys | Lys | Lys | His | Glu | Leu | Tyr | Val |
| | | | | 325 | | | | | 330 | | | | | 335 | | | | | |
| Ser | Phe | Arg | Asp | Leu | Gly | Trp | Gln | Asp | Trp | Ile | Ile | Ala | Pro | Glu | Gly |
| | | | 340 | | | | | 345 | | | | | 350 | | | | | | |
| Tyr | Ala | Ala | Tyr | Tyr | Cys | Glu | Gly | Glu | Cys | Ala | Phe | Pro | Leu | Asn | Ser |
| | | 355 | | | | | 360 | | | | | 365 | | | | | | | |
| Tyr | Met | Asn | Ala | Thr | Asn | His | Ala | Ile | Val | Gln | Thr | Leu | Val | His | Phe |
| | 370 | | | | | 375 | | | | | 380 | | | | | | | | |
| Ile | Asn | Pro | Asp | Thr | Val | Pro | Lys | Pro | Cys | Cys | Ala | Pro | Thr | Gln | Leu |
| 385 | | | | | 390 | | | | | 395 | | | | | 400 | | | | |
| Asn | Ala | Ile | Ser | Val | Leu | Tyr | Phe | Asp | Asp | Ser | Ser | Asn | Val | Ile | Leu |
| | | | | 405 | | | | | 410 | | | | | 415 | | | | | |
| Lys | Lys | Tyr | Arg | Asn | Met | Val | Val | Arg | Ala | Cys | Gly | Cys | His | | |
| | | | 420 | | | | | 425 | | | | | 430 | | | | | | |

( 2 ) INFORMATION FOR SEQ ID NO:7:

( i ) SEQUENCE CHARACTERISTICS:
        ( A ) LENGTH: 1723 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 490..1696
        ( D ) OTHER INFORMATION: /function="OSTEOGENIC PROTEIN"
            / product= "hOP2-PP"
            / note= "hOP2 cDNA"

( x i ) SEQUENCE DESCRIPTION: SEQ ID NO:7:

```
GGCGCCGGCA  GAGCAGGAGT  GGCTGGAGGA  GCTGTGGTTG  GAGCAGGAGG  TGGCACGGCA      60

GGGCTGGAGG  GCTCCCTATG  AGTGGCGGAG  ACGGCCCAGG  AGGCGCTGGA  GCAACAGCTC     120

CCACACCGCA  CCAAGCGGTG  GCTGCAGGAG  CTCGCCCATC  GCCCCTGCGC  TGCTCGGACC     180

GCGGCCACAG  CCGGACTGGC  GGGTACGGCG  GCGACAGAGG  CATTGGCCGA  GAGTCCCAGT     240

CCGCAGAGTA  GCCCCGGCCT  CGAGGCGGTG  GCGTCCCGGT  CCTCTCCGTC  AGGAGCCAG      300

GACAGGTGTC  GCGCGGCGGG  GCTCCAGGGA  CCGCGCCTGA  GGCCGGCTGC  CCGCCCGTCC     360

CGCCCCGCCC  CGCCGCCCGC  CGCCCGCCGA  GCCCAGCCTC  CTTGCCGTCG  GGGCGTCCCC     420

AGGCCCTGGG  TCGGCCGCGG  AGCCGATGCG  CGCCCGCTGA  GCGCCCAGC   TGAGCGCCCC     480
```

```
CGGCCTGCC ATG ACC GCG CTC CCC GGC CCG CTC TGG CTC CTG GGC CTG      528
          Met Thr Ala Leu Pro Gly Pro Leu Trp Leu Leu Gly Leu
            1               5                   10

GCG CTA TGC GCG CTG GGC GGG GGC GGC CCC GGC CTG CGA CCC CCG CCC      576
Ala Leu Cys Ala Leu Gly Gly Gly Gly Pro Gly Leu Arg Pro Pro Pro
```

|  |  |  |  |  |  |  |  |  |  |  |  |  |  |  |  |  |
|---|---|---|---|---|---|---|---|---|---|---|---|---|---|---|---|---|
|  |  | 15 |  |  |  |  | 20 |  |  |  |  | 25 |  |  |  |  |
| GGC | TGT | CCC | CAG | CGA | CGT | CTG | GGC | GCG | CGC | GAG | CGC | CGG | GAC | GTG | CAG | 624 |
| Gly | Cys | Pro | Gln | Arg | Arg | Leu | Gly | Ala | Arg | Glu | Arg | Arg | Asp | Val | Gln |  |
| 30 |  |  |  | 35 |  |  |  |  | 40 |  |  |  |  |  | 45 |  |
| CGC | GAG | ATC | CTG | GCG | GTG | CTC | GGG | CTG | CCT | GGG | CGG | CCC | CGG | CCC | CGC | 672 |
| Arg | Glu | Ile | Leu | Ala | Val | Leu | Gly | Leu | Pro | Gly | Arg | Pro | Arg | Pro | Arg |  |
|  |  |  |  | 50 |  |  |  |  | 55 |  |  |  |  | 60 |  |  |
| GCG | CCA | CCC | GCC | TCC | CGG | CTG | CCC | GCG | TCC | GCG | CCG | CTC | TTC | ATG | 720 |
| Ala | Pro | Pro | Ala | Ser | Arg | Leu | Pro | Ala | Ser | Ala | Pro | Leu | Phe | Met |  |
|  |  |  |  | 65 |  |  |  |  | 70 |  |  |  |  | 75 |  |  |
| CTG | GAC | CTG | TAC | CAC | GCC | ATG | GCC | GGC | GAC | GAC | GAG | GAC | GGC | GCG | 768 |
| Leu | Asp | Leu | Tyr | His | Ala | Met | Ala | Gly | Asp | Asp | Asp | Glu | Asp | Gly | Ala |  |
|  |  | 80 |  |  |  |  | 85 |  |  |  |  | 90 |  |  |  |  |
| CCC | GCG | GAG | CGG | CGC | CTG | GGC | CGC | GCC | GAC | CTG | GTC | ATG | AGC | TTC | GTT | 816 |
| Pro | Ala | Glu | Arg | Arg | Leu | Gly | Arg | Ala | Asp | Leu | Val | Met | Ser | Phe | Val |  |
|  | 95 |  |  |  |  | 100 |  |  |  |  | 105 |  |  |  |  |  |
| AAC | ATG | GTG | GAG | CGA | GAC | CGT | GCC | CTG | GGC | CAC | CAG | GAG | CCC | CAT | TGG | 864 |
| Asn | Met | Val | Glu | Arg | Asp | Arg | Ala | Leu | Gly | His | Gln | Glu | Pro | His | Trp |  |
| 110 |  |  |  |  | 115 |  |  |  |  | 120 |  |  |  |  | 125 |  |
| AAG | GAG | TTC | CGC | TTT | GAC | CTG | ACC | CAG | ATC | CCG | GCT | GGG | GAG | GCG | GTC | 912 |
| Lys | Glu | Phe | Arg | Phe | Asp | Leu | Thr | Gln | Ile | Pro | Ala | Gly | Glu | Ala | Val |  |
|  |  |  |  | 130 |  |  |  |  | 135 |  |  |  |  | 140 |  |  |
| ACA | GCT | GCG | GAG | TTC | CGG | ATT | TAC | AAG | GTG | CCC | AGC | ATC | CAC | CTG | CTC | 960 |
| Thr | Ala | Ala | Glu | Phe | Arg | Ile | Tyr | Lys | Val | Pro | Ser | Ile | His | Leu | Leu |  |
|  |  |  | 145 |  |  |  |  | 150 |  |  |  |  | 155 |  |  |  |
| AAC | AGG | ACC | CTC | CAC | GTC | AGC | ATG | TTC | CAG | GTG | GTC | CAG | GAG | CAG | TCC | 1008 |
| Asn | Arg | Thr | Leu | His | Val | Ser | Met | Phe | Gln | Val | Val | Gln | Glu | Gln | Ser |  |
|  |  |  | 160 |  |  |  |  | 165 |  |  |  |  | 170 |  |  |  |
| AAC | AGG | GAG | TCT | GAC | TTG | TTC | TTT | TTG | GAT | CTT | CAG | ACG | CTC | CGA | GCT | 1056 |
| Asn | Arg | Glu | Ser | Asp | Leu | Phe | Phe | Leu | Asp | Leu | Gln | Thr | Leu | Arg | Ala |  |
|  | 175 |  |  |  |  | 180 |  |  |  |  | 185 |  |  |  |  |  |
| GGA | GAC | GAG | GGC | TGG | CTG | GTG | CTG | GAT | GTC | ACA | GCA | GCC | AGT | GAC | TGC | 1104 |
| Gly | Asp | Glu | Gly | Trp | Leu | Val | Leu | Asp | Val | Thr | Ala | Ala | Ser | Asp | Cys |  |
| 190 |  |  |  |  | 195 |  |  |  |  | 200 |  |  |  |  | 205 |  |
| TGG | TTG | CTG | AAG | CGT | CAC | AAG | GAC | CTG | GGA | CTC | CGC | CTC | TAT | GTG | GAG | 1152 |
| Trp | Leu | Leu | Lys | Arg | His | Lys | Asp | Leu | Gly | Leu | Arg | Leu | Tyr | Val | Glu |  |
|  |  |  |  | 210 |  |  |  |  | 215 |  |  |  |  | 220 |  |  |
| ACT | GAG | GAC | GGG | CAC | AGC | GTG | GAT | CCT | GGC | CTG | GCC | GGC | CTG | CTG | GGT | 1200 |
| Thr | Glu | Asp | Gly | His | Ser | Val | Asp | Pro | Gly | Leu | Ala | Gly | Leu | Leu | Gly |  |
|  |  |  | 225 |  |  |  |  | 230 |  |  |  |  | 235 |  |  |  |
| CAA | CGG | GCC | CCA | CGC | TCC | CAA | CAG | CCT | TTC | GTG | GTC | ACT | TTC | TTC | AGG | 1248 |
| Gln | Arg | Ala | Pro | Arg | Ser | Gln | Gln | Pro | Phe | Val | Val | Thr | Phe | Phe | Arg |  |
|  |  | 240 |  |  |  |  | 245 |  |  |  |  | 250 |  |  |  |  |
| GCC | AGT | CCG | AGT | CCC | ATC | CGC | ACC | CCT | CGG | GCA | GTG | AGG | CCA | CTG | AGG | 1296 |
| Ala | Ser | Pro | Ser | Pro | Ile | Arg | Thr | Pro | Arg | Ala | Val | Arg | Pro | Leu | Arg |  |
|  | 255 |  |  |  |  | 260 |  |  |  |  | 265 |  |  |  |  |  |
| AGG | AGG | CAG | CCG | AAG | AAA | AGC | AAC | GAG | CTG | CCG | CAG | GCC | AAC | CGA | CTC | 1344 |
| Arg | Arg | Gln | Pro | Lys | Lys | Ser | Asn | Glu | Leu | Pro | Gln | Ala | Asn | Arg | Leu |  |
| 270 |  |  |  |  | 275 |  |  |  |  | 280 |  |  |  |  | 285 |  |
| CCA | GGG | ATC | TTT | GAT | GAC | GTC | CAC | GGC | TCC | CAC | GGC | CGG | CAG | GTC | TGC | 1392 |
| Pro | Gly | Ile | Phe | Asp | Asp | Val | His | Gly | Ser | His | Gly | Arg | Gln | Val | Cys |  |
|  |  |  |  | 290 |  |  |  |  | 295 |  |  |  |  | 300 |  |  |
| CGT | CGG | CAC | GAG | CTC | TAC | GTC | AGC | TTC | CAG | GAC | CTC | GGC | TGG | CTG | GAC | 1440 |
| Arg | Arg | His | Glu | Leu | Tyr | Val | Ser | Phe | Gln | Asp | Leu | Gly | Trp | Leu | Asp |  |
|  |  |  | 305 |  |  |  |  | 310 |  |  |  |  | 315 |  |  |  |
| TGG | GTC | ATC | GCT | CCC | CAA | GGC | TAC | TCG | GCC | TAT | TAC | TGT | GAG | GGG | GAG | 1488 |
| Trp | Val | Ile | Ala | Pro | Gln | Gly | Tyr | Ser | Ala | Tyr | Tyr | Cys | Glu | Gly | Glu |  |
|  |  | 320 |  |  |  |  | 325 |  |  |  |  | 330 |  |  |  |  |
| TGC | TCC | TTC | CCA | CTG | GAC | TCC | TGC | ATG | AAT | GCC | ACC | AAC | CAC | GCC | ATC | 1536 |
| Cys | Ser | Phe | Pro | Leu | Asp | Ser | Cys | Met | Asn | Ala | Thr | Asn | His | Ala | Ile |  |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 335 |     |     |     |     | 340 |     |     |     |     | 345 |     |     |     |     |
| CTG | CAG | TCC | CTG | GTG | CAC | CTG | ATG | AAG | CCA | AAC | GCA | GTC | CCC | AAG | GCG | 1584 |
| Leu | Gln | Ser | Leu | Val | His | Leu | Met | Lys | Pro | Asn | Ala | Val | Pro | Lys | Ala |     |
| 350 |     |     |     |     | 355 |     |     |     | 360 |     |     |     |     |     | 365 |     |
| TGC | TGT | GCA | CCC | ACC | AAG | CTG | AGC | GCC | ACC | TCT | GTG | CTC | TAC | TAT | GAC | 1632 |
| Cys | Cys | Ala | Pro | Thr | Lys | Leu | Ser | Ala | Thr | Ser | Val | Leu | Tyr | Tyr | Asp |     |
|     |     |     | 370 |     |     |     |     | 375 |     |     |     |     |     | 380 |     |     |
| AGC | AGC | AAC | AAC | GTC | ATC | CTG | CGC | AAA | GCC | CGC | AAC | ATG | GTG | GTC | AAG | 1680 |
| Ser | Ser | Asn | Asn | Val | Ile | Leu | Arg | Lys | Ala | Arg | Asn | Met | Val | Val | Lys |     |
|     |     | 385 |     |     |     |     | 390 |     |     |     |     | 395 |     |     |     |     |
| GCC | TGC | GGC | TGC | CAC |     | T GAGTCAGCCC | GCCCAGCCCT | ACTGCAG |     |     |     |     |     |     |     | 1723 |
| Ala | Cys | Gly | Cys | His |     |     |     |     |     |     |     |     |     |     |     |     |
| 400 |     |     |     |     |     |     |     |     |     |     |     |     |     |     |     |     |

( 2 ) INFORMATION FOR SEQ ID NO:8:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Thr | Ala | Leu | Pro | Gly | Pro | Leu | Trp | Leu | Leu | Gly | Leu | Ala | Leu | Cys |
| --- | --- | --- | --- | --- | --- | --- | --- | --- | --- | --- | --- | --- | --- | --- | --- |
| 1 |  |  |  | 5 |  |  |  | 10 |  |  |  |  |  | 15 |  |
| Ala | Leu | Gly | Gly | Gly | Gly | Pro | Gly | Leu | Arg | Pro | Pro | Pro | Gly | Cys | Pro |
|  |  |  | 20 |  |  |  |  | 25 |  |  |  | 30 |  |  |  |
| Gln | Arg | Arg | Leu | Gly | Ala | Arg | Glu | Arg | Arg | Asp | Val | Gln | Arg | Glu | Ile |
|  |  | 35 |  |  |  |  | 40 |  |  |  |  | 45 |  |  |  |
| Leu | Ala | Val | Leu | Gly | Leu | Pro | Gly | Arg | Pro | Arg | Pro | Arg | Ala | Pro | Pro |
|  | 50 |  |  |  |  | 55 |  |  |  |  | 60 |  |  |  |  |
| Ala | Ala | Ser | Arg | Leu | Pro | Ala | Ser | Ala | Pro | Leu | Phe | Met | Leu | Asp | Leu |
| 65 |  |  |  |  | 70 |  |  |  |  | 75 |  |  |  |  | 80 |
| Tyr | His | Ala | Met | Ala | Gly | Asp | Asp | Asp | Glu | Asp | Gly | Ala | Pro | Ala | Glu |
|  |  |  |  | 85 |  |  |  |  | 90 |  |  |  |  | 95 |  |
| Arg | Arg | Leu | Gly | Arg | Ala | Asp | Leu | Val | Met | Ser | Phe | Val | Asn | Met | Val |
|  |  |  | 100 |  |  |  |  | 105 |  |  |  |  | 110 |  |  |
| Glu | Arg | Asp | Arg | Ala | Leu | Gly | His | Gln | Glu | Pro | His | Trp | Lys | Glu | Phe |
|  |  | 115 |  |  |  |  | 120 |  |  |  |  | 125 |  |  |  |
| Arg | Phe | Asp | Leu | Thr | Gln | Ile | Pro | Ala | Gly | Glu | Ala | Val | Thr | Ala | Ala |
|  | 130 |  |  |  |  | 135 |  |  |  |  | 140 |  |  |  |  |
| Glu | Phe | Arg | Ile | Tyr | Lys | Val | Pro | Ser | Ile | His | Leu | Leu | Asn | Arg | Thr |
| 145 |  |  |  |  | 150 |  |  |  |  | 155 |  |  |  |  | 160 |
| Leu | His | Val | Ser | Met | Phe | Gln | Val | Val | Gln | Glu | Gln | Ser | Asn | Arg | Glu |
|  |  |  |  | 165 |  |  |  |  | 170 |  |  |  |  | 175 |  |
| Ser | Asp | Leu | Phe | Phe | Leu | Asp | Leu | Gln | Thr | Leu | Arg | Ala | Gly | Asp | Glu |
|  |  |  | 180 |  |  |  |  | 185 |  |  |  |  | 190 |  |  |
| Gly | Trp | Leu | Val | Leu | Asp | Val | Thr | Ala | Ala | Ser | Asp | Cys | Trp | Leu | Leu |
|  |  |  | 195 |  |  |  |  | 200 |  |  |  |  | 205 |  |  |
| Lys | Arg | His | Lys | Asp | Leu | Gly | Leu | Arg | Leu | Tyr | Val | Glu | Thr | Glu | Asp |
|  | 210 |  |  |  |  | 215 |  |  |  |  | 220 |  |  |  |  |
| Gly | His | Ser | Val | Asp | Pro | Gly | Leu | Ala | Gly | Leu | Leu | Gly | Gln | Arg | Ala |
| 225 |  |  |  |  | 230 |  |  |  |  | 235 |  |  |  |  | 240 |
| Pro | Arg | Ser | Gln | Gln | Pro | Phe | Val | Val | Thr | Phe | Phe | Arg | Ala | Ser | Pro |
|  |  |  |  | 245 |  |  |  |  | 250 |  |  |  |  | 255 |  |
| Ser | Pro | Ile | Arg | Thr | Pro | Arg | Ala | Val | Arg | Pro | Leu | Arg | Arg | Arg | Gln |
|  |  |  | 260 |  |  |  |  | 265 |  |  |  |  | 270 |  |  |

| Pro | Lys | Lys | Ser | Asn | Glu | Leu | Pro | Gln | Ala | Asn | Arg | Leu | Pro | Gly | Ile |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Phe | Asp | Asp | Val | His | Gly | Ser | His | Gly | Arg | Gln | Val | Cys | Arg | Arg | His |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Glu | Leu | Tyr | Val | Ser | Phe | Gln | Asp | Leu | Gly | Trp | Leu | Asp | Trp | Val | Ile |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Ala | Pro | Gln | Gly | Tyr | Ser | Ala | Tyr | Tyr | Cys | Glu | Gly | Glu | Cys | Ser | Phe |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Pro | Leu | Asp | Ser | Cys | Met | Asn | Ala | Thr | Asn | His | Ala | Ile | Leu | Gln | Ser |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Leu | Val | His | Leu | Met | Lys | Pro | Asn | Ala | Val | Pro | Lys | Ala | Cys | Cys | Ala |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Pro | Thr | Lys | Leu | Ser | Ala | Thr | Ser | Val | Leu | Tyr | Tyr | Asp | Ser | Ser | Asn |
|-----|-----|-----|-----|-----|-----|-----|-----|-----|-----|-----|-----|-----|-----|-----|-----|
|     | 370 |     |     |     |     | 375 |     |     |     |     | 380 |     |     |     |     |

| Asn | Val | Ile | Leu | Arg | Lys | Ala | Arg | Asn | Met | Val | Val | Lys | Ala | Cys | Gly |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

| Cys | His |
|-----|-----|

( 2 ) INFORMATION FOR SEQ ID NO:9:

( i ) SEQUENCE CHARACTERISTICS:
        ( A ) LENGTH: 1926 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 93..1289
        ( D ) OTHER INFORMATION: /function="OSTEOGENIC PROTEIN"
                / product= "mOP2-PP"
                / note= "mOP2 cDNA"

( x i ) SEQUENCE DESCRIPTION: SEQ ID NO:9:

| GCCAGGCACA | GGTGCGCCGT | CTGGTCCTCC | CCGTCTGGCG | TCAGCCGAGC | CCGACCAGCT | 60 |
|---|---|---|---|---|---|---|

| ACCAGTGGAT | GCGCGCCGGC | TGAAAGTCCG | AG ATG | GCT | ATG | CGT | CCC | GGG | CCA | 113 |
|---|---|---|---|---|---|---|---|---|---|---|
| | | | Met | Ala | Met | Arg | Pro | Gly | Pro | |
| | | | 1 | | | | 5 | | | |

| CTC | TGG | CTA | TTG | GGC | CTT | GCT | CTG | TGC | GCG | CTG | GGA | GGC | GGC | CAC | GGT | 161 |
|-----|-----|-----|-----|-----|-----|-----|-----|-----|-----|-----|-----|-----|-----|-----|-----|-----|
| Leu | Trp | Leu | Leu | Gly | Leu | Ala | Leu | Cys | Ala | Leu | Gly | Gly | Gly | His | Gly | |
|     | 10  |     |     |     |     | 15  |     |     |     |     | 20  |     |     |     |     | |

| CCG | CGT | CCC | CCG | CAC | ACC | TGT | CCC | CAG | CGT | CGC | CTG | GGA | GCG | CGC | GAG | 209 |
|-----|-----|-----|-----|-----|-----|-----|-----|-----|-----|-----|-----|-----|-----|-----|-----|-----|
| Pro | Arg | Pro | Pro | His | Thr | Cys | Pro | Gln | Arg | Arg | Leu | Gly | Ala | Arg | Glu | |
|     | 25  |     |     |     | 30  |     |     |     |     | 35  |     |     |     |     |     | |

| CGC | CGC | GAC | ATG | CAG | CGT | GAA | ATC | CTG | GCG | GTG | CTC | GGG | CTA | CCG | GGA | 257 |
|-----|-----|-----|-----|-----|-----|-----|-----|-----|-----|-----|-----|-----|-----|-----|-----|-----|
| Arg | Arg | Asp | Met | Gln | Arg | Glu | Ile | Leu | Ala | Val | Leu | Gly | Leu | Pro | Gly | |
| 40  |     |     |     | 45  |     |     |     |     | 50  |     |     |     |     | 55  |     | |

| CGG | CCC | CGA | CCC | CGT | GCA | CAA | CCC | GCC | GCT | GCC | CGG | CAG | CCA | GCG | TCC | 305 |
|-----|-----|-----|-----|-----|-----|-----|-----|-----|-----|-----|-----|-----|-----|-----|-----|-----|
| Arg | Pro | Arg | Pro | Arg | Ala | Gln | Pro | Ala | Ala | Ala | Arg | Gln | Pro | Ala | Ser | |
|     |     |     |     | 60  |     |     |     |     | 65  |     |     |     |     | 70  |     | |

| GCG | CCC | CTC | TTC | ATG | TTG | GAC | CTA | TAC | CAC | GCC | ATG | ACC | GAT | GAC | GAC | 353 |
|-----|-----|-----|-----|-----|-----|-----|-----|-----|-----|-----|-----|-----|-----|-----|-----|-----|
| Ala | Pro | Leu | Phe | Met | Leu | Asp | Leu | Tyr | His | Ala | Met | Thr | Asp | Asp | Asp | |
|     |     |     | 75  |     |     |     |     | 80  |     |     |     |     | 85  |     |     | |

| GAC | GGC | GGG | CCA | CCA | CAG | GCT | CAC | TTA | GGC | CGT | GCC | GAC | CTG | GTC | ATG | 401 |
|-----|-----|-----|-----|-----|-----|-----|-----|-----|-----|-----|-----|-----|-----|-----|-----|-----|
| Asp | Gly | Gly | Pro | Pro | Gln | Ala | His | Leu | Gly | Arg | Ala | Asp | Leu | Val | Met | |
|     |     | 90  |     |     |     |     | 95  |     |     |     |     | 100 |     |     |     | |

| AGC | TTC | GTC | AAC | ATG | GTG | GAA | CGC | GAC | CGT | ACC | CTG | GGC | TAC | CAG | GAG | 449 |
|-----|-----|-----|-----|-----|-----|-----|-----|-----|-----|-----|-----|-----|-----|-----|-----|-----|
| Ser | Phe | Val | Asn | Met | Val | Glu | Arg | Asp | Arg | Thr | Leu | Gly | Tyr | Gln | Glu | |
|     | 105 |     |     |     |     | 110 |     |     |     |     | 115 |     |     |     |     | |

```
CCA CAC TGG AAG GAA TTC CAC TTT GAC CTA ACC CAG ATC CCT GCT GGG      497
Pro His Trp Lys Glu Phe His Phe Asp Leu Thr Gln Ile Pro Ala Gly
120             125                 130                 135

GAG GCT GTC ACA GCT GCT GAG TTC CGG ATC TAC AAA GAA CCC AGC ACC      545
Glu Ala Val Thr Ala Ala Glu Phe Arg Ile Tyr Lys Glu Pro Ser Thr
                140                 145                 150

CAC CCG CTC AAC ACA ACC CTC CAC ATC AGC ATG TTC GAA GTG GTC CAA      593
His Pro Leu Asn Thr Thr Leu His Ile Ser Met Phe Glu Val Val Gln
            155                 160                 165

GAG CAC TCC AAC AGG GAG TCT GAC TTG TTC TTT TTG GAT CTT CAG ACG      641
Glu His Ser Asn Arg Glu Ser Asp Leu Phe Phe Leu Asp Leu Gln Thr
        170                 175                 180

CTC CGA TCT GGG GAC GAG GGC TGG CTG GTG CTG GAC ATC ACA GCA GCC      689
Leu Arg Ser Gly Asp Glu Gly Trp Leu Val Leu Asp Ile Thr Ala Ala
    185                 190                 195

AGT GAC CGA TGG CTG CTG AAC CAT CAC AAG GAC CTG GGA CTC CGC CTC      737
Ser Asp Arg Trp Leu Leu Asn His His Lys Asp Leu Gly Leu Arg Leu
200                 205                 210                 215

TAT GTG GAA ACC GCG GAT GGG CAC AGC ATG GAT CCT GGC CTG GCT GGT      785
Tyr Val Glu Thr Ala Asp Gly His Ser Met Asp Pro Gly Leu Ala Gly
                220                 225                 230

CTG CTT GGA CGA CAA GCA CCA CGC TCC AGA CAG CCT TTC ATG GTA ACC      833
Leu Leu Gly Arg Gln Ala Pro Arg Ser Arg Gln Pro Phe Met Val Thr
            235                 240                 245

TTC TTC AGG GCC AGC CAG AGT CCT GTG CGG GCC CCT CGG GCA GCG AGA      881
Phe Phe Arg Ala Ser Gln Ser Pro Val Arg Ala Pro Arg Ala Ala Arg
        250                 255                 260

CCA CTG AAG AGG AGG CAG CCA AAG AAA ACG AAC GAG CTT CCG CAC CCC      929
Pro Leu Lys Arg Arg Gln Pro Lys Lys Thr Asn Glu Leu Pro His Pro
    265                 270                 275

AAC AAA CTC CCA GGG ATC TTT GAT GAT GGC CAC GGT CCC CGC GGC AGA      977
Asn Lys Leu Pro Gly Ile Phe Asp Asp Gly His Gly Ser Arg Gly Arg
280                 285                 290                 295

GAG GTT TGC CGC AGG CAT GAG CTC TAC GTC AGC TTC CGT GAC CTT GGC      1025
Glu Val Cys Arg Arg His Glu Leu Tyr Val Ser Phe Arg Asp Leu Gly
                300                 305                 310

TGG CTG GAC TGG GTC ATC GCC CCC CAG GGC TAC TCT GCC TAT TAC TGT      1073
Trp Leu Asp Trp Val Ile Ala Pro Gln Gly Tyr Ser Ala Tyr Tyr Cys
            315                 320                 325

GAG GGG GAG TGT GCT TTC CCA CTG GAC TCC TGT ATG AAC GCC ACC AAC      1121
Glu Gly Glu Cys Ala Phe Pro Leu Asp Ser Cys Met Asn Ala Thr Asn
        330                 335                 340

CAT GCC ATC TTG CAG TCT CTG GTG CAC CTG ATG AAG CCA GAT GTT GTC      1169
His Ala Ile Leu Gln Ser Leu Val His Leu Met Lys Pro Asp Val Val
    345                 350                 355

CCC AAG GCA TGC TGT GCA CCC ACC AAA CTG AGT GCC ACC TCT GTG CTG      1217
Pro Lys Ala Cys Cys Ala Pro Thr Lys Leu Ser Ala Thr Ser Val Leu
360                 365                 370                 375

TAC TAT GAC AGC AGC AAC AAT GTC ATC CTG CGT AAA CAC CGT AAC ATG      1265
Tyr Tyr Asp Ser Ser Asn Asn Val Ile Leu Arg Lys His Arg Asn Met
                380                 385                 390

GTG GTC AAG GCC TGT GGC TGC CAC TGAGGCCCCG CCCAGCATCC TGCTTCTACT     1319
Val Val Lys Ala Cys Gly Cys His
            395

ACCTTACCAT CTGGCCGGGC CCCTCTCCAG AGGCAGAAAC CCTTCTATGT TATCATAGCT    1379

CAGACAGGGG CAATGGGAGG CCCTTCACTT CCCCTGGCCA CTTCCTGCTA AAATTCTGGT    1439

CTTTCCCAGT TCCTCTGTCC TTCATGGGGT TTCGGGGCTA TCACCCCGCC CTCTCCATCC    1499

TCCTACCCCA AGCATAGACT GAATGCACAC AGCATCCCAG AGCTATGCTA ACTGAGAGGT    1559
```

```
CTGGGGTCAG CACTGAAGGC CCACATGAGG AAGACTGATC CTTGGCCATC CTCAGCCCAC      1619

AATGGCAAAT TCTGGATGGT CTAAGAAGGC CCTGGAATTC TAAACTAGAT GATCTGGGCT      1679

CTCTGCACCA TTCATTGTGG CAGTTGGGAC ATTTTTAGGT ATAACAGACA CATACACTTA      1739

GATCAATGCA TCGCTGTACT CCTTGAAATC AGAGCTAGCT TGTTAGAAAA AGAATCAGAG      1799

CCAGGTATAG CGGTGCATGT CATTAATCCC AGCGCTAAAG AGACAGAGAC AGGAGAATCT      1859

CTGTGAGTTC AAGGCCACAT AGAAAGAGCC TGTCTCGGGA GCAGGAAAAA AAAAAAAAAC      1919

GGAATTC                                                                1926
```

( 2 ) INFORMATION FOR SEQ ID NO:10:

( i ) SEQUENCE CHARACTERISTICS:
( A ) LENGTH: 399 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Met Ala Met Arg Pro Gly Pro Leu Trp Leu Leu Gly Leu Ala Leu Cys
 1               5                  10                      15

Ala Leu Gly Gly Gly His Gly Pro Arg Pro Pro His Thr Cys Pro Gln
                20                  25                  30

Arg Arg Leu Gly Ala Arg Glu Arg Arg Asp Met Gln Arg Glu Ile Leu
            35                  40                  45

Ala Val Leu Gly Leu Pro Gly Arg Pro Arg Pro Arg Ala Gln Pro Ala
        50                  55                  60

Ala Ala Arg Gln Pro Ala Ser Ala Pro Leu Phe Met Leu Asp Leu Tyr
65                  70                  75                  80

His Ala Met Thr Asp Asp Asp Gly Gly Pro Pro Gln Ala His Leu
                85                  90                  95

Gly Arg Ala Asp Leu Val Met Ser Phe Val Asn Met Val Glu Arg Asp
            100                 105                 110

Arg Thr Leu Gly Tyr Gln Glu Pro His Trp Lys Glu Phe His Phe Asp
        115                 120                 125

Leu Thr Gln Ile Pro Ala Gly Glu Ala Val Thr Ala Ala Glu Phe Arg
130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
        195                 200                 205

Lys Asp Leu Gly Leu Arg Leu Tyr Val Glu Thr Ala Asp Gly His Ser
    210                 215                 220

Met Asp Pro Gly Leu Ala Gly Leu Leu Gly Arg Gln Ala Pro Arg Ser
225                 230                 235                 240

Arg Gln Pro Phe Met Val Thr Phe Phe Arg Ala Ser Gln Ser Pro Val
                245                 250                 255

Arg Ala Pro Arg Ala Ala Arg Pro Leu Lys Arg Arg Gln Pro Lys Lys
            260                 265                 270

Thr Asn Glu Leu Pro His Pro Asn Lys Leu Pro Gly Ile Phe Asp Asp
        275                 280                 285
```

| | | | | | | | | | | | | | | |
|---|---|---|---|---|---|---|---|---|---|---|---|---|---|---|
| Gly | His | Gly | Ser | Arg | Gly | Arg | Glu | Val | Cys | Arg | Arg | His | Glu | Leu | Tyr |
| | 290 | | | | | 295 | | | | | 300 | | | | |
| Val | Ser | Phe | Arg | Asp | Leu | Gly | Trp | Leu | Asp | Trp | Val | Ile | Ala | Pro | Gln |
| 305 | | | | | 310 | | | | | 315 | | | | | 320 |
| Gly | Tyr | Ser | Ala | Tyr | Tyr | Cys | Glu | Gly | Glu | Cys | Ala | Phe | Pro | Leu | Asp |
| | | | | 325 | | | | | 330 | | | | | 335 | |
| Ser | Cys | Met | Asn | Ala | Thr | Asn | His | Ala | Ile | Leu | Gln | Ser | Leu | Val | His |
| | | | 340 | | | | | 345 | | | | | 350 | | |
| Leu | Met | Lys | Pro | Asp | Val | Val | Pro | Lys | Ala | Cys | Cys | Ala | Pro | Thr | Lys |
| | | 355 | | | | | 360 | | | | | 365 | | | |
| Leu | Ser | Ala | Thr | Ser | Val | Leu | Tyr | Tyr | Asp | Ser | Ser | Asn | Asn | Val | Ile |
| | | 370 | | | | | 375 | | | | | 380 | | | |
| Leu | Arg | Lys | His | Arg | Asn | Met | Val | Val | Lys | Ala | Cys | Gly | Cys | His | |
| 385 | | | | | 390 | | | | | 395 | | | | | |

( 2 ) INFORMATION FOR SEQ ID NO:11:

( i ) SEQUENCE CHARACTERISTICS:
        ( A ) LENGTH: 884 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..884
        ( D ) OTHER INFORMATION: /note= "hOP-2 genomic sequence"

( i x ) FEATURE:
        ( A ) NAME/KEY: exon
        ( B ) LOCATION: 1..837
        ( D ) OTHER INFORMATION: /note= "EXON ONE"

( i x ) FEATURE:
        ( A ) NAME/KEY: misc_feature
        ( B ) LOCATION: 884
        ( D ) OTHER INFORMATION: /note= "A GAP OCCURS BETWEEN
        POSTIONS 884 IN THIS SEQUENCE AND POSITION 1 IN
        SEQ ID NO 14"

( x i ) SEQUENCE DESCRIPTION: SEQ ID NO:11:

| | | | | | |
|---|---|---|---|---|---|
| GGAATTCCGG | CCACAGTGGC | GCCGGCAGAG | CAGGAGTGGC | TGGAGGAGCT | GTGGTTGGAG | 60 |
| CAGGAGGTGG | CACGGCAGGG | CTGGAGGGCT | CCCTATGAGT | GGCGGAGACG | GCCCAGGAGG | 120 |
| CGCTGGAGCA | ACAGCTCCCA | CACCGCACCA | AGCGGTGGCT | GCAGGAGCTC | GCCCATCGCC | 180 |
| CCTGCGCTGC | TCGGACCGCG | GCCACAGCCG | GACTGGCGGG | TACGGCGGCG | ACAGACGGAT | 240 |
| TGGCCGAGAG | TCCCAGTCCG | CAGAGTAGCC | CCGGCCTCGA | GGCGGTGGCG | TCCGCGTCCT | 300 |
| CTCGTCCAGG | AGCCAGGACA | GGTGTCGCGC | GGCGGGCCGT | CCAGGGACCG | CGCTGAGGCC | 360 |
| GCGGTCGCCC | GTCCCGCCCC | GCCCCGCCGC | CCGCCGCCCG | CCGAGCCCAG | CCTCCTTGCC | 420 |
| GTCGGGGCGT | CCCCAGGCCC | TGGGTCGGCC | GCGGAGCCGA | TGCGCGCCCG | CTGAGCGCCC | 480 |
| CAGCTGAGCG | CCCCCGGCCT | GCCATGACCG | CGCTCCCCGG | CCCGCTCTGG | CTCCTGGGCC | 540 |
| TGGCGCTATG | CGCGCTGGGC | GGGGGCGGCC | CCGGCCTGCG | ACCCCCGCCC | GGCTGTCCCC | 600 |
| AGCGACGTCT | GGGCGCGCGC | GAGCGCCGGG | ACGTGCAGCG | CGAGATCCTG | GCGGTGCTCG | 660 |
| GGCTGCCTGG | GCGGCCCCGG | CCCCGCGCGC | CACCCGCCGC | CTCCCGGCTG | CCCGCGTCCG | 720 |
| CGCCGCTCTT | CATGCTGGAC | CTGTACCACG | CCATGGCCGG | CGACGACGAC | GAGGACGGCG | 780 |
| CGCCCGCGGA | GCGGCGCCTG | GGCCGCGCCG | ACCTGGTCAT | GAGCTTCGTT | AACATGGGTG | 840 |

AGTGCGGCGC CCGCGCGGGG ACCCTCGGAG TAAACTGGCT GCAG 884

( 2 ) INFORMATION FOR SEQ ID NO:12:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=Generic-Seq-7
          / note= "wherein each Xaa is independently selected from
          a group of one or more specified amino acids as defined
          in the specification."

( x i ) SEQUENCE DESCRIPTION: SEQ ID NO:12:

```
Leu  Xaa  Xaa  Xaa  Phe  Xaa  Xaa  Xaa  Gly  Trp  Xaa  Xaa  Xaa  Xaa  Xaa
 1                   5                        10                       15

Pro  Xaa  Xaa  Xaa  Xaa  Ala  Xaa  Tyr  Cys  Xaa  Gly  Xaa  Cys  Xaa  Xaa  Pro
          20                        25                       30

Xaa  Xaa  Xaa  Xaa  Xaa  Xaa  Xaa  Xaa  Asn  His  Ala  Xaa  Xaa  Xaa  Xaa  Xaa
               35                        40                       45

Xaa  Xaa  Xaa  Xaa  Xaa  Xaa  Xaa  Xaa  Xaa  Xaa  Xaa  Xaa  Cys  Cys  Xaa  Pro
     50                             55                       60

Xaa  Xaa  Xaa  Xaa  Xaa  Xaa  Xaa  Xaa  Leu  Xaa  Xaa  Xaa  Xaa  Xaa  Xaa  Xaa
 65                       70                       75                       80

Val  Xaa  Leu  Xaa  Xaa  Xaa  Xaa  Xaa  Met  Xaa  Val  Xaa  Xaa  Cys  Xaa  Cys
               85                        90                            95

Xaa
```

( 2 ) INFORMATION FOR SEQ ID NO:13:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=Generic-Seq-8
          / note= "wherein each Xaa is independently selected from
          a group of one or more specified amino acids as defined
          in the specification."

( x i ) SEQUENCE DESCRIPTION: SEQ ID NO:13:

```
Cys  Xaa  Xaa  Xaa  Xaa  Leu  Xaa  Xaa  Xaa  Phe  Xaa  Xaa  Xaa  Gly  Trp  Xaa
 1                        5                        10                       15

Xaa  Xaa  Xaa  Xaa  Xaa  Pro  Xaa  Xaa  Xaa  Xaa  Ala  Xaa  Tyr  Cys  Xaa  Gly
               20                        25                       30

Xaa  Cys  Xaa  Xaa  Pro  Xaa  Xaa  Xaa  Xaa  Xaa  Xaa  Xaa  Xaa  Asn  His  Ala
          35                        40                       45

Xaa  Xaa  Xaa  Xaa  Xaa  Xaa  Xaa  Xaa  Xaa  Xaa  Xaa  Xaa  Xaa  Xaa  Xaa  Xaa
     50                             55                       60

Xaa  Cys  Cys  Xaa  Pro  Xaa  Xaa  Xaa  Xaa  Xaa  Xaa  Xaa  Xaa  Leu  Xaa  Xaa
 65                       70                       75                       80

Xaa  Xaa  Xaa  Xaa  Xaa  Val  Xaa  Leu  Xaa  Xaa  Xaa  Xaa  Xaa  Met  Xaa  Val
```

|  | 85 |  | 90 |  | 95 |
|---|---|---|---|---|---|

Xaa Xaa Cys Xaa Cys Xaa
            100

( 2 ) INFORMATION FOR SEQ ID NO:14:

( i ) SEQUENCE CHARACTERISTICS:
        ( A ) LENGTH: 950 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1
        ( D ) OTHER INFORMATION: /note= "A GAP OCCURS BETWEEN
        POSTION 884 IN SEQ ID NO: 11 AND POSITION 1 IN THIS
        SEQUENCE"

( i x ) FEATURE:
        ( A ) NAME/KEY: exon
        ( B ) LOCATION: 204..393
        ( D ) OTHER INFORMATION: /note= "EXON TWO"

( i x ) FEATURE:
        ( A ) NAME/KEY: exon
        ( B ) LOCATION: 466..930
        ( D ) OTHER INFORMATION: /note= "EXON THREE"

( i x ) FEATURE:
        ( A ) NAME/KEY: misc_feature
        ( B ) LOCATION: 1..950
        ( D ) OTHER INFORMATION: /note= "hOP-2 genomic sequence"

( x i ) SEQUENCE DESCRIPTION: SEQ ID NO:14:

```
CTGCAGGGCC  TCTTCTGGCT  CTACACCCCG  GGACCAAGCC  TGGAACAAAC  GTTTGCACTA      60
AATGAAGCCG  GCCCCACCCA  GGCCTCCCTG  GGTCCGCTCC  ACCTTGAGTG  GTGGGTGGCT     120
GGGGGCGGTG  GCTCACACCA  GCTCTGCCCC  CTCCAGAGCC  CGAGCCATTC  TGAGTGCCAG     180
CCCAGCGCTG  CTTTGTCTTC  TAGTGGAGCG  AGACCGTGCC  CTGGGCCACC  AGGAGCCCCA     240
TTGGAAGGAG  TTCCGCTTTG  ACCTGACCCA  GATCCCGGCT  GGGGAGGCGG  TCACAGCTGC     300
GGAGTTCCGG  ATTTACAAGG  TGCCCAGCAT  CCACCTGCTC  AACAGGACCC  TCCACGTCAG     360
CATGTTCCAG  GTGGTCCAGG  AGCAGTCCAA  CAGGTGCCTT  CCCCTTGGCC  CGGGTGCCCA     420
CCTAACCCCC  CACCTCACAG  TCTCATGGTC  AAGGCAGCCC  AGCAGGAGT   CGTGGTGGGT     480
GAAAGAGAGC  CTCAAAGATG  GGAAGGATGC  TTGGCCCGAG  GCCCTGCACT  GTGGGAAGAG     540
CCCCAGTGAC  AATCCTGACT  TCAAGTCCCT  GCCCTCCATC  CTGCTGTGGG  GACTTGGACA     600
TGGTCACTGA  GACTCAGTTT  CCCCATGTGT  ACACCTCTGT  GGGCTGAGGC  AATGAGATGA     660
GGCTCAGAAG  GGCGCAGCCA  GAGTCAGGTG  GGAGACGCTC  CGGTGACAGC  CCCCAGCGGG     720
CCCTGGAGAC  ACGGAGGCAG  CTGTGCCGGC  CGCCGGTTAA  TTGTTCTTTC  ATGTCCACAG     780
GGGAGTCTGA  CTTGTTCTTT  TTGGATCTTC  AGACGCTCCG  AGCTGGAGAC  GAGGGCTGGC     840
TGGTGCTGGA  TGTCACAGCA  GCCAGTGACT  GCTGGTTGCT  GAAGCGTCAC  AAGGACCTGG     900
GACTCCGCCT  CTATGTGGAG  ACTGAGGACG  GTGAGGCTGG  GGCTCTGCAG                 950
```

( 2 ) INFORMATION FOR SEQ ID NO:15:

( i ) SEQUENCE CHARACTERISTICS:
        ( A ) LENGTH: 4584 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: misc_feature
    ( B ) LOCATION: 1..4584
    ( D ) OTHER INFORMATION: /note= "hOP-2 genomic sequence"

( i x ) FEATURE:
    ( A ) NAME/KEY: misc_feature
    ( B ) LOCATION: 1
    ( D ) OTHER INFORMATION: /note= "A GAP OCCURS BETWEEN POSITION 950 IN SEQ ID NO: 14 AND POSITION 1 IN THIS SEQUENCE"

( i x ) FEATURE:
    ( A ) NAME/KEY: exon
    ( B ) LOCATION: 49..243
    ( D ) OTHER INFORMATION: /note= "EXON FOUR"

( i x ) FEATURE:
    ( A ) NAME/KEY: exon
    ( B ) LOCATION: 1064..1147
    ( D ) OTHER INFORMATION: /note= "EXON FIVE"

( i x ) FEATURE:
    ( A ) NAME/KEY: exon
    ( B ) LOCATION: 1673..1783
    ( D ) OTHER INFORMATION: /note= "EXON SIX"

( i x ) FEATURE:
    ( A ) NAME/KEY: exon
    ( B ) LOCATION: 4282..4527
    ( D ) OTHER INFORMATION: /note= "EXON SEVEN"

( x i ) SEQUENCE DESCRIPTION: SEQ ID NO:15:

```
CTGCAGAGCC ACTGCCCGTG AGTGACCCCT CTCTCCTTTC TGTCTCAGGG CACAGCGTGG      60
ATCCTGGCCT GGCCGGCCTG CTGGGTCAAC GGGCCCCACG CTCCCAACAG CCTTTCGTGG     120
TCACTTTCTT CAGGGCCAGT CCGAGTCCCA TCCGCACCCC TCGGGCAGTG AGGCCACTGA     180
GGAGGAGGCA GCCGAAGAAA AGCAACGAGC TGCCGCAGGC CAACCGACTC CCAGGGATCT     240
TTGGTGAGGG TCGGGCAGGC TGGGGCGAGG CTGTGGCTGT CTGGCTGAGA GAGGCAGGGC     300
GAGAACCAAG TGGTGGCCCA GAGCCCAGAG CCTCAGGCTA GGTCGGTTCA AGCTGACGGC     360
CACTCTCCAG CCACCTTTCC TGACACCATC TTGGCCCTGA TGCACCCTGG TGACCGGCAC     420
TCCGAGGCCT GTCCTGGCTG TCCCTGCTGC CAGAAGTCTC CCTCTCTCCC CCTGGCTCCT     480
CCGGGTCTTT CTCAGGAGCC TCCTTCAGAA TCAGCTGCCC CTTCCCTGGG AGCCGCAGCC     540
CCTCATGACC TGCGGTTGTG CCTGGGCACC TGTGGATCCT CGGTTGCTTA TGCGATTTTC     600
TCCCCAACTG GCCAAGCTTC AGGATCAGGG ACAGGCCTGA CCCAACCCCG TGCCCTCCTT     660
CCCAGGGAGT CGGCCCTTGA CTGGCCTGGT CGTGAGCCAC TTGAACCTCG GAATGGGTG      720
TGGCAGGAGA GGGTGGGCTG GAGTCACAGG GGTCTCCAGA GAGGAGGAGG CACAGGATGG     780
CCGAGGGTCC TGCTGGGCTG TTTACTGGAG CATAAAGATG CTCATAGGCT GAAGGACAGG     840
GGAGGACTGG GCACAGTGTC ACTCTAGCCA TTGGGAGCCA TGGCAGGCTT CTGAGCTGGG     900
TCATGGTACA AGCAGAGTTC CAGGGATGGG CTTTATGAGC CAAATGGTTT CCTGTCATTC     960
ATTTATTTGA CAAATGTGCT CATCAGGGCA TCCCCCACCC TGGTACCCCA TAGTAGCTGC    1020
ACACAGCAGG AACCCCAGAA AAGACCTTGC CCCTTCTGTC CCTGCAGATG ACGTCCACGG    1080
CTCCCACGGC CGGCAGGTCT GCCGTCGGCA CGAGCTCTAC GTCAGCTTCC AGGACCTCGG    1140
CTGGCTGGTA ATTGCTGACT CTCCTTGTTT CTGAAATGAC AATCACCACC TGTAGATCAG    1200
AAGTGAATCT GCAGGGAGGA CATAGAATCA TGGTGACTTC AATTTTCTTA TGTATTTTTT    1260
TCTTCTGTGT TTTCCAAGTT TTCTAAAGTG AGAATATGGT GAGAAAGGGT TTGTTGTTG     1320
```

| | | | | | |
|---|---|---|---|---|---|
| TTGTTGTGTT | TTTTGTTTTT | TTTTAAAAAC | CCATGAAAAT | GAAGACTGAA | TCAACCAACT | 1380 |
| AAGCTGTCAG | CATTGCCGCA | GGGTAACTGA | GACCTCCCTG | CATTGGCTAC | GACTGCAGCT | 1440 |
| CTGGGAGGTG | TGGGCAGGGG | AGGGCCGGCT | GGGGAGGGCC | GGCTGGGGAG | GGGACACAAA | 1500 |
| GTGAAGATGG | GGGTTGTTGG | GCCTGAGCTC | CTGCCCAGCC | TTTTCCGCCG | GGGTTCCTGG | 1560 |
| GTGGATTCAA | GCCTCTTGGG | GGAGACGCGC | TGCAGGGCTG | GAGGATGGGC | TTTGGGCCCT | 1620 |
| GAGGCTCAGG | GAGGAGCACA | TGGATGGGAC | TCACCTTCTC | CCTTGCCCCC | AGGACTGGGT | 1680 |
| CATCGCTCCC | CAAGGCTACT | CGGCCTATTA | CTGTGAGGGG | GAGTGCTCCT | TCCCACTGGA | 1740 |
| CTCCTGCATG | AATGCCACCA | ACCACGCCAT | CCTGCAGTCC | CTGGTCGATA | CCGTCGCCCA | 1800 |
| TCCTGCCCAG | CCCCCTGGTG | GAGGCCCTGC | AGAGAGGGGT | CTGGTCCAGC | CAGCCGGGAG | 1860 |
| GCAGTGAGGC | CACCTGCTCC | ATGTCTCGGG | GCTTTGTCTG | CACAGAGTCA | GTAACGTCGC | 1920 |
| TAACTTCCCA | CAGCTCTGCA | GGAACTGGTC | CTCATACAGC | CACACTACTA | CACATAGACC | 1980 |
| CACACCCAAA | CACGGACACA | CGTGAACAGT | CGCGTATCAT | GCCTGTTCTA | TGCACTGAAC | 2040 |
| AAACTCCTGT | GGGACACTTA | CACACCTGCG | TGCGGCGCTC | AGAGGCACAG | CACATGAAAC | 2100 |
| AGATGTGTAC | ACTGTGTGGG | GGCTGTGTGA | TCTTAACACA | CGGGCCCCCG | AGTACGCTGG | 2160 |
| CAAGTCTGAC | CGCCCGTGAT | ATGTGCGCAC | AGTGTGTGGG | GTGTGCGTGT | GCATCACCCA | 2220 |
| CCTGTGCCGC | ACCACAGGTA | GGAAGCTTCT | AGATGGTGTG | GCTCTCAACC | TTTTGGCTTT | 2280 |
| TTCCCGCAGT | TTCTCTCTTG | GCTGTCTGTG | TTTTCTCTGG | ATCCCCTGGC | TTTTGATGCC | 2340 |
| GTTGGTGTCT | GGGGCAACCT | TAAAGGACAA | AAGCAGGCTT | CTGATGGGAT | CACTGGTGCT | 2400 |
| GCTCACCACT | GAGTGCTCGT | GTGTTTGCGG | ATTCTGGCAC | CGAGGCTTCC | TTCTAGAAGT | 2460 |
| TTTTACCTAG | AATCCCAGTT | CCTGGTATTG | CACAGCCTTA | TGTTTTCCTC | TTAGGAGGTT | 2520 |
| CAACGGTGAT | GCCTTGATCA | GGCGCAGTGG | CTCACCCTGT | AATCGCAGCA | CACGAGCCCA | 2580 |
| GAAGTTCAAG | ACAAGCCTGA | GCAACACAGC | AAAACCCTGT | CTCTAAAATA | AAAATTAAAA | 2640 |
| CACACACACA | CACACACACA | CACACACACA | CACGTGCGCA | CACAATGCCT | TGGTGTGAGA | 2700 |
| GGAAAGAAAT | TACCAAAAGC | TGCTCTGAGC | CTATGATAAT | ACTTCCTTTC | TGGGCAGTCA | 2760 |
| AATGGTGTTT | GCTGGACACC | CTGGAGCCAT | CTCCTTGGAA | AGGCCCAGGG | GTGATGAGGA | 2820 |
| GCTCCGTCGG | GGTGGCCTGG | CCAGCACCTT | TATGCCGTGT | GGTTCTCACA | GCTGCATGTG | 2880 |
| TGGGAGGTAC | ATGGGAAGGT | GACTGCACCT | GCGCTCCTGG | ACTCCATCTC | CTCTGCCCTT | 2940 |
| GCCCCTGCCC | CTCACGTGCA | ACTAGAGTGA | GTGCTCACAG | CCTACAGGGC | AGCAAACAGG | 3000 |
| CACTGTGCTC | TAGGGGAGGC | TGTCGGTGGG | CACAGAAGCA | AACCAACCGT | GGAGTTGACA | 3060 |
| CCTCCTGTGA | GGAAGAGCAG | ACGAGCCGTG | CCGTCAGTGG | AGTGAGACTG | GCCCAGCTC | 3120 |
| TCCACACAAG | GAGGGGCACG | TCAGCAGCTG | GAGGAGGAAT | GTTCCAGAAG | GAGCAAGTGC | 3180 |
| AAGGCCCTAA | GACAGGAGCA | GGCTGGCCCT | AAGTTCAGGG | CAGGGGAGGA | GAGGGGCTGG | 3240 |
| GTGCAGTGAA | GGGGAGGAGA | GTGGAGGGAG | GTGATCCGGG | GTGATAGGCC | AGCTCCCGTA | 3300 |
| GCCTGGGTTC | CCTGGGAAGA | GGGTGGATTT | TATTCCAAGC | AACCCCAGAG | GCTGTCAGAG | 3360 |
| GTCTTCAGCA | AAGAGTGTCC | TTGGTCTGCG | TCACCCTCCA | GAAGGACCTT | TCTGGCTTGG | 3420 |
| GGAGGTCGCG | GGAGTGGAAG | GCAGAGGAGC | AGGGGATGAG | TGAGGGCTGC | TGTGGTCACC | 3480 |
| TGGCAGGTGA | TGGCAGCTCG | ACTGGGCAGG | TGGTCCGAGG | CAGCACGGAG | GTGGAGGTTG | 3540 |
| AGCCAGGGGC | TGCTCTCAGG | GAAGGGAGGA | GGCGAAGGA | GTCATCCAGG | AGGCCTCCCA | 3600 |
| GGCGGGAGCT | ATGATGTCAG | GGCGGGAGGA | ATTCTATGTT | CCACTGAGGC | CTCATTAGAC | 3660 |
| CCCCAAGTGC | AGAAGTGGGA | AGGGGAGCAG | GATCCGCAAG | TCTGGAGTTC | AGAAGAGAGG | 3720 |

| | | | | | | |
|---|---|---|---|---|---|---|
| TCCAAGCTGA | GCCAGGGGAG | TGGAGAGGTG | CGGGCCAATG | CAGGGCCTTG | AAGTGCTGAG | 3780 |
| GGCGGATCGA | GTCCTCTGGG | AGAAGGAGCA | GCACAGGAGA | GGGGGCGAGG | CTGGCTCCCA | 3840 |
| GAGCCTGGGG | AGGGAGGCAG | GTGTGGGGAG | GCAGAGCTTG | GGGGGGTCTG | AAGGGCTATA | 3900 |
| AGAAGACAGT | GGTCCTTCCA | GGTTCCCCCT | TGGACCTCAC | TAAGGGCACA | AACCTGGCCA | 3960 |
| TGAGGTTCTC | CTTCCCATTA | TCCCCAGGAG | GAAGTCTGAG | CCCTTGGCCT | GGGACTCGAG | 4020 |
| GCCCCTCATT | AGTGCCCTGC | CCACCTGCCC | CACACCCTGG | GGCTGCCATG | TATCCCTCCC | 4080 |
| TGGGCACTGT | GGGCACCACA | GCTCCCGCTC | CCAGAGCTCT | CAGGGCTGCT | CTTATTCCTG | 4140 |
| TTAATAATTC | TTATTATTGT | GCTGCTCCCA | TGTGGCTTGG | AGATGGCCAG | GGCAGGGAGC | 4200 |
| AGGTGGAGCT | GGGGCGGGCT | AGGTGGGTCC | TCAGAGGAGG | CCACTGGCTC | ATGCCCCTGC | 4260 |
| CTGTGCTCCC | TTCCTGGCCA | GGTGCACCTG | ATGAAGCCAA | ACGCAGTCCC | CAAGGCGTGC | 4320 |
| TGTGCACCCA | CCAAGCTGAG | CGCCACCTCT | GTGCTCTACT | ATGACAGCAG | CAACAACGTC | 4380 |
| ATCCTGCGCA | AGCACCGCAA | CATGGTGGTC | AAGGCCTGCG | GCTGCCACTG | AGTCAGCCCG | 4440 |
| CCCAGCCCTA | CTGCAGCCAC | CCTTCTCATC | TGGATCGGGC | CCTGCAGAGG | CAGAAAACCC | 4500 |
| TTAAATGCTG | TCACAGCTCA | AGCAGGAGTG | TCAGGGCCC | TCACTCTCTG | TGCCTACTTC | 4560 |
| CTGTCAGGCT | TCTGGTCCTT | TCTC | | | | 4584 |